(12) United States Patent
Caves et al.

(10) Patent No.: US 10,988,761 B2
(45) Date of Patent: Apr. 27, 2021

(54) HTP PLATFORM FOR THE GENETIC ENGINEERING OF CHINESE HAMSTER OVARY CELLS

(71) Applicant: Zymergen Inc., Emeryville, CA (US)

(72) Inventors: Kate Caves, Emeryville, CA (US); Amarjeet Singh, Emeryville, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

(21) Appl. No.: 16/933,540

(22) Filed: Jul. 20, 2020

(65) Prior Publication Data

US 2020/0347383 A1    Nov. 5, 2020

Related U.S. Application Data

(63) Continuation of application No. PCT/US2019/023106, filed on Mar. 20, 2019.

(60) Provisional application No. 62/645,708, filed on Mar. 20, 2018.

(51) Int. Cl.
*C12N 15/10* (2006.01)

(52) U.S. Cl.
CPC ..... *C12N 15/1079* (2013.01); *C12N 15/1058* (2013.01)

(58) Field of Classification Search
None
See application file for complete search history.

(56) References Cited

U.S. PATENT DOCUMENTS

| | | | |
|---|---|---|---|
| 4,435,504 A | 3/1984 | Zuk et al. | |
| 4,855,240 A | 8/1989 | Rosenstein et al. | |
| 4,980,298 A | 12/1990 | Blake et al. | |
| 5,591,645 A | 1/1997 | Rosenstein | |
| 5,605,793 A | 2/1997 | Stemmer | |
| 5,837,458 A | 11/1998 | Minshull et al. | |
| 6,040,439 A | 3/2000 | Hayakawa et al. | |
| 6,090,592 A | 7/2000 | Adams et al. | |
| 6,300,070 B1 | 10/2001 | Boles et al. | |
| 7,115,400 B1 | 10/2006 | Adessi et al. | |
| 10,047,358 B1* | 8/2018 | Serber | G16B 5/00 |
| 2010/0137143 A1 | 6/2010 | Rothberg et al. | |
| 2010/0216648 A1 | 8/2010 | Staehler et al. | |
| 2010/0304982 A1 | 12/2010 | Hinz et al. | |
| 2011/0172127 A1 | 7/2011 | Jacobsen et al. | |
| 2015/0337292 A1* | 11/2015 | Guenther | C07K 16/005 506/26 |
| 2017/0159045 A1 | 6/2017 | Serber et al. | |
| 2017/0316353 A1 | 11/2017 | Frewen et al. | |

FOREIGN PATENT DOCUMENTS

| | | |
|---|---|---|
| EP | 0972081 B1 | 6/2007 |
| WO | WO 2011/154147 A1 | 12/2011 |
| WO | WO 2016/073690 A1 | 5/2016 |
| WO | WO 2017/100376 A2 | 6/2017 |
| WO | WO 2019/183183 A1 | 9/2019 |

OTHER PUBLICATIONS

[Author Unknown] GPU-Based Deep Learning Inference: A Performance and Power Analysis, NVidia Whitepaper, Nov. 2015, 12 pages.
Aslanidis and De Jong, "Ligation-independent cloning of PCR products (LIC-PCR)." Nucleic Acids Research (Oct. 25, 1990); 18(20): 6069-6074.
Azhayev et al., "Amide group assisted 3'-dephosphorylation of oligonucleotides synthesized on universal A-supports", Tetrahedron (Jun. 4, 2001); 57(23): 4977-4986.
Becker, et al., "From zero to hero-design-based systems metabolic engineering of Corynebacterium glutamicum for L-lysine production." Metabolic Engineering (Mar. 2077); 13(2):159-168.
Bentley, et al., "Accurate whole human genome sequencing using reversible terminator chemistry." Nature (2008); 456(7218): 53-59.
Bird, et al., "Single-chain antigen binding proteins." Science (Oct. 21, 1988); 242(4877): 423-426.
Costanzo, et al., "The genetic landscape of a cell." Science (Jan. 22, 2010); 327 (5964): 425-431.
Crameri, et al., "DNA shuffling of a family of genes from diverse species accelerates directed evolution." Nature (Jan. 15, 1998); 391(6664): 288-291.
Crameri, et al., "Molecular evolution of an arsenate detoxification pathway by DNA shuffling." Nature Biotechnology (May 1997); 15(5): 436-438.
Czar, et al. "Gene synthesis demystified." Trends in Biotechnology (Feb. 2009); 27(2): 63-72. Epub Dec. 26, 2008.
Dahl, et al., "Multi-task Neural Networks for QSAR Predictions" Dept. of Computer Science, Univ. of Toronto, Jun. 2014, 21 pages (arXiv:1406.1231 [stat.ML]).
Damha, et al., "An improved procedure for derivatization of controlled-pore glass beads for solid-phase oligonucleotide synthesis." Nucleic Acids Research (Jul. 11, 1990); 18(13): 3813-3821.
De Almeida, et al., "Transgenic expression of two marker genes under the control of an Arabidopsis rbcS promoter: Sequences encoding the Rubisco transit peptide increase expression levels". Mol Gen Genet (Jul. 1989); 218: 78-86.
Drmanac, et al., "Human genome sequencing using unchained base reads on self-assembling DNA nanoarrays." Science (Jan. 1, 2010); 327(5961): 78-81.
Eid, et al., "Real-time DNA sequencing from single polymerase molecules." Science (Jan. 2, 2009); 323(5910): 133-138. Epub Nov. 20, 2008.

(Continued)

*Primary Examiner* — Channing S Mahatan
(74) *Attorney, Agent, or Firm* — Cooley LLP

(57) ABSTRACT

Presented herein is a high-throughput (HTP) genomic engineering platform for improving the production of therapeutic proteins in Chinese hamster ovary (CHO) cells. The disclosed HTP genomic engineering platform is computationally driven and integrates molecular biology, automation, and advanced machine learning protocols. The platform utilizes a unique suite of HTP genetic engineering tools to explore the genomic landscape associated with therapeutic protein production pathways, in order to unravel the biological drivers and disentangle the uncharacterized genetic architecture responsible for optimizing therapeutic protein production in CHO cells.

26 Claims, 10 Drawing Sheets

Specification includes a Sequence Listing.

(56) References Cited

OTHER PUBLICATIONS

Engler, Carola, et al., "A One Pot, One Step, Precision Cloning Method with High Throughput Capability." PLOS One (Nov. 2008); 3.11: e3647, pp. 1-7. Epub Nov. 5, 2008.
Fischer, et al., "The art of CHO cell engineering: A comprehensive retrospect and future perspectives." Biotechnology Advances (2015); 33(8): 1878-1896.
Fox, et al. "Improving catalytic function by ProSAR-driven enzyme evolution." Nature Biotechnology (Feb. 18, 2007); 25(3): 338-344.
Gibson, et al., "Enzymatic assembly of DNA molecules up to several hundred kilobases." Nature Methods (Apr. 12, 2009); 6(5): 343-345.
Hong, et al., "Cloning and functional expression of thermostable βp-glucosidase gene from Thermoascus aurantiacus." Applied Microbiology and Biotechnology (2007); 73(6): 1331-1339.
Hunkapiller, et al., "Immunology: The growing immunoglobulin gene superfamily." Nature (1986); 323: 15-16.
Huston, et al. "Protein engineering of antibody binding sites: recovery of specific activity in an anti-digoxin single-chain Fv analogue produced in *Escherichia coli*." Proc Natl Acad Sci U S A. (1988); 85(16): 5879-5883.
Jones, et al., "High level expression of introduced chimaeric genes in regenerated transformed plants." The EMBO Journal (Oct. 4, 1985); 4(10): 2411-2418.
Kashyap, et al., "Big data analytics in bioinformatics: A machine learning perspective." Journal of Latex Class Files (2014); 13(9): 20 pages.
Kim, et al., "Polony multiplex analysis of gene expression (PMAGE) in mouse hypertrophic cardiomyopathy." Science (Jun. 8, 2007); 316(5830): 1481-1484.
Kotera and Nagai, "A high-throughput and single-tube recombination of crude PCR products using a DNA polymerase inhibitor and type IIS restriction enzyme." Journal of Biotechnology (Oct. 10, 2008); 137.1: 1-7. Epub Jul. 23, 2005.
Kozlov, et al., "Significant improvement of quality for long oligonucleotides by using controlled pore glass with large pores." Nucleosides, Nucleotides and Nucleic Acids (2005); 24(5-7): 1037-1041.
Krämer, et al., "Methods in mammalian cell line engineering: from random mutagenesis to sequence-specific approaches". Appl Microbiol Biotechnol (Sep. 2010); 88(2): 425-436. Epub Aug. 6, 2010.
Kuo, et al., "The emerging role of systems biology for engineering protein production in CHO cells." Current Opinion in Biotechnology (Jun. 2018); 51: 64-69. Epub Dec. 7, 2017.
Lanzavecchia, et al., "The use of hybrid hybridomas to target human cytotoxic T lymphocytes". Eur J Immunol. (1986); 17(1): 105-111.
Lee, et al., "Site-specific integration in CHO cells mediated by CRISPR/Cas9 and homology-directed DNA repair pathway". Scientific Reports (Feb. 15, 2018); 5, Article No. 8572, pp. 1-11.
Leng and Müller, "Classification using functional data analysis for temporal gene expression data." Bioinformatics (Jan. 1, 20006); 22(1): 68-76. Epub Oct. 27, 2005.
Libbrecht and Noble, "Machine learning applications in genetics and genomics." Nature Reviews Genetics (Jun. 2015); 16(6): 321-332. Epub May 7, 2015.
Margulies, et al., "Genome sequencing in microfabricated high-density picolitre reactors." Nature (Sep. 15, 2005); 437(7057): 376-380. Epub Jul. 31, 2005.
Moore, J.C., et al., "Strategies for the in vitro evolution of protein function: enzyme evolution by random recombination of improved sequences." Journal of Molecular Biology (Sep. 26, 1997); 272(3)3: 336-347.
Paek, et al., "Development of rapid one-step immunochromatographic assay." Methods (Sep. 2000); 22(1): 53-60.
Parry, et al., "Biochemical characterization and mechanism of action of a thermostable β-glucosidase purified from Thermoascus aurantiacus." Biochemical Journal (2001); 353(1): 117-127.
Prompramote, et al. "Machine learning in bioinformatics." Bioinformatics Technologies. Springer Berlin Heidelberg (2005); pp. 117-153.
Ricciardelli, et al., "Development and characterization of primary cultures of smooth muscle cells from the fibromuscular stroma of the guinea pig prostate." In Vitro Cellular & Developmental Biology (Nov. 1989); 25(11): 1016-1024.
Shevade, et al. "A simple and efficient algorithm for gene selection using sparse logistic regression." Bioinformatics (Nov. 22, 2003); 19(17): 2246-2253.
Sierzchala, et al., "Solid-Phase Oligodeoxynucleotide Synthesis: A Two-Step Cycle Using Peroxy Anion Deprotection" J. Am. Chem. Soc. 2003, 125, 44, 13427-13441.
Stemmer, W.P., "DNA shuffling by random fragmentation and reassembly: In vitro recombination for molecular evolution." Proceedings of the National Academy of Sciences (Oct. 25, 1994); 91(22): 10747-10751.
Stemmer, W.P., "Rapid evolution of a protein in vitro by DNA shuffling." Nature (Aug. 4, 1994); 370(6488): 389-391.
Tian, et al., "Advancing high-throughput gene synthesis technology." Molecular BioSystems (Jul. 2009); 5(7): 714-722. Epub Apr. 6, 2009.
Weber, et al., "Assembly of designer TAL effectors by Golden Gate cloning." PLoS ONE (2011); 6.5: e19722, pp. 1-5. Epub May 19, 2011.
Zhang, et al. "Directed evolution of a fucosidase from a galactosidase by DNA shuffling and screening." Proc Natl Acad Sci U S A. (1997); 94 (9): 4504-4509.
PCT/US2019/023106, International Preliminary Report on Patentability dated Sep. 22, 2020, 5 pages.
PCT/US2019/023106, International Search Report and Written Opinion dated Jun. 6, 2019, 8 pages.

\* cited by examiner

HTP PLATFORM FOR THE GENETIC ENGINEERING OF CHINESE HAMSTER OVARY CELLS

CROSS-REFERENCE TO RELATED APPLICATIONS

This application is a Continuation of International PCT Application No. PCT/US2019/023106, filed Mar. 20, 2019, which claims the benefit of priority to U.S. Provisional Application No. 62/645,708, filed on Mar. 20, 2018, each of which is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ZYMR_024_01US_SeqList_ST25.txt. The text file is 98 KB, was created on Jul. 20, 2020, and is being submitted electronically via EFS-Web.

FIELD

The present disclosure is directed to a high-throughput (HTP) genomic engineering platform for improving the production of therapeutic proteins in CHO cells. The disclosed HTP genomic engineering platform is computationally driven and integrates molecular biology, automation, and advanced machine learning protocols.

BACKGROUND

Chinese hamster ovary (CHO) cells represent the most frequently applied host cell system for industrial manufacturing of recombinant protein therapeutics. CHO cells are capable of producing high quality biologics exhibiting human-like post-translational modifications in gram quantities. Given this, it is not surprising that therapeutic proteins produced in CHO cells are in very high demand. Consequently, to meet the ever-growing demand for effective, safe, and affordable protein therapeutics, decades of intense efforts have aimed to maximize the quantity and quality of recombinant proteins produced in CHO cells.

However, production processes for biopharmaceuticals using CHO cells still suffer from cellular limitations such as limited growth, low productivity, and stress resistance, as well as higher expenses compared to bacterial or yeast based expression systems. Recently, cell engineering efforts have improved product titer; however, uncharacterized cellular processes and gene regulatory mechanisms still hinder cell growth, specific productivity, and protein quality.

Thus, there is a great need in the art for new methods of engineering CHO cells for the production of human therapeutic proteins.

Particularly, there is an urgent need for methods of engineering CHO cells, which are able to unravel the biological drivers of protein production and disentangle the uncharacterized cellular processes and gene regulatory mechanisms that hinder cell growth, specific productivity, and protein quality.

SUMMARY OF THE DISCLOSURE

The present disclosure is directed to a high-throughput (HTP) genomic engineering platform for improving the production of therapeutic proteins in CHO cells.

The CHO cell genomic engineering platform described herein is based upon HTP genetic engineering toolsets, which do not rely upon knowledge of underlying genetic causal relationships. Consequently, the taught platform is able to explore the CHO genomic landscape in a genetically agnostic manner, in order to discover the underlying genetic architecture responsible for driving the pathways crucial for therapeutic protein production.

In particular aspects, the disclosure teaches a HTP promoter swap genomic engineering tool, which is useful for exploring the genetic pathways associated with therapeutic antibody production. The HTP promoter swap tool allows for the systematic perturbation of cellular pathway genes, which enables one to determine the effect that such perturbation has upon a gene of interest, e.g. a therapeutic protein such as an antibody. This HTP molecular tool can be coupled with an advanced machine learning protocol and HTP cell-build factory platform, which will enable the manufacturing of better CHO cell lines for the production of antibodies.

The versatility of the HTP promoter swap tool provides genomic engineers a systematic way to perturb and study CHO cell pathways and identify the effects of particular genes on therapeutic protein production.

The data garnered from utilizing the HTP promoter swap genomic engineering tool, in various "omics" pathways, will enable the development of large libraries of genomic information, which can then be utilized in advanced machine learning models to understand the genetic perturbations that are most likely to lead to better CHO cell therapeutic protein production. This information can be used with emerging genome editing technologies to rationally engineer CHO cells to further control the quantity, quality, and affordability of many biologics.

Thus, the taught platform utilizes both a rational and agnostic methodology to engineer better performing CHO cells. As an example, the HTP promoter swap genomic engineering tool may first be utilized within pathways considered to be most likely to contribute to desired therapeutic protein production characteristics. The information garnered from such a "rational improvement" campaign can be stored in genetic databases, which then form the basis for training data sets for advanced machine learning protocols. These machine-learning algorithms will be utilized to predict future target genes that may be important to perturb, and which could not be determined using a purely rationally designed improvement campaign.

Furthermore, the HTP promoter swap genomic engineering tool can be utilized in an initial "genetic pathway agnostic manner," in which genes not thought to be associated with therapeutic protein production are perturbed. This information, like the genetic information garnered from the aforementioned rational improvement campaign, can be stored in a database and utilized to train the machine learning algorithms.

In embodiments, the HTP genomic engineering methods of the present disclosure do not require prior genetic knowledge in order to achieve significant gains in host cell performance. Indeed, the present disclosure teaches methods of generating diversity pools via several functionally agnostic approaches, including: identification of genetic diversity among pre-existing host cell variants (e.g., such as the comparison between genomes of sequenced CHO cell lines); and randomly targeting genes with the promoter swap tool, without preference to "known pathway" genes, in order to effectively "explore" the genomic space in a random fashion.

In some embodiments however, the present disclosure also teaches hypothesis-driven methods of designing genetic diversity that will be used for downstream HTP engineering. That is, in some embodiments, the present disclosure teaches the directed design of selected genetic alteration.

In an embodiment, a HTP method for improving immunoglobulin expression is provided, which comprises: a) providing a cellular pathway target gene endogenous to a host cell and a promoter ladder comprising a plurality of promoters exhibiting different expression profiles; b) engineering the genome of the host cell, to create an initial promoter swap host cell library comprising a plurality of host cells, wherein each cell comprises a different promoter from the promoter ladder operably linked to the target gene; and, c) screening cells of the initial promoter swap host cell library for phenotypic characteristics of an immunoglobulin of interest and/or the host cell. In another embodiment, a HTP method for improving immunoglobulin expression is provided, which comprises: a) providing a cellular pathway target gene endogenous to a host cell and a promoter ladder comprising a plurality of promoters exhibiting different expression profiles; b) engineering the genome of the host cell, to create an initial promoter swap host cell library comprising a plurality of host cells, wherein the plurality of host cells comprises individual host cells comprising a different promoter from the promoter ladder operably linked to the target gene; and, c) screening cells of the initial promoter swap host cell library for phenotypic characteristics of an immunoglobulin of interest and/or the host cell. In embodiments, the host cell is a mammalian cell, a murine cell, or a Chinese hamster ovary cell. In embodiments, the target gene encodes a molecule with a function selected from the group consisting of: secretion, protein transport, stress, glycosylation, apoptosis, unfolded protein response, protein folding (e.g. chaperones), ER-associated degradation, and metabolism. In embodiments, the target gene encodes a molecule selected from the group consisting of: signaling receptor protein 14 (SRP14), signaling receptor protein 9 (SRP9), signaling receptor protein 54 (SRP54), X-box-binding protein 1 (XBP-1), b-cell lymphoma 2 (bcl-2), insulin-like growth factor 1 (IGF1), C1GALT1-specific chaperone (COSMC), alpha-1,6-fucosyltransferase (FUT8), BCL2 antagonist/killer (BAK), activating transcription factor 6 (ATF6), eukaryotic translation initiation factor 2 alpha kinase 3 (PERK), inositol requiring enzyme 1 α (IRE1α), heat shock 70 kDa protein 5 (BiP/GRP78 (HSP70)), DNA heat shock protein family member B9 (Dnajb9 (ERdj4/HSP40)), and lactate dehydrogenase A (LDHA). In embodiments, the promoter ladder comprises at least two promoters selected from the group consisting of: CMV, EF1α, SV40, RSV, and PGK. In embodiments, the promoter ladder comprises at least two promoters with nucleotide sequences selected from the group consisting of: SEQ ID NOs 1-5. In embodiments, the immunoglobulin (Ig) is selected from the group consisting of: IgG, IgM, IgA, IgE, and IgD. In embodiments, the immunoglobulin is selected from the group consisting of: IgG1, IgG2, IgG3, and IgG4. In embodiments, engineering the genome of the host cell comprises utilizing a CRISPR compatible endonuclease and associated guide RNA (gRNA) to target and cleave the host cell genome upstream of the target gene. In some embodiments, the CRISPR compatible endonuclease is selected from Cas9, Cas12a, Cas12b, Cas12c, Cas12d, Cas12e, Cas13a, Cas13b, Cas13c, Cpf1, and MAD7, or homologs, orthologs, mutants, variants or modified versions thereof. In embodiments, engineering the genome of the host cell comprises utilizing a CRIPSR compatible endonuclease and associated gRNA to target and cleave the host cell genome upstream of the target gene and inserting a promoter from the promoter ladder via homologous recombination. In embodiments, screening cells of the initial promoter swap host cell library for phenotypic characteristics of an immunoglobulin of interest comprises ascertaining or characterizing: titer, N-terminal cleavage, and/or glycosylation patterns, of the immunoglobulin of interest. In embodiments, screening cells of the initial promoter swap host cell library for phenotypic characteristics of the host cell comprises ascertaining or characterizing: cell growth, cell viability pattern during cultivation, cell densities, and cell specific productivity of immunoglobulin produced per cell per day. In embodiments, more than one cellular pathway target gene is provided. In embodiments, steps a)-c) are repeated. In embodiments, the method further comprises: d) providing a subsequent plurality of host cells that each comprise a unique combination of genetic variation selected from the genetic variation present in at least two individual host cells screened in the preceding step, to thereby create a subsequent promoter swap host cell library. In embodiments, the method further comprises: d) providing a subsequent plurality of host cells that each comprise a unique combination of genetic variation selected from the genetic variation present in at least two individual host cells screened in the preceding step, to thereby create a subsequent promoter swap host cell library; and e) screening individual host cells of the subsequent promoter swap host cell library for phenotypic characteristics of an immunoglobulin of interest and/or the host cell. In embodiments, the method further comprises: d) providing a subsequent plurality of host cells that each comprise a unique combination of genetic variation selected from the genetic variation present in at least two individual host cells screened in the preceding step, to thereby create a subsequent promoter swap host cell library; e) screening individual host cells of the subsequent promoter swap host cell library for phenotypic characteristics of an immunoglobulin of interest and/or the host cell; and f) repeating steps d)-e) one or more times. In embodiments, a population of host cells, derived by the taught methods, are provided.

In some embodiments, a HTP method for improving expression of a product of interest is provided, which comprises: a) providing a cellular pathway target gene endogenous to a host cell and a promoter ladder comprising a plurality of promoters exhibiting different expression profiles; b) engineering the genome of the host cell, to create an initial promoter swap host cell library comprising a plurality of host cells, wherein each cell comprises a different promoter from the promoter ladder operably linked to the target gene; and c) screening cells of the initial promoter swap host cell library for phenotypic characteristics of a product of interest and/or the host cell. In embodiments, the product of interest is a protein. In other embodiments, a HTP method for improving expression of a product of interest is provided, which comprises: a) providing a cellular pathway target gene endogenous to a host cell and a promoter ladder comprising a plurality of promoters exhibiting different expression profiles; b) engineering the genome of the host cell, to create an initial promoter swap host cell library comprising a plurality of host cells, wherein the plurality of host cells comprises individual host cells comprising a different promoter from the promoter ladder operably linked to the target gene; and c) screening cells of the initial promoter swap host cell library for phenotypic characteristics of a product of interest and/or the host cell. In embodiments, the product of interest is a protein. In embodiments, engineering the genome of the host cell comprises utilizing a CRISPR compatible endonuclease and associated gRNA to target and cleave the host cell genome upstream of the target gene. In some embodiments, the CRISPR compatible endonuclease is selected from Cas9, Cas12a, Cas12b, Cas12c, Cas12d, Cas12e, Cas13a, Cas13b, Cas13c, Cpf1, and MAD7, or homologs, orthologs, mutants, variants or modified versions thereof. In embodiments, the product of interest is an immunoglobulin. In embodiments, the product of interest is an antibody. In embodiments, the product of interest is a biomolecule. In embodiments, the product of interest is an enzyme. In embodiments, the product of interest is not a protein.

BRIEF DESCRIPTION OF THE FIGURES

FIG. 7A—construct carries three markers. Marker 1 is outside the homologous region and is lost during targeted integration. It is used as a negative selection/screening marker against off-target integrations. Markers 2 and 3 would be retained upon successful integration at the target locus and maybe used separately for screening (fluorescent) and selection (antibiotic resistance) for rapid phenotypic analysis. FIG. 7B—construct carries only a negative selection/screening marker against off-target integrations. No positive markers are integrated at the target locus, allowing one to sequentially target multiple genes in a given strain. In the absence of positive markers more extensive genotyping can be used to isolate the correctly integrated clones. FIG. 7C—construct is similar to the construct in FIG. 7A with an additional feature of either FRT or LoxP recombination sites around the two positive markers 2 and 3. The presence of these recombination sites can be used to selectively loop-out the region within. This would allow one to recycle these markers and allow the sequential engineering of multiple target genes in a given strain.

DETAILED DESCRIPTION

Definitions

Figure 1:
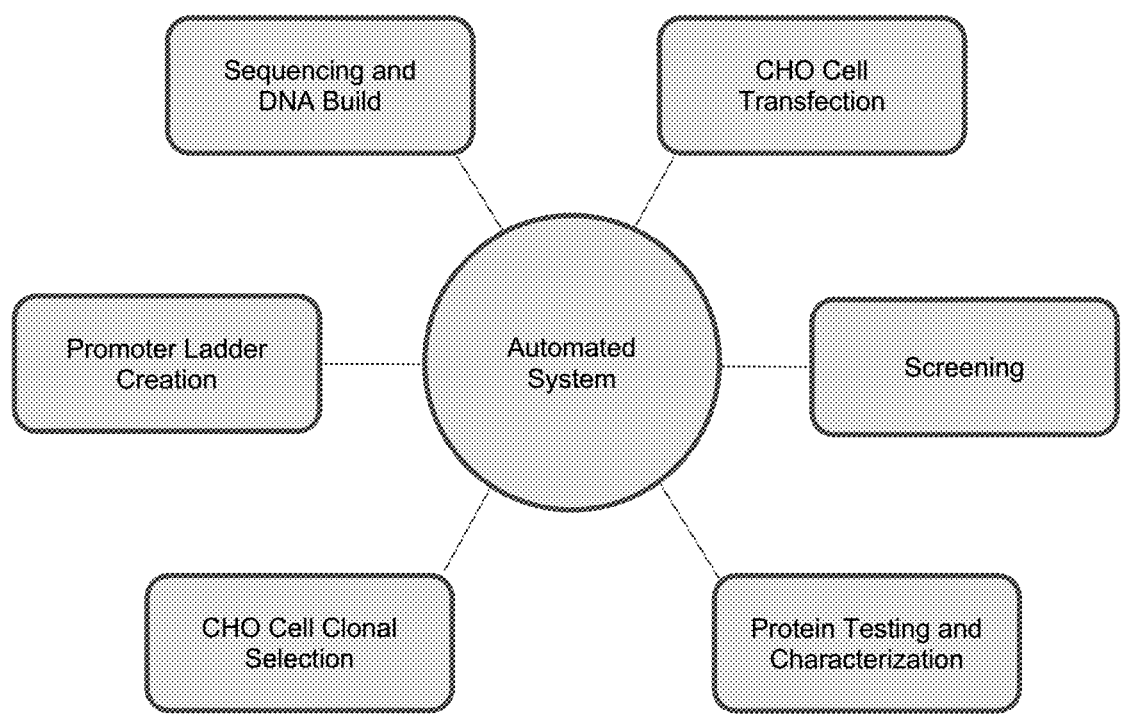
FIG. 1 depicts one embodiment of the automated system of the present disclosure. The present disclosure teaches use of automated robotic systems with various modules capable of promoter ladder creation, sequencing and building DNA, CHO cell transfection, screening, protein testing/characterization, and CHO cell clonal selection.

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "cellular organism" "microorganism" or "microbe" should be taken broadly. These terms are used interchangeably and include, but are not limited to, the two prokaryotic domains, Bacteria and Archaea, as well as certain eukaryotic fungi and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl)); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

"Host cells" in the meaning of the present disclosure may comprise any prokaryotic or eukaryotic cell. However, particular embodiments of the present disclosure focus upon eukaryotic cells. For example, "host cells" comprise hamster cells, such as BHK21, BHK TK−, CHO, CHO-K1, CHO-DUKX, CHO-DUKX B1, and CHO-DG44 cells, or the derivatives/progenies of any of such cell line. In a further embodiment of the present disclosure, host cells also comprise murine myeloma cells, e.g. NSO and Sp2/0 cells, or the derivatives/progenies of any of such cell line. Examples of murine and hamster cells which can be used in the meaning of this disclosure are also summarized in Table 1. However, derivatives/progenies of those cells, and other mammalian cells, including but not limited to: human, mice, rat, monkey, avian, or rodent cell lines, or non-mammalian eukaryotic cells, including but not limited to: yeast, insect, and plant cells, can also be used in the meaning of this disclosure, particularly for the production of biopharmaceutical and/or therapeutic proteins.

TABLE 1

Eukaryotic Production Cell Lines Useful for the Disclosure

| CELL LINE | ORDER/DEPOSIT NUMBER |
|---|---|
| NS0 | ECACC No. 85110503 |
| Sp2/0-Ag14 | ATCC CRL-1581 |
| BHK21 | ATCC CCL-10 |
| BHK TK− | ECACC No. 85011423 |
| HaK | ATCC CCL-15 |
| 2254-62.2 (BHK-21 derivative) | ATCC CRL-8544 |
| CHO | ECACC No. 8505302 |
| CHO wild type | ECACC 00102307 |
| CHO-K1 | ATCC CCL-61 |
| CHO-DUKX (CHO duk-, CHO/dhFr-) | ATCC CRL-9096 |
| CHO-DUKX B11 | ATCC CRL-9010 |
| CHO-DG44 | Urlaub et al., 1983 |
| CHO Pro-5 | ATCC CRL-1781 |
| V79 | ATCC CCC-93 |
| B 14AF28-G3 | ATCC CCL-14 |
| PER C6 | (Fallaux, F. J. et al, 1998) |
| HEK 293 | ATCC CRL-1573 |
| COS-7 | ATCC CRL-1651 |
| U266 | ATCC TIB-196 |
| HuNS1 | ATCC CRL-8644 |
| CHL | ECACC No. 87111906 |

Host cells can be established, adapted, and completely cultivated under serum free conditions, and optionally in media, which are free of any protein/peptide of animal origin. Commercially available media such as Ham's F 12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO—S-Invitrogen), serum-free CHO Medium (Sigma), and protein-free CHO Medium (Sigma) are exemplary appropriate nutrient solutions. Any of the media may be supplemented as necessary with a variety of compounds examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that would be known to those skilled in the art. In the present disclosure, serum free medium can be used in aspects. However, media supplemented with a suitable amount of serum can also be used for the cultivation of host cells. For the growth and selection of genetically modified cells expressing a selectable gene, a suitable selection agent can be added to the culture medium.

The terms "genetically modified host cell," "recombinant host cell," and "recombinant strain" are used interchangeably herein and refer to host cells that have been genetically modified by the cloning, transformation, transformation, or otherwise, methods of the present disclosure. Thus, the terms include a host cell (e.g., bacteria, yeast cell, fungal cell, CHO cell, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell.

The term "wild-type microorganism" or "wild-type host cell" describes a cell that occurs in nature, i.e. a cell that has not been genetically modified.

The term "genetically engineered" may refer to any manipulation of a host cell's genome (e.g. by insertion, deletion, mutation, or replacement of nucleic acids).

The term "control" or "control host cell" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment.

As used herein, the term "phenotype" refers to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribo- or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be inferred from results obtained using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "endogenous" or "endogenous gene," refers to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" refers to a substance coming from some source other than its native source.

For example, the terms "exogenous protein," or "exogenous gene" refer to a protein or gene from a non-native source, and that have been artificially supplied to a biological system.

As used herein, the term "heterologous" refers to a substance coming from some source or location other than its native source or location. For example, the term "heterologous promoter" may refer to a promoter that has been taken from one source organism and utilized in another organism, in which the promoter is not naturally found. However, the term "heterologous promoter" may also refer to a promoter that is from within the same source organism, but has merely been moved to a novel location, in which said promoter is not normally located.

Heterologous gene sequences can be introduced into a target cell by using an "expression vector," which can be a eukaryotic expression vector, for example a mammalian expression vector. Methods used to construct vectors are well known to a person skilled in the art and described in various publications. In particular techniques for constructing suitable vectors, including a description of the functional components such as promoters, enhancers, termination and polyadenylation signals, selection markers, origins of replication, and splicing signals, are reviewed in the prior art. Vectors may include but are not limited to plasmid vectors, phagemids, cosmids, artificial/mini-chromosomes (e.g. ACE), or viral vectors such as baculovirus, retrovirus, adenovirus, adeno-associated virus, herpes simplex virus, retroviruses, bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif. In one embodiment the expression vector comprises at least one nucleic acid sequence which is a regulatory sequence necessary for transcription and translation of nucleotide sequences that encode for a peptide/polypeptide/protein of interest.

The term "expression" as used herein refers to transcription and/or translation of a heterologous nucleic acid sequence within a host cell. The level of expression of a desired product/protein of interest in a host cell may be determined on the basis of either the amount of corresponding mRNA that is present in the cell, or the amount of the desired polypeptide/protein of interest encoded by the selected sequence. For example, mRNA transcribed from a selected sequence can be quantitated by Northern blot hybridization, ribonuclease RNA protection, in situ hybridization to cellular RNA or by PCR. Proteins encoded by a selected sequence can be quantitated by various methods, e.g. by ELISA, by Western blotting, by radioimmunoassays, by immunoprecipitation, by assaying for the biological activity of the protein, by immunostaining of the protein followed by FACS analysis or by homogeneous time-resolved fluorescence (HTRF) assays.

"Transfection" of eukaryotic host cells with a polynucleotide or expression vector, resulting in genetically modified cells or transgenic cells, can be performed by any method well known in the art. Transfection methods include, but are not limited to: liposome-mediated transfection, calcium phosphate co-precipitation, electroporation, polycation (such as DEAE-dextran)-mediated transfection, protoplast fusion, viral infections, and microinjection. In aspects, it is desirable that the transfection is a stable transfection. The transfection method that provides optimal transfection frequency and expression of the heterologous genes in the particular host cell line and type is favored. Suitable methods can be determined by routine procedures. For stable transfectants the constructs are either integrated into the host cell's genome or an artificial chromosome/mini-chromosome or located episomally so as to be stably maintained within the host cell.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

The term "protein" is used interchangeably with polypeptide and refers to polymers of amino acids of any length. These terms also include proteins that are post-translationally modified through reactions that include, but are not limited to: glycosylation, acetylation, phosphorylation, or protein processing. Modifications and changes, for example: fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with like properties. Generally, proteins are defined by amino acid length and are longer than polypeptides. The term "polypeptide" means a sequence with more than 10 amino acids and the term "peptide" means sequences up to 10 amino acids length.

The present disclosure is suitable to generate host cells for the production of biopharmaceutical polypeptides/proteins. The disclosure is particularly suitable for the high-yield expression of a large number of different genes of interest by cells showing an enhanced cell productivity.

"Gene of interest" (GOI), "selected sequence," or "product gene" have the same meaning herein and refer to a polynucleotide sequence of any length that encodes a product of interest or "protein of interest," also mentioned by the term "desired product." The selected sequence can be full length or a truncated gene, a fusion or tagged gene, and can be a cDNA, a genomic DNA, or a DNA fragment, preferably, a cDNA. It can be the native sequence, i.e. naturally occurring form(s), or can be mutated or otherwise modified as desired. These modifications include codon optimizations to optimize codon usage in the selected host cell, humanization, or tagging. The selected sequence can encode a secreted, cytoplasmic, nuclear, membrane bound, or cell surface polypeptide.

The "protein of interest" may include any protein, polypeptide, fragment thereof, or peptide, which can be expressed in the selected host cell. Desired proteins can be, for example: antibodies, enzymes, cytokines, lymphokines, adhesion molecules, receptors, derivatives or fragments thereof, polypeptides that can serve as agonists or antagonists, and/or any protein having therapeutic or diagnostic use. In the case of more complex molecules such as monoclonal antibodies, the GOI encodes one or both of the two antibody chains. A "product of interest" may be any desired molecule (protein or otherwise) that is producible in a host cell.

Further examples of "proteins of interest" or "desired proteins" include: insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1 and VEGF. Also included is the production of erythropoietin or any other hormone growth factors. The method according to the disclosure can also be advantageously used for production of antibodies or fragments thereof. Such fragments include e.g. Fab fragments (Fragment antigen-binding=Fab). Fab fragments consist of the variable regions of both chains which are held together by the adjacent constant region. These may be formed by protease digestion, e.g. with papain, from conventional antibodies, but similar Fab fragments may also be produced in the meantime by genetic engineering. Further antibody fragments include F(ab')2 fragments, which may be prepared by proteolytic cleaving with pepsin. The protein of interest may be recovered from the culture medium as a secreted polypeptide, or it can be recovered from host cell lysates if expressed without a secretory signal.

It may be necessary to purify the protein of interest from other recombinant proteins and host cell proteins in a way that substantially homogenous preparations of the protein of interest are obtained. As a first step, cells and/or particulate cell debris are removed from the culture medium or lysate. The product of interest thereafter is purified from contaminant soluble proteins, polypeptides and nucleic acids, for example, by fractionation on immune affinity or ion exchange columns, ethanol precipitation, reverse phase HPLC, Sephadex chromatography, chromatography on silica or on a cation exchange resin such as DEAE. In general, methods teaching a skilled person how to purify a protein heterologously expressed by host cells, are well known in the art.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilized. It is advantageous to link the variable regions of the heavy and of the light chain by a short peptide fragment, e.g. of 10 to 30 amino acids, e.g. 15 amino acids. In this way a single peptide strand is obtained consisting of VH and VL, linked by a peptide linker. An antibody protein of this kind is known as a single-chain-Fv (scFv). Examples of scFv antibody proteins of this kind known from the art.

In recent years, various strategies have been developed for preparing scFv as a multimeric derivative. This is intended to lead, in particular, to recombinant antibodies with improved pharmacokinetic and biodistribution properties, as well as with increased binding avidity. In order to achieve multimerisation of the scFv, scFv are prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative. The shortening of the Linker in an scFv molecule to 5-10 amino acids leads to the formation of homodimers in which an inter-chain VH/VL-superimposition takes place. Diabodies may additionally be stabilized is by the incorporation of disulphide bridges. Examples of diabody-antibody proteins are known in the art.

By minibody the skilled person means a bivalent, homodimeric scFv derivative. It consists of a fusion protein which contains the CH3 region of an immunoglobulin, preferably IgG, most preferably IgG1 as the dimerization region, which is connected to the scFv via a Hinge region (e.g. also from IgG1) and a Linker region. Examples of minibody-antibody proteins are known in the art.

By triabody the skilled person means a trivalent homotrimeric scFv derivative. ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-,tri- or tetrameric coiled coil structures.

The person skilled in the art will also be familiar with polypeptide molecules which consist of one or more variable domains of the single-chain antibody derived from lamas or other animals from the family of camelidae. Furthermore, the person skilled in the art is aware of derivatives and variants of such camelidae antibodies. Such molecules are also referred to as "domain antibodies". Domain antibody variants include several of those variable domains which are covalently connected by a peptide linker. To increase serum half-life, domain antibodies can be generated which are fused to a polypeptide moiety such as an antibody Fc-part or another protein present in the blood serum such as albumin.

By "scaffold proteins" a skilled person means any functional domain of a protein that is coupled by genetic cloning or by co-translational processes with another protein or part of a protein that has another function.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual (3$^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" means in this context the sequential arrangement of the promoter polynucleotide according to the disclosure with a further oligo- or polynucleotide, resulting in transcription of said further polynucleotide.

The term "volumetric productivity" or "production rate" is defined as the amount of product formed per volume of medium per unit of time. Volumetric productivity can be reported in gram per liter per hour (g/L/h).

The term "specific productivity" is defined as the rate of formation of the product. Specific productivity is herein further defined as the specific productivity in gram product per gram of cell dry weight (CDW) per hour (g/g CDW/h). Using the relation of CDW to $OD_{600}$ for the given specific productivity can also be expressed as gram product per liter culture medium per optical density of the culture broth at 600 nm (OD) per hour (g/L/h/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product.

The term "titre" or "titer" is defined as the strength of a solution or the concentration of a substance in solution. For example, the titer of a product of interest (e.g. small molecule, protein, peptide, antibody, synthetic compound, fuel, alcohol, etc.) in a fermentation broth is described as g of product of interest in solution per liter of fermentation broth (g/L).

The term "total titer" is defined as the sum of all product of interest produced in a process, including but not limited to the product of interest in solution, the product of interest in gas phase if applicable, and any product of interest removed from the process and recovered relative to the initial volume in the process or the operating volume in the process As used herein, the term "HTP genetic design library" or "library" refers to collections of genetic perturbations according to the present disclosure. In some embodiments, the libraries of the present invention may manifest as i) a collection of sequence information in a database or other computer file, ii) a collection of genetic constructs encoding for the aforementioned series of genetic elements, or iii) host cells (e.g. CHO cells) comprising said genetic elements. In some embodiments, the libraries of the present disclosure may refer to collections of individual elements (e.g., collections of promoters for PRO swap libraries). In other embodiments, the libraries of the present disclosure may also refer to combinations of genetic elements, such as combinations of particular promoter::genes. In some embodiments, the libraries of the present disclosure further comprise meta data associated with the effects of applying each member of the library in host organisms. For example, a library as used herein can include a collection of promoter::gene sequence combinations, together with the resulting effect of those combinations on one or more phenotypes in a particular CHO cell, thus improving the future predictive value of using said combination in future promoter swaps CHO improvement campaigns.

As used herein, the term "SNP" refers to Small Nuclear Polymorphism(s). In some embodiments, SNPs of the present disclosure should be construed broadly, and include single nucleotide polymorphisms, sequence insertions, deletions, inversions, and other sequence replacements. As used herein, the term "non-synonymous" or non-synonymous SNPs refers to mutations that lead to coding changes in host cell proteins.

A "high-throughput (HTP)" method or a "high-throughput (HTP)" method of genomic engineering may involve the utilization of at least one piece of equipment that enables one to evaluate a relatively large number of experiments or conditions compared to a non-HTP method, for example, automated equipment (e.g. a liquid handler or plate handler machine) to carry out at least one step of said method.

Chinese Hamster Ovary Cells

CHO cells represent the most frequently used mammalian production host for therapeutic proteins due to several key advantages over other cell types such as: (i) a robust growth in chemically defined and serum-free suspension culture, (ii) a reasonable safety profile regarding human pathogenic virus replication, and (iii) the ability to express r-proteins with human-like post-translational modifications (Kim et al., 2012). Furthermore, one of the most important characteristics of the CHO cell system is the ease to generate engineered cell clones which are able to stably express a gene of interest (GOI) in sufficient yields and acceptable quality for human use. This can be achieved following either targeted gene insertion into the host cell genome via site-specific integration or random integration followed by gene amplification using the dihydrofolate reductase (DHFR) or glutamine synthetase (GS) systems (Durocher and Butler, 2009; Kramer et al., 2010). However, since glycosylation patterns are not fully identical to that of humans, r-proteins derived from CHO cells were shown to be sometimes immunogenic (Butler and Spearman, 2014).

The entire "CHO cell system" encompasses a variety of different cell lines, which were likely all derived from a clonal and spontaneously immortalized Chinese hamster ovary cell originally isolated in 1956 by Theodore Puck (Puck et al., 1958). The fact that this first CHO cell and all subsequently derived cell lines are deficient in proline synthesis strongly supports the notion of a common clonal origin (Wurm and Hacker, 2011). Nowadays, three different CHO cell lines are commonly used for biopharmaceutical manufacturing: (i) the CHO-K1 cell line still harboring a functional DHFR gene, (ii) the CHO-DXB11 line with a mono-allelic DHFR knockout as well as (iii) the CHO-DG44 line, in which both DHFR alleles were physically deleted (Urlaub and Chasin, 1980; Urlaub et al., 1983; Wurm and Hacker, 2011).

In 2011, the first CHO genome was sequenced by Xu and coworkers from CHO-K1 cells, which significantly accelerated research efforts for biotechnological applications (Xu et al., 2011). However, since CHO cells are inherently prone to genomic rearrangements, further sequencing efforts including chromosome sorting in advance were necessary to get a more detailed overview on genomic landscapes (Brinkrolf et al., 2013; Lewis et al., 2013). In addition to genome information, transcriptome, miRnome as well as proteome/translatome data recently became available (Baycin-Hizal et al., 2012; Becker et al., 2011; Clarke et al., 2012; Courtes et al., 2013; Hackl et al., 2011). More recently, transcription start sites were unraveled (Jakobi et al., 2014), which gives rise to more detailed bioinformatics analyses once these start sites have eventually been introduced to the publically available CHO genome database (world wide web address: chogenome.org). Taken together, all these valuable contributions significantly helped to better characterize this biotechnological work horse and substantially supported research efforts in cellular engineering.

The aforementioned "Chinese Hamster Ovary Cells" section was taken substantially from: Fischer et al., "The art of CHO cell engineering: A comprehensive retrospect and future perspectives," Biotechnology Advances, Vol. 33, (2015), pgs. 1878-1896, which is herein incorporated by reference in its entirety.

Traditional Methods of CHO Cell Strain Improvement

Traditional approaches to improving CHO cell performance for producing therapeutic proteins can be broken down into a few large categories, which will each be briefly discussed below.

A. Bioprocess and Transgene Expression Optimization

Bioprocess and transgene expression optimization has improved recombinant protein titer in CHO cells by ≈100-fold over the past few decades. This increase in volumetric yield has been primarily achieved through media optimization, clonal selection processes, expression vectors, genetic elements, bioprocess controls, and bioreactor design. Kuo et al., "The emerging role of systems biology for engineering protein production in CHO cells," Current Opinion in Biotechnology, Vol. 51, (2018), pgs. 64-69, which is herein incorporated by reference in its entirety.

B. Targeted Engineering of CHO Cells

1. Introduction of Genes

The stable genomic integration of beneficial genes to improve performance of mammalian production cell lines has been frequently exploited. Generally, once an advantageous GOI has been identified, its (usually codon optimized) complementary DNA (cDNA) lacking any intronic sequences is isolated and cloned into a mammalian expression vector. Following delivery of the plasmid DNA (pDNA), transfected cells are subjected to antibiotic selection pressure to generate cell pools having the plasmid DNA stably integrated into their genome. In order to ensure high expression levels of the GOI, its expression is mainly driven by strong viral or cellular promoters/enhancers, while the selective gene is normally controlled by weak promoters to increase the overall expression level. The selected cell culture represents a heterogeneous mixed pool of cells showing various extent of transgene overexpression resulting in phenotypic differences between individual cells. Therefore, single cell clones have to be established from the heterogeneous cell pools to obtain clones that exhibit a strong and stable engineered phenotype. See, Supra, Fischer et al. (2015) (internal citations omitted).

2. Gene Knock-Out

Apart from overexpressing advantageous GOIs to improve performance of CHO production cells, genomic knockouts of disadvantageous genes represent further promising strategies for host cell engineering. There are different ways to stably delete a gene from the genome or to switch-off its function, e.g. by chemical or radiation induced random mutagenesis or using precise genome editing approaches. Targeted genome engineering with high specificity has thus become superior to random mutagenesis, especially from a regulatory point-of-view. In this conjunction, current state-of-the-art technologies mainly comprise the use of zinc-finger nucleases (ZFNs), transcription activator-like effector nucleases (TALENs), meganucleases or the recently introduced Clustered Regularly Interspaced Short Palindromic Repeats (CRISPR/Cas9)(or Cpf1) system. See, Supra, Fischer et al. (2015) (internal citations omitted).

Historically, one of the most important genetic manipulations, which eventually paved the way for an economical utilization of CHO cells for biopharmaceutical manufacturing was the genomic deletion/inactivation of the dihydrofolate reductase (DHFR) gene. Although these manipulations were introduced by chemical mutagenesis and ionizing radiation, giving rise to different DHFR-deficient CHO sublines named DXB11 and DG44, respectively, they mark the starting point of the commercial exploitation of CHO cells in biotechnology. Later on, another gene amplification system was introduced based on the glutamine synthetase (GS) enzyme that can be inhibited by methionine sulfoximine (MSX), enabling the generation of high expressing recombinant CHO cells. The repertoire of CHO-GS cell factories suitable for metabolic selection and gene amplification was expanded by the generation of CHO-K1SV cells with genomic knock-out of the endogenous GS gene (CHO-GS). CHO-DXB11/DG44 and CHO-GS cells can be selected for stable transfectants in growth media lacking hypoxanthin/thymidine and L-glutamine, respectively, if cells were previously transfected with an expression vector encoding a transgene in combination with a functional DHFR or GS gene copy. More importantly, stably transfected cells can be subjected to gene amplification by exposing the cells to steadily increasing concentrations of the dihydrofolate analog methotrexate (MTX) (CHO-DXB11 and -DG44) or methionine sulfoximine (MSX) (CHO-GS). See, Supra, Fischer et al. (2015) (internal citations omitted).

C. RNAi-Mediated Gene Silencing

Since the discovery of RNA interference (RNAi) in *Caenorhabditis elegans* (*C. elegans*) gene silencing (also known as gene knock-down) using small double-stranded RNAs (dsRNAs), which are also termed small-interfering RNAs (siRNAs) has become a frequently applied technology in cell engineering. siRNAs are 20-25 base pair long dsRNA molecules exhibiting complete sequence complementarity to the target messenger RNA (mRNA). Exogenously delivered siRNAs are cleaved by the RNase-III enzyme DICER and loaded onto an Argonaute-2 (AGO2) protein, which constitutes the core of the RNA-induced silencing complex (RISC) in the cytoplasm. Notably, AGO2 represents the only AGO family protein exhibiting slicer activity, which leads to an immediate cleavage of the target mRNA once it has been bound by the siRNA. The thermodynamic stability at the 5'-terminus of the dsRNA determines which strand will be favored as guide strand. Although siRNAs for targeted gene silencing are artificial, recent studies have unraveled the presence of naturally occurring siRNAs in eukaryotic cells which are derived from endogenous elements such as transposons transcripts, repetitive sequences, long stem loop structures or sense-antisense transcripts. See, Supra, Fischer et al. (2015) (internal citations omitted).

D. miRNA Overexpression/Repression

In the past decades, genetic engineering of biopharmaceutical production cells was focused on the manipulation of single target genes. However, as changes in cellular phenotypes are most likely not the result of altering the expression of an individual gene but rather of a plethora of genes involved in the same or different pathways, it is conceivable that engineering of entire signaling pathways might improve phenotypic outcome. microRNAs have recently entered the field of CHO cell engineering as these endogenous small RNAs are capable of regulating entire cellular pathways. Interestingly, large numbers of miRNAs can actually regulate multiple different cellular pathways concomitantly in order to keep the cell in homeostasis. These properties make miRNAs very attractive molecular tools for next-generation host cell engineering in the future. However, a large number of miRNAs still have to be functionally evaluated in CHO cells, in order to characterize their phenotypic influence. In this conjunction, high-content functional miRNA screening approaches, as well as miRnome profiling studies will help to unravel novel target molecules to be used for CHO cell engineering. See, Supra, Fischer et al. (2015) (internal citations omitted).

Serious Hurdles Remain Despite CHO Cell Engineering Advances

The advances in CHO cell engineering elaborated upon above have provided powerful tools to enhance protein production. However, the synthesis and secretion of a single protein depends on the concerted function of hundreds or thousands of other proteins. Thus, truly effective engineering strategies may require multiple genetic changes to the host cell.

To achieve this, efforts have been made to comprehensively study the molecular changes that occur to enable high rates of protein secretion, thus shedding light on molecular and physiological factors making certain cells high producers. Omics data have been used extensively to study productive clones. For example, a differential proteomic analysis identified the up-regulation of glutathione biosynthesis and the down-regulation of DNA replication to be characteristic of high-producing CHO cells. Likewise, transcriptomic profiling of various CHO cell lines indicated that certain favorable metabolic and glycosylation patterns are associated with differential expression of key genes. Ribosome profiling and polysome profiling have also been used to quantify translation of recombinant proteins and the endogenous mRNA in antibody producing CHO cells. These and many additional studies, show that omics data have emerged as valuable assays that provide insights into which genes, proteins, and metabolites are associated with desired traits in protein production in CHO cells. Furthermore, they are helping to identify potential targets for cell engineering and bioprocess optimization for enhanced protein production. See, Supra, Kuo et al. (2018) (internal citations omitted).

HTP Tools and Assays are Needed to Explore the Omics Space

There is a need for the development of HTP genetic tools and assays, which can be used to explore the genomic landscape and make the most use of the aforementioned increases in CHO cell omics data. These HTP tools and assays will need to be customized and adapted to work within a larger data science and machine learning system, in order to make sense of the vast amount of biological data that will be generated.

The present disclosure provides such a HTP genetic tool, e.g. HTP promoter swap genomic engineering tool. This tool can be utilized to systematically target any particular gene in an identified pathway that is important for therapeutic protein production.

Furthermore, the tool has expanded utility in the fact that it can be used to modulate genes of unknown function, or genes not known to be associated with a particular therapeutic protein production pathway. The versatility of the HTP promoter swap tool provides genomic engineers a systematic way to perturb and study CHO cell pathways and identify the effects of particular genes on therapeutic protein production.

To this end, the present disclosure sets forth a unique HTP genomic engineering platform that is computationally driven and integrates molecular biology, automation, data analytics, and machine learning protocols. This integrative platform utilizes a suite of HTP molecular tool sets that are used to construct HTP genetic design libraries. These genetic design libraries will be elaborated upon below.

Furthermore, the HTP platform taught herein is able to identify, characterize, and quantify the effect that individual genetic changes have on CHO cell performance. This information, i.e. what effect does a given genetic change x have on host cell phenotype y (e.g., production of a therapeutic protein), is able to be generated and then stored in the HTP genetic design libraries discussed below. That is, sequence information for each genetic permutation, and its effect on the host cell phenotype are stored in one or more databases, and are available for subsequent analysis (e.g., epistasis mapping, as discussed below). The present disclosure also teaches methods of physically saving/storing valuable genetic permutations in the form of genetic insertion constructs, or in the form of one or more host cell organisms containing said genetic permutation (e.g., see CHO cell libraries discussed below.)

When one couples these HTP genetic design libraries into an iterative process that is integrated with a sophisticated data analytics and machine learning process, then a dramatically different methodology for improving CHO cells emerges. The taught HTP platform is able to systematically explore the CHO cell genetic landscape with a highly efficient and elegant HTP molecular tool, said genetic exploration enabling researchers to make the most use of the expanding set of omics data being generated in the CHO field. These and other advantages will become apparent with reference to the HTP molecular tool sets and the derived genetic design libraries discussed below.

Genetic Design & CHO Cell Engineering: A Systematic Combinatorial Approach to CHO Cell Improvement Utilizing a Suite of HTP Molecular Tools and HTP Genetic Design Libraries As aforementioned, the present disclosure provides a novel HTP platform and genetic design strategy for engineering CHO cells through iterative systematic introduction and removal of genetic changes across the CHO cell genome. The platform is supported by a suite of molecular tools, which enable the creation of HTP genetic design libraries and allow for the efficient implementation of genetic alterations into a given CHO cell.

The HTP genetic design libraries of the disclosure serve as sources of possible genetic alterations that may be introduced into a particular CHO cell genetic background. In this way, the HTP genetic design libraries are repositories of genetic diversity, or collections of genetic perturbations, which can be applied to the initial or further engineering of a given CHO line. Techniques for programming genetic designs for implementation to host cells are described in pending U.S. patent application Ser. No. 15/140,296, incorporated by reference in its entirety herein.

The HTP molecular tool sets utilized in this platform may include, inter alia: HTP promoter swap genomic engineering tool, also referred to herein as a "promoter swap" or "PRO Swap" or "PROSWAP" tool.

The HTP methods of the present disclosure also teach methods for directing the consolidation/combinatorial use of HTP tool sets, including Epistasis mapping protocols. As aforementioned, this suite of molecular tools, either in isolation or combination, enables the creation of HTP genetic design CHO cell libraries.

As will be demonstrated, utilization of the aforementioned HTP genetic design libraries in the context of the taught HTP CHO cell engineering platform enables the identification and consolidation of beneficial genetic perturbations, which are highly associated with therapeutic protein production, into a single CHO cell genetic background.

In some embodiments, the present disclosure differs from known CHO cell improvement approaches in that it analyzes the genome-wide combinatorial effect of genetic permutations across multiple disparate genomic regions, including expressed and non-expressed genetic elements, and uses gathered information (e.g., experimental results) to predict genetic combinations expected to produce CHO cell enhancements.

In some embodiments, the present disclosure teaches: i) CHO cells amenable to improvement via the disclosed platform, ii) generating CHO cell diversity pools for downstream analysis, iii) methods and hardware for high-throughput screening and sequencing of large CHO cell variant pools, iv) methods and hardware for machine learning computational analysis and prediction of synergistic effects of genome-wide mutations, and v) methods for high-throughput CHO cell engineering.

The HTP molecular tool set—which enables the creation of the various HTP genetic design libraries utilized in the CHO cell engineering platform—will now be discussed.

Promoter Swaps: A Molecular Tool for the Derivation of Promoter Swap CHO Cell Libraries In some embodiments, the present disclosure teaches methods of selecting promoters with optimal expression properties to produce beneficial effects on overall CHO cell phenotype (e.g., yield or productivity of a therapeutic protein).

For example, in some embodiments, the present disclosure teaches methods of identifying one or more promoters and/or generating variants of one or more promoters within a CHO cell, which exhibit a range of expression strengths (e.g. promoter ladders discussed infra), or superior regulatory properties (e.g., tighter regulatory control for selected genes). A particular combination of these identified and/or generated promoters can be grouped together as a promoter ladder, which is explained in more detail below.

The promoter ladder in question is then associated with a given gene of interest. Thus, if one has promoters $P_1$-$P_3$ (representing three promoters that have been identified and/or generated to exhibit a range of expression strengths, e.g. high>medium>low) and associates the promoter ladder with a single gene of interest in a CHO cell genetic background (i.e. genetically engineer a CHO cell with a given promoter operably linked to a given target gene), then the effect of each of the three promoters can be ascertained, by characterizing each of the engineered CHO cells resulting from each combinatorial effort, given that the engineered CHO cells have an otherwise identical genetic background except the particular promoter(s) associated with the target gene.

The resultant CHO cells that are engineered via this process form HTP genetic design libraries.

The HTP genetic design library can refer to the actual physical CHO cell collection that is formed via this process, with each member cell being representative of a given promoter operably linked to a particular target gene, in an otherwise identical genetic background, said library being termed a "promoter swap CHO cell library."

Furthermore, the HTP genetic design library can refer to the collection of genetic perturbations—in this case a given promoter x operably linked to a given gene y—said collection being termed a "promoter swap library."

Further, one can utilize the same promoter ladder comprising promoters $P_1$-$P_3$ to engineer CHO cells, wherein each of the three promoters is operably linked to 10 different gene targets. The result of this procedure would be 30 CHO cell lines that are otherwise assumed genetically identical, except for the particular promoters operably linked to a target gene of interest. These 30 cell lines could be appropriately screened and characterized and give rise to another HTP genetic design library.

The aforementioned example of three promoters and 10 target genes is merely illustrative, as the concept can be applied with any given number of promoters that have been grouped together based upon exhibition of a range of expression strengths and any given number of target genes.

Persons having skill in the art will also recognize the ability to operably link two or more promoters in front of any gene target. Thus, in some embodiments, the present disclosure teaches promoter swap libraries in which 1, 2, 3, or more, promoters from a promoter ladder are operably linked to one or more genes.

Figure 6:
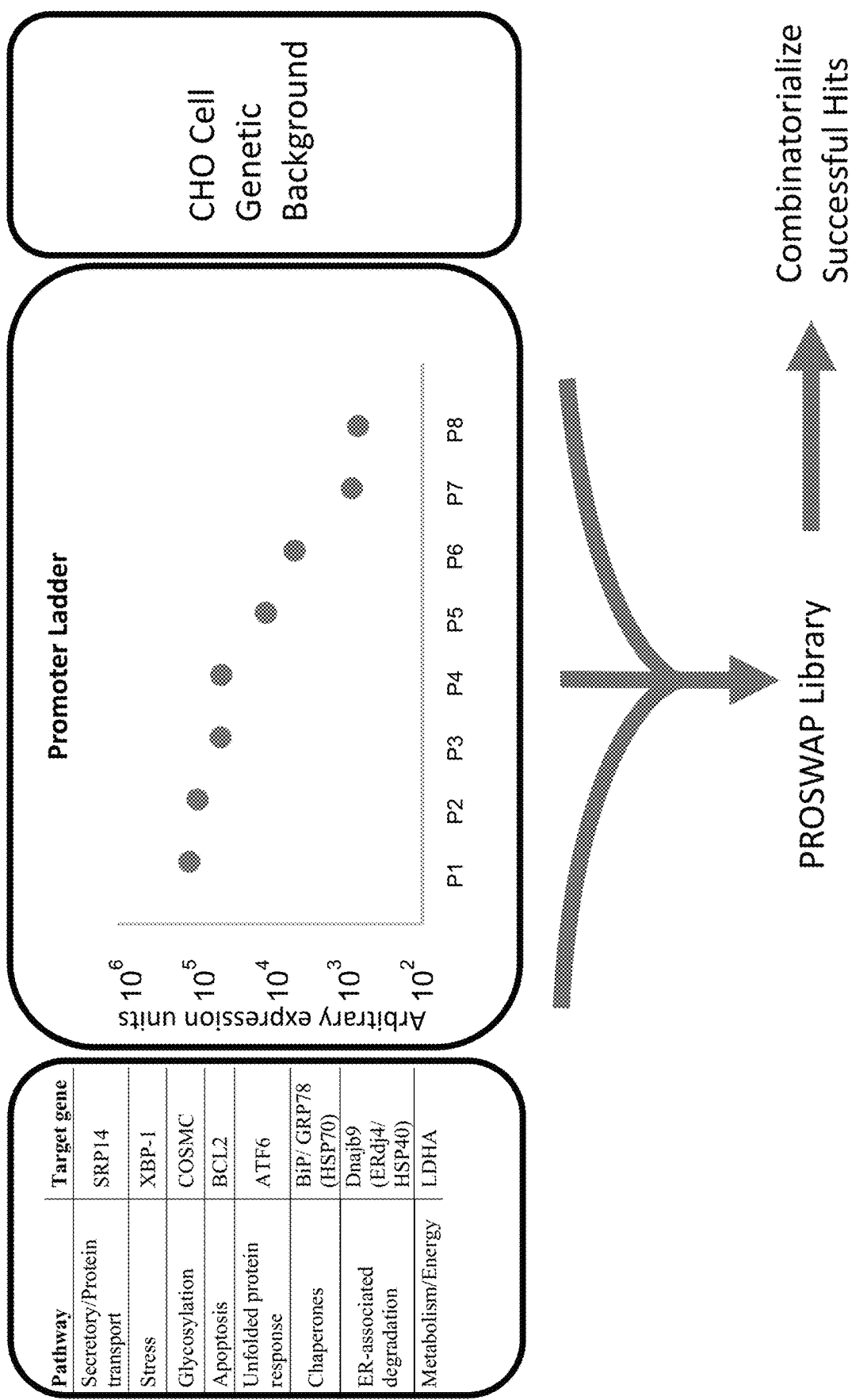
FIG. 6 illustrates an exemplary promoter library that is being utilized to conduct a promoter swap process for the identified gene targets. Promoters utilized in the PRO swap (i.e. promoter swap, or PROSWAP) process are depicted as a promoter ladder comprising $P_1$-$P_8$ ($P_1$ has the highest expression and $P_8$ has the lowest expression). However, any number of promoters could be utilized as the promoter ladder, so long as there is a range of expression strength. The $P_1$-$P_8$ promoter ladder is for illustration purposes to convey the utility of a range of expression strengths across the promoter ladder. The promoter ladder may comprise a high>medium>low ladder arrangement comprising three promoters.

The size of the promoter ladder can be any range. The promoter ladder merely needs to have a quantifiable range of expression strengths. Thus, a three promoter ladder having a high>medium>low design is merely exemplary. One could have two promoters, three promoters, four promoters, five promoters, six promoters, seven promoters, eight promoters, nine promoters, 10 promoters, or more, in the promoter ladder. FIG. 6 illustrates a hypothetical promoter ladder comprising eight promoters that could be utilized in front of each of the listed target genes in the figure.

The characterization of the CHO cell lines in the HTP genetic design library produces information and data that can be stored in any data storage construct, including a relational database, an object-oriented database, or a highly distributed NoSQL database. This data/information could be, for example, a given promoter's (e.g. $P_1$-$P_n$) effect when operably linked to a given gene target. This data/information can also be the broader set of combinatorial effects that result from operably linking two or more of promoters (e.g. $P_1$-$P_n$) to a given gene target.

In summary, utilizing various promoters to drive expression of various genes in an organism is a powerful tool to optimize a trait of interest. The molecular tool of promoter swapping, developed by the inventors, uses a ladder of promoter sequences that have been demonstrated to vary expression of at least one locus under at least one condition. This ladder is then systematically applied to a group of genes in the organism using high-throughput genome engineering. This group of genes is determined to have a high likelihood of impacting the trait of interest based on any one of a number of methods. These could include selection based on known function, or impact on the trait of interest, or algorithmic selection based on previously determined beneficial genetic diversity. In some embodiments, the selection of genes can include all the genes in a given host. In other embodiments, the selection of genes can be a subset of all genes in a given host, chosen randomly.

And, as aforementioned, the selection of which gene to modulate with the HTP promoter swap genomic engineering tool can be selected based on any number of omics datasets.

The resultant HTP genetic design promoter swap CHO cell library of individual cells containing a promoter sequence linked to a gene is then assessed for performance in a high-throughput screening model, and promoter-gene linkages that lead to increased performance are determined and the information stored in a database.

As discussed, the collection of genetic perturbations (i.e. given promoter x operably linked to a given gene y) form a "promoter swap library," which can be utilized as a source of potential genetic alterations to be utilized in later CHO cell processing. Over time, as a greater set of genetic perturbations is implemented against a greater diversity of CHO cell backgrounds, each library becomes more powerful, as a corpus of experimentally confirmed data is built, which can be used to more precisely and predictably design targeted changes against any CHO cell background of interest, for the purpose of altering any phenotype of interest (e.g. production of various antibody classes).

Transcription levels of genes in an organism are a key point of control for affecting organism behavior. Transcription is tightly coupled to translation (protein expression), and which proteins are expressed in what quantities determines organism behavior. Cells express thousands of different types of proteins, and these proteins interact in numerous complex ways to create function. By varying the expression levels of a set of proteins systematically, function can be altered in ways that, because of complexity, are difficult to predict. Some alterations may increase performance, and so, coupled to a mechanism for assessing performance, this technique allows for the generation of organisms with improved function, e.g. CHO cells and therapeutic protein production.

In the context of a small molecule synthesis pathway, enzymes interact through their small molecule substrates and products in a linear or branched chain, starting with a substrate and ending with a small molecule of interest. Because these interactions are sequentially linked, this system exhibits distributed control, and increasing the expression of one enzyme can only increase pathway flux until another enzyme becomes rate limiting.

Metabolic Control Analysis (MCA) is a method for determining, from experimental data and first principles, which enzyme or enzymes are rate limiting. MCA is limited however, because it requires extensive experimentation after each expression level change to determine the new rate limiting enzyme.

Promoter swapping is advantageous in this context, because through the application of a promoter ladder to each enzyme in a pathway, the limiting enzyme is found, and the same thing can be done in subsequent rounds to find new enzymes that become rate limiting. Further, because the read-out on function is better production of the small molecule of interest, the experiment to determine which enzyme is limiting is the same as the engineering to increase production, thus shortening development time.

In some embodiments, the present disclosure teaches the application of PRO swap to genes encoding individual subunits of multi-unit enzymes. In yet other embodiments, the present disclosure teaches methods of applying PRO swap techniques to genes responsible for regulating individual enzymes, or whole biosynthetic pathways.

In some embodiments, the promoter swap tool of the present disclosure is used to identify optimum expression of a selected gene target.

In some embodiments, the goal of the promoter swap may be to increase expression of a target gene to reduce bottlenecks in a metabolic or genetic pathway.

In other embodiments, the goal of the promoter swap may be to reduce the expression of the target gene to avoid unnecessary energy expenditures in the host cell, when expression of said target gene is not required.

In the context of other cellular systems like transcription, transport, or signaling, various rational methods can be used to try and find out, a priori, which proteins are targets for expression change and what that change should be. These rational methods reduce the number of perturbations that must be tested to find one that improves performance, but they do so at significant cost. Gene deletion studies identify proteins whose presence is critical for a particular function, and important genes can then be over-expressed. Due to the complexity of protein interactions, this is often ineffective at increasing performance. Different types of models have been developed that attempt to describe, from first principles, transcription or signaling behavior as a function of protein levels in the cell. These models often suggest targets where expression changes might lead to different or improved function. The assumptions that underlie these models are simplistic and the parameters difficult to measure, so the predictions they make are often incorrect, especially for non-model organisms. With both gene deletion and modeling, the experiments required to determine how to affect a certain gene are different than the subsequent work to make the change that improves performance. Promoter swapping sidesteps these challenges, because the constructed CHO cell that highlights the importance of a particular perturbation is also, already, the improved CHO cell.

Thus, in particular embodiments, promoter swapping is a multi-step process comprising:

1. Selecting a set of "x" promoters to act as a "ladder." Ideally these promoters have been shown to lead to highly variable expression across multiple genomic loci, but the only requirement is that they perturb gene expression in some way, e.g. high, medium, and low gene expression.

2. Selecting a set of "n" genes to target. This set can be any gene in a pathway known to be important for a particular function. However, this can also be any genomic region, which includes genes of no known function. And includes "off-pathway" genes. The gene target could be selected based on an algorithm. For example, algorithmic selection based on epistatic interactions between previously generated perturbations can be used. Other selection criteria based on hypotheses regarding beneficial genes to target, or through random selection can be used. In other embodiments, the "n" targeted genes can comprise non-protein coding genes, including non-coding RNAs.

3. High-throughput CHO cell engineering to rapidly, and in some embodiments, in parallel carry out the following genetic modifications: When a native promoter exists in front of target gene n and its sequence is known, replace the native promoter with each of the x promoters in the ladder. When the native promoter does not exist, or its sequence is unknown, insert each of the x promoters in the ladder in front of gene n (see e.g., FIG. 6). In this way a "library" (also referred to as a HTP genetic design library) of CHO cells is constructed, wherein each member of the library is an instance of x promoter operably linked to n target, in an otherwise identical genetic context. As previously described, combinations of promoters can be inserted, extending the range of combinatorial possibilities upon which the library is constructed.

4. High-throughput screening of the library of CHO cells, in a context where their performance against one or more metrics is indicative of the performance that is being optimized.

This foundational process can be extended to provide further improvements in CHO cell performance by, inter alia: (1) Consolidating multiple beneficial perturbations into a single CHO genetic background, either one at a time in an interative process, or as multiple changes in a single step. Multiple perturbations can be either a specific set of defined changes or a partly randomized, combinatorial library of changes. For example, if the set of targets is every gene in a pathway, then sequential regeneration of the library of perturbations into an improved member or members of the previous library of cells can optimize the expression level of each gene in a pathway regardless of which genes are rate limiting at any given iteration; (2) Feeding the performance data resulting from the individual and combinatorial generation of the library into an algorithm that uses that data to predict an optimum set of perturbations based on the interaction of each perturbation; and (3) Implementing a combination of the above two approaches.

Promoter Swap Low Level Expression Variation

The molecular tool, or technique, discussed above is characterized as promoter swapping, but is not limited to promoters and can include other sequence changes that systematically vary the expression level of a set of targets.

Other methods for varying the expression level of a set of genes could include: a) removing the promoter entirely form a target gene; b) a ladder of ribosome binding sites (or Kozak sequences in eukaryotes); c) removing the ribosomal binding site; d) replacing the start codon; e) removing the start codon; f) attachment of various mRNA stabilizing or destabilizing sequences to the 5' or 3' end, or at any other location, of a transcript, g) attachment of various protein stabilizing or destabilizing sequences at any location in the protein.

Also, the utilization of gene knock-outs could be utilized to completely remove expression of a target gene. Thus, the "low expression" profile of the tool may include very little or "no expression."

Furthermore, the utilization of CRISPRi technology (or any type of silencing or interfering technology, e.g. RNAi) is contemplated to repress the expression of a target gene.

2. Epistasis Mapping—A Predictive Analytical Tool Enabling Beneficial Genetic Consolidations In some embodiments, the present disclosure teaches epistasis mapping methods for predicting and combining beneficial genetic alterations into a CHO host cell. The genetic alterations may be created by any of the aforementioned HTP molecular tool sets (e.g., promoter swaps) and the effect of those genetic alterations would be known from the characterization of the derived HTP genetic design cell libraries. Thus, as used herein, the term epistasis mapping includes methods of identifying combinations of genetic alterations (e.g., beneficial promoter/target gene associations) that are likely to yield increases in host performance.

In embodiments, the epistasis mapping methods of the present disclosure are based on the idea that the combination of beneficial genetic alterations from two different functional groups is more likely to improve host performance, as compared to a combination of genetic alterations from the same functional group. See, e.g., Costanzo, The Genetic Landscape of a Cell, Science, Vol. 327, Issue 5964, Jan. 22, 2010, pp. 425-431 (incorporated by reference herein in its entirety).

Genetic alterations from the same functional group are more likely to operate by the same mechanism, and are thus more likely to exhibit negative or neutral epistasis on overall host performance. In contrast, genetic alterations from different functional groups are more likely to operate by independent mechanisms, which can lead to improved host performance and in some instances synergistic effects.

Thus, in some embodiments, the present disclosure teaches methods of analyzing genetic alterations predicted to belong to different functional groups. In some embodiments, the functional group similarity is determined by computing the cosine similarity of genetic alteration interaction profiles (similar to a correlation coefficient). The present disclosure also illustrates comparing genetic alterations via a similarity matrix or dendrogram.

Thus, the epistasis mapping procedure provides a method for grouping and/or ranking a diversity of genetic alterations applied in one or more genetic backgrounds for the purposes of efficient and effective consolidations of said alterations into one or more genetic backgrounds.

In aspects, consolidation is performed with the objective of creating novel CHO cell lines, which are optimized for the production of target biomolecules. Through the taught epistasis mapping procedure, it is possible to identify functional groupings of genetic changes, and such functional groupings enable a consolidation strategy that minimizes undesirable epistatic effects.

As discussed previously, rational approaches to CHO cell genetic engineering are confounded by the underlying complexity of biology. Causal mechanisms are poorly understood, particularly when attempting to combine two or more changes that each has an observed beneficial effect. Sometimes such consolidations of genetic changes yield positive outcomes (measured by increases in desired phenotypic activity), although the net positive outcome may be lower than expected and in some cases higher than expected. In other instances, such combinations produce either net neutral effect or a net negative effect. This phenomenon is referred to as epistasis, and is one of the fundamental challenges to genetic engineering.

The present HTP genomic engineering platform solves many of the problems associated with traditional CHO cell genetic engineering approaches. The present HTP platform uses automation technologies to perform hundreds or thousands of genetic changes at once. In particular aspects, unlike the rational approaches described above, the disclosed HTP platform enables the parallel construction of thousands of CHO cell backgrounds to more effectively explore large subsets of the relevant genomic space. By trying "everything," in a systematic way, the present HTP platform sidesteps the difficulties induced by our limited biological understanding.

However, at the same time, the present HTP platform faces the problem of being fundamentally limited by the combinatorial explosive size of genomic space, and the effectiveness of computational techniques to interpret the generated data sets given the complexity of genetic interactions. Techniques are needed to explore subsets of vast combinatorial spaces in ways that maximize non-random selection of combinations that yield desired outcomes.

Somewhat similar HTP approaches have proved effective in the case of enzyme optimization. In this niche problem, a genomic sequence of interest (on the order of 1000 bases), encodes a protein chain with some complicated physical configuration. The precise configuration is determined by the collective electromagnetic interactions between its constituent atomic components. This combination of short genomic sequence and physically constrained folding problem lends itself specifically to greedy optimization strategies. That is, it is possible to individually mutate the sequence at every residue and shuffle the resulting mutants to effectively sample local sequence space at a resolution compatible with the Sequence Activity Response modeling.

However, for full genomic optimizations for biomolecules, such residue-centric approaches are insufficient for some important reasons. First, because of the exponential increase in relevant sequence space associated with genomic optimizations for biomolecules. Second, because of the added complexity of regulation, expression, and metabolic interactions in biomolecule synthesis. The present inventors have solved these problems via the taught epistasis mapping procedure.

The taught method for modeling epistatic interactions, between a collection of genetic changes, for the purposes of more efficient and effective consolidation of said genetic changes into one or more genetic backgrounds, is groundbreaking and highly needed in the art.

When describing the epistasis mapping procedure, the terms "more efficient" and "more effective" refers to the avoidance of undesirable epistatic interactions among consolidation CHO cells, with respect to particular phenotypic objectives.

Generating Genetic Diversity Pools for Utilization in the Genetic Design & HTP CHO Cell Engineering Platform In some embodiments, the methods of the present disclosure are characterized as genetic design. As used herein, the term genetic design refers to the reconstruction or alteration of a host organism's genome through the identification and selection of the most optimum variants of a particular gene, portion of a gene, promoter, stop codon, 5'UTR, 3'UTR, or other DNA sequence to design and create new superior host cells.

In some embodiments, a first step in the genetic design methods of the present disclosure is to obtain an initial genetic diversity pool population with a plurality of sequence variations from which a new host genome may be reconstructed.

In some embodiments, a subsequent step in the genetic design methods taught herein is to use one or more of the aforementioned HTP molecular tool sets (e.g. promoter swapping) to construct HTP genetic design libraries, which then function as drivers of the genomic engineering process, by providing libraries of particular genomic alterations for testing in a host cell.

Harnessing Diversity Pools from Existing CHO Cell Lines

In some embodiments, the present disclosure teaches methods for identifying the sequence diversity present among various different CHO cell lines. Therefore, a diversity pool can be a given number n of CHO cell lines utilized for analysis, with said cells' genomes representing the "diversity pool."

It is known that the various CHO cell lines in existence have different phenotypic properties. Thus, by sequencing the known CHO cell lines one could create an initial pool of CHO cell diversity based on these whole genome sequences.

Single Locus Mutations to Generate Diversity

In some embodiments, the present disclosure teaches genetically engineering CHO cell populations by introducing, deleting, or replacing selected portions of genomic DNA. Thus, in some embodiments, the present disclosure teaches methods for targeting genetic alterations to a specific locus. In other embodiments, the present disclosure teaches the use of gene editing technologies such as ZFNs, TAL-ENS, or CRISPR, to selectively edit target DNA regions.

In other embodiments, the present disclosure teaches altering selected DNA regions outside of the host organism, and then inserting the sequence back into the host organism. For example, in some embodiments, the present disclosure teaches altering/engineering native or synthetic promoters to produce a range of promoter variants with various expression properties (see promoter ladder infra). In other embodiments, the present disclosure is compatible with single gene optimization techniques, such as ProSAR (Fox et al. 2007. "Improving catalytic function by ProSAR-driven enzyme evolution." Nature Biotechnology Vol 25 (3) 338-343, incorporated by reference herein).

In some embodiments, the selected regions of DNA are produced in vitro via gene shuffling of natural variants, or shuffling with synthetic oligos, plasmid-plasmid recombination, virus plasmid recombination, virus-virus recombination. In other embodiments, the genomic regions are produced via error-prone PCR.

Promoter Ladders

Promoters regulate the rate at which genes are transcribed and can influence transcription in a variety of ways. Constitutive promoters, for example, direct the transcription of their associated genes at a constant rate regardless of the internal or external cellular conditions, while regulatable promoters increase or decrease the rate at which a gene is transcribed depending on the internal and/or the external cellular conditions, e.g. growth rate, temperature, responses to specific environmental chemicals, and the like. Promoters can be isolated from their normal cellular contexts and engineered to regulate the expression of virtually any gene, enabling the effective modification of cellular growth, product yield and/or other phenotypes of interest.

In some embodiments, the present disclosure teaches methods for producing promoter ladder libraries for use in downstream genetic design methods. For example, in some embodiments, the present disclosure teaches methods of identifying one or more promoters and/or generating variants of one or more promoters within a host cell, which exhibit a range of expression strengths, or superior regulatory properties. A particular combination of these identified and/or generated promoters can be grouped together as a promoter ladder, which is explained in more detail below.

In some embodiments, the present disclosure teaches the use of promoter ladders. In some embodiments, the promoter ladders of the present disclosure comprise promoters exhibiting a continuous range of expression profiles. For example, in some embodiments, promoter ladders are created by: identifying natural, native, or wild-type promoters that exhibit a range of expression strengths in response to a stimuli, or through constitutive expression. These identified promoters can be grouped together as a promoter ladder.

In other embodiments, the present disclosure teaches the creation of promoter ladders exhibiting a range of expression profiles across different conditions. For example, in some embodiments, the present disclosure teaches creating a ladder of promoters with expression peaks spread throughout the different stages of a fermentation. In other embodiments, the present disclosure teaches creating a ladder of promoters with different expression peak dynamics in response to a specific stimulus. Persons skilled in the art will recognize that the regulatory promoter ladders of the present disclosure can be representative of any one or more regulatory profiles.

In some embodiments, the promoter ladders of the present disclosure are designed to perturb gene expression in a predictable manner across a continuous range of responses. In some embodiments, the continuous nature of a promoter ladder confers CHO cell improvement programs with additional predictive power. For example, in some embodiments, swapping promoters of a selected metabolic pathway can produce a host cell performance curve, which identifies the most optimum expression ratio or profile; producing a CHO cell in which the targeted gene is no longer a limiting factor for a particular reaction or genetic cascade, while also avoiding unnecessary over expression or mis-expression under inappropriate circumstances.

In some embodiments, promoter ladders are created by: identifying natural, native, or wild-type promoters exhibiting the desired profiles. In other embodiments, the promoter ladders are created by mutating naturally occurring promoters to derive multiple mutated promoter sequences. Each of these mutated promoters is tested for effect on target gene expression. In some embodiments, the edited promoters are tested for expression activity across a variety of conditions, such that each promoter variant's activity is documented/characterized/annotated and stored in a database. The resulting edited promoter variants are subsequently organized into promoter ladders arranged based on the strength of their expression (e.g., with highly expressing variants near the top, and attenuated expression near the bottom, therefore leading to the term "ladder").

In some embodiments, the present disclosure teaches promoter ladders that are a combination of identified naturally occurring promoters and mutated variant promoters of the natural/native promoters.

In some embodiments, one or more of the aforementioned identified naturally occurring promoter sequences are chosen for gene editing. In embodiments, the promoters of the present disclosure are edited by synthesizing new promoter variants with the desired sequence.

In some embodiments, the promoter ladders are not based/derived upon promoter variants of a native promoter. Rather, in these embodiments, the promoter ladder is a compilation of heterologous promoters that have been chose to form the ladder based upon their range of expression strength.

A non-exhaustive list of the promoters of the present disclosure is provided in the below Table 2. Each of the promoter sequences can be referred to as a heterologous promoter or heterologous promoter polynucleotide.

TABLE 2

Selected promoter sequences of the present disclosure.

| SEQ ID No. | Promoter Name | Promoter Origin |
|---|---|---|
| 1 | CMV | cytomegalovirus immediate-early promoter |
| 2 | EF1α | human elongation factor 1α promoter |

TABLE 2-continued

Selected promoter sequences of the present disclosure.

| SEQ ID No. | Promoter Name | Promoter Origin |
|---|---|---|
| 3 | SV40 | simian virus 40 early promoter |
| 4 | RSV | rous sarcoma virus long terminal repeat promoter |
| 5 | PGK | mouse phosphoglycerate kinase 1 promoter |

Figure 9:
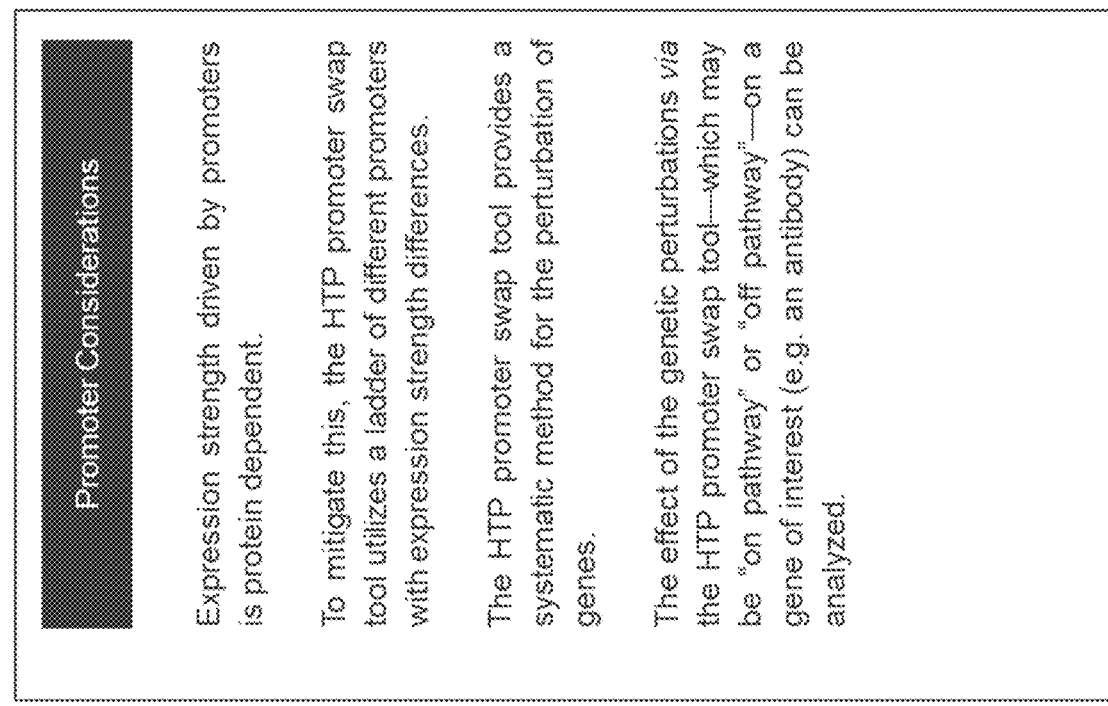
FIG. 9 illustrates an exemplary HTP promoter swap genomic engineering tool embodiment.
Figure 9:
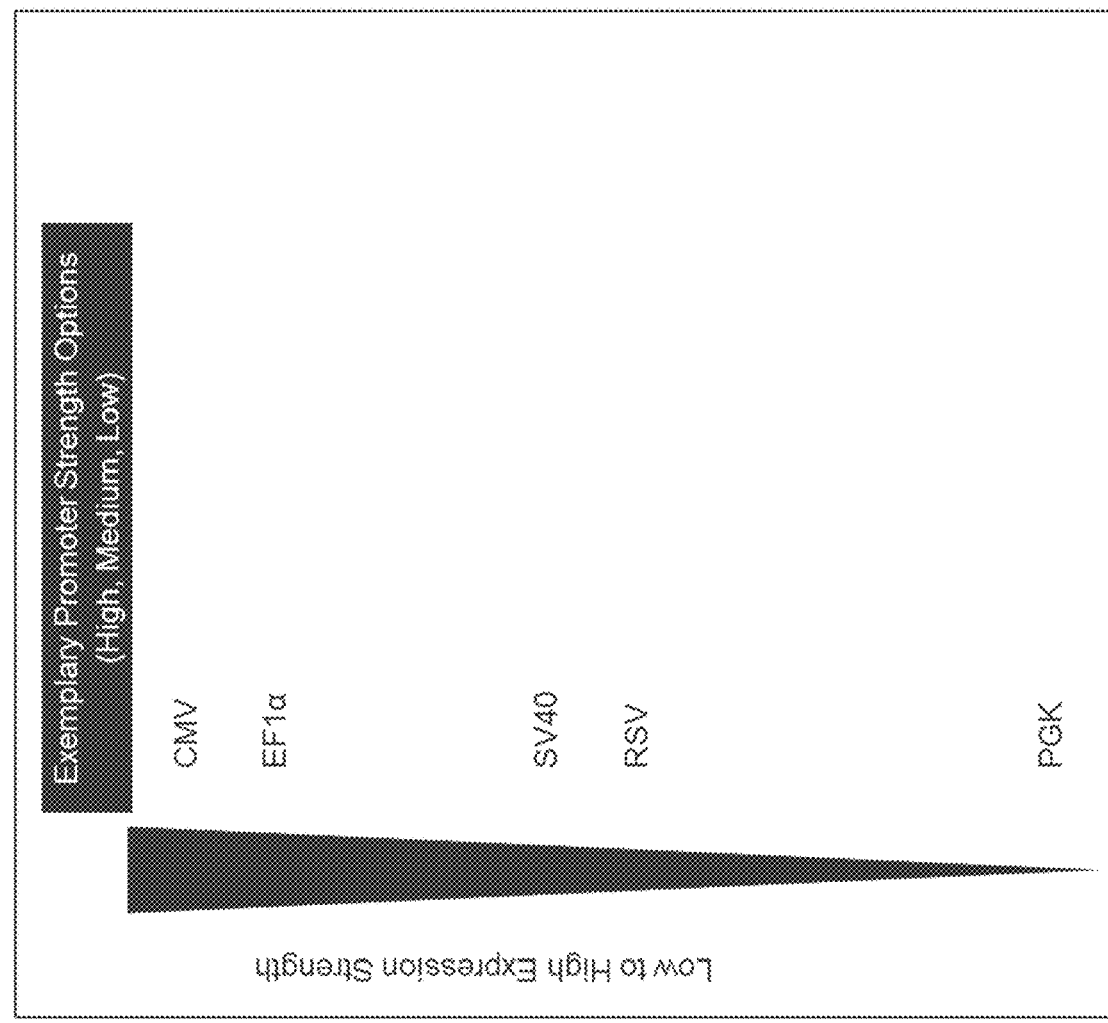

In Table 2, promoter PGK has the lowest expression strength; RSV and SV40 have a medium expression strength; and EF1α and CMV are the strongest promoters. Thus, these five promoters can be assembled into a promoter ladder based upon any combination. One would choose at least two of the promoters, such that a variable "ladder" of expression strength could be utilized. For a visual depiction, please see FIG. 9.

In some embodiments, the promoters of the present disclosure comprise nucleotide sequences which exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a promoter nucleotide sequence from the above table.

Hypothesis-Driven Diversity Pools and Hill Climbing

The HTP genomic engineering methods of the present disclosure do not require prior genetic knowledge in order to achieve significant gains in host cell performance. Indeed, the present disclosure teaches methods of generating diversity pools via several functionally agnostic approaches, including: identification of genetic diversity among pre-existing host cell variants (e.g., such as the comparison between genomes of sequenced CHO cell lines); and randomly targeting genes with the promoter swap tool, without preference to "known pathway" genes, in order to effectively "explore" the genomic space in a random fashion.

In some embodiments however, the present disclosure also teaches hypothesis-driven methods of designing genetic diversity that will be used for downstream HTP engineering. That is, in some embodiments, the present disclosure teaches the directed design of selected genetic alteration.

In some embodiments, the present disclosure teaches the creation of directed genetic alterations, or targeting with the promoter swap tool, based on gene annotation, hypothesized (or confirmed) gene function, or location within a genome. The diversity pools of the present disclosure may include creating genetic alterations in genes hypothesized to be involved in a specific metabolic or genetic pathway associated in the literature with increased performance of a host cell. In yet other embodiments, the diversity pool of the present disclosure may also include genetic alteration to genes based on algorithmic predicted function, or other gene annotation.

In some embodiments, the present disclosure teaches a "shell" based approach for prioritizing the targets of hypothesis-driven genetic alterations. The shell metaphor for genetic target prioritization is based on the hypothesis that only a handful of primary genes are responsible for most of a particular aspect of a host cell's performance (e.g., production of a single biomolecule). These primary genes are located at the core of the shell, followed by secondary effect genes in the second layer, tertiary effects in the third shell, and . . . etc. For example, in one embodiment the core of the shell might comprise genes encoding critical biosynthetic enzymes within a selected metabolic pathway. Genes located on the second shell might comprise genes encoding for other enzymes within the biosynthetic pathway responsible for product diversion or feedback signaling. Third tier genes under this illustrative metaphor would likely comprise regulatory genes responsible for modulating expression of the biosynthetic pathway.

The present disclosure also teaches "hill climb" methods for optimizing performance gains from every identified genetic alteration. In some embodiments, the present disclosure teaches that random, natural, or hypothesis-driven genetic alterations in HTP diversity libraries can result in the identification of genes associated with host cell performance. For example, the present methods may utilize the promoter swap tool to explore modulation of expression of a target gene that was not a priori thought to be involved with therapeutic protein production efficiency; however, upon utilizing the promoter swap tool and observing a favorable phenotypic effect, then the gene's importance can be analogized to the discovery of a performance "hill" in the combinatorial genetic space of an organism.

In some embodiments, the present disclosure teaches methods of exploring the combinatorial space around the identified hill. That is, in some embodiments, the present disclosure teaches the perturbation of the identified gene and associated regulatory sequences, in order to optimize performance gains obtained from that gene node (i.e., hill climbing).

The concept of hill climbing can also be expanded beyond the exploration of the combinatorial space surrounding a single gene sequence. In some embodiments, a genetic alteration in a specific gene might reveal the importance of a particular metabolic or genetic pathway to host cell performance.

Cell Culture and Fermentation

Cells of the present disclosure can be cultured in conventional nutrient media modified as appropriate for any desired biosynthetic reactions or selections. In some embodiments, the present disclosure teaches culture in inducing media for activating promoters. In some embodiments, the present disclosure teaches media with selection agents, including selection agents of transformants (e.g., antibiotics). In some embodiments, the present disclosure teaches growing cell cultures in media optimized for cell growth. In other embodiments, the present disclosure teaches growing cell cultures in media optimized for product yield. In some embodiments, the present disclosure teaches growing cultures in media capable of inducing cell growth and also contains the necessary precursors for final product production.

Culture conditions, such as temperature, pH and the like, are those suitable for use with the host cell selected for expression, and will be apparent to those skilled in the art. As noted, many references are available for the culture and production of many cells, including cells of bacterial, plant, animal (including mammalian) and archaebacterial origin. See e.g., Sambrook, Ausubel (all supra), as well as Berger, *Guide to Molecular Cloning Techniques, Methods in Enzymology* volume 152 Academic Press, Inc., San Diego, Calif.; and Freshney (1994) *Culture of Animal Cells, a Manual of Basic Technique*, third edition, Wiley-Liss, New York and the references cited therein; Doyle and Griffiths (1997) Mammalian Cell Culture: Essential Techniques John Wiley and Sons, NY; Humason (1979) *Animal Tissue Techniques, fourth edition* W.H. Freeman and Company; and Ricciardelle et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* from Sigma-Aldrich, Inc (St Louis, Mo.) ("Sigma-LSRCCC") and, for example, *The Plant Culture Catalogue* and supplement also from Sigma-Aldrich, Inc (St Louis, Mo.) ("Sigma-PCCS"), all of which are incorporated herein by reference.

Product Recovery and Quantification

Methods for screening for the production of products of interest are known to those of skill in the art and are discussed throughout the present specification. Such methods may be employed when screening the CHO cells of the disclosure.

In some embodiments, the present disclosure teaches methods of improving cells designed to produce non-secreted intracellular products. For example, the present disclosure teaches methods of improving the robustness, yield, efficiency, or overall desirability of cell cultures producing intracellular enzymes, oils, pharmaceuticals, or other valuable small molecules or peptides. The recovery or isolation of non-secreted intracellular products can be achieved by lysis and recovery techniques that are well known in the art, including those described herein.

For example, in some embodiments, cells of the present disclosure can be harvested by centrifugation, filtration, settling, or other method. Harvested cells are then disrupted by any convenient method, including freeze-thaw cycling, sonication, mechanical disruption, or use of cell lysing agents, or other methods, which are well known to those skilled in the art.

The resulting product of interest, e.g. a polypeptide, may be recovered/isolated and optionally purified by any of a number of methods known in the art. For example, a product polypeptide may be isolated from the nutrient medium by conventional procedures including, but not limited to: centrifugation, filtration, extraction, spray-drying, evaporation, chromatography (e.g., ion exchange, affinity, hydrophobic interaction, chromatofocusing, and size exclusion), or precipitation. Finally, high performance liquid chromatography (HPLC) can be employed in the final purification steps. (See for example Purification of intracellular protein as described in Parry et al., 2001, *Biochem.* 1353:117, and Hong et al., 2007, *Appl. Microbiol. Biotechnol.* 73:1331, both incorporated herein by reference).

In addition to the references noted supra, a variety of purification methods are well known in the art, including, for example, those set forth in: Sandana (1997) *Bioseparation of Proteins*, Academic Press, Inc.; Bollag et al. (1996) *Protein Methods, 2$^{nd}$ Edition*, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice 3$^{rd}$ Edition*, Springer Verlag, NY; Janson and Ryden (1998) *Protein Purification: Principles, High Resolution Methods and Applications*, Second Edition, Wiley-VCH, NY; and Walker (1998) *Protein Protocols on CD-ROM*, Humana Press, NJ, all of which are incorporated herein by reference.

In some embodiments, the present disclosure teaches the methods of improving cells designed to produce secreted products. For example, the present disclosure teaches methods of improving the robustness, yield, efficiency, or overall desirability of cell cultures producing valuable small molecules or peptides.

In some embodiments, immunological methods may be used to detect and/or purify secreted or non-secreted products produced by the cells of the present disclosure. In one example approach, antibody raised against a product molecule (e.g., against an insulin polypeptide or an immunogenic fragment thereof) using conventional methods is immobilized on beads, mixed with cell culture media under conditions in which the endoglucanase is bound, and precipitated. In some embodiments, the present disclosure teaches the use of enzyme-linked immunosorbent assays (ELISA).

In other related embodiments, immunochromatography is used, as disclosed in U.S. Pat. Nos. 5,591,645, 4,855,240, 4,435,504, 4,980,298, and Se-Hwan Paek, et al., "Development of rapid One-Step Immunochromatographic assay, Methods", 22, 53-60, 2000), each of which are incorporated by reference herein. A general immunochromatography detects a specimen by using two antibodies. A first antibody exists in a test solution or at a portion at an end of a test piece in an approximately rectangular shape made from a porous membrane, where the test solution is dropped. This antibody is labeled with latex particles or gold colloidal particles (this antibody will be called as a labeled antibody hereinafter). When the dropped test solution includes a specimen to be detected, the labeled antibody recognizes the specimen so as to be bonded with the specimen. A complex of the specimen and labeled antibody flows by capillarity toward an absorber, which is made from a filter paper and attached to an end opposite to the end having included the labeled antibody. During the flow, the complex of the specimen and labeled antibody is recognized and caught by a second antibody (it will be called as a tapping antibody hereinafter) existing at the middle of the porous membrane and, as a result of this, the complex appears at a detection part on the porous membrane as a visible signal and is detected.

In some embodiments, the screening methods of the present disclosure are based on photometric detection techniques (absorption, fluorescence). For example, in some embodiments, detection may be based on the presence of a fluorophore detector such as GFP bound to an antibody. In other embodiments, the photometric detection may be based on the accumulation on the desired product from the cell culture. In some embodiments, the product may be detectable via UV of the culture or extracts from said culture.

Persons having skill in the art will recognize that the methods of the present disclosure are compatible with host cells producing any desirable biomolecule product of interest.

Selection Criteria and Goals

The selection criteria applied to the methods of the present disclosure will vary with the specific goals of the cell improvement program. The present disclosure may be adapted to meet any program goals. For example, in some embodiments, the program goal may be to maximize the amount of therapeutic protein produced by a CHO cell.

Other goals may be more efficient production of a therapeutic protein. In some embodiments, the program goal may be to improve performance characteristics such as yield, titer, productivity, by-product elimination, tolerance to process excursions, optimal growth temperature and growth rate. In some embodiments, the program goal is improved host performance as measured by volumetric productivity, specific productivity, yield or titer, of a product of interest.

Sequencing

In some embodiments, the present disclosure teaches whole-genome sequencing of the organisms described herein. In other embodiments, the present disclosure also teaches sequencing of plasmids, PCR products, and other oligos as quality controls to the methods of the present disclosure. Sequencing methods for large and small projects are well known to those in the art.

In some embodiments, any high-throughput technique for sequencing nucleic acids can be used in the methods of the disclosure. In some embodiments, the present disclosure teaches whole genome sequencing. In other embodiments, the present disclosure teaches amplicon sequencing ultra-deep sequencing to identify genetic variations. In some embodiments, the present disclosure also teaches novel methods for library preparation, including tagmentation (see WO/2016/073690). DNA sequencing techniques include classic dideoxy sequencing reactions (Sanger method) using labeled terminators or primers and gel separation in slab or capillary; sequencing by synthesis using reversibly terminated labeled nucleotides, pyrosequencing; 454 sequencing; allele specific hybridization to a library of labeled oligonucleotide probes; sequencing by synthesis using allele specific hybridization to a library of labeled clones that is followed by ligation; real time monitoring of the incorporation of labeled nucleotides during a polymerization step; polony sequencing; and SOLiD sequencing.

In one aspect of the disclosure, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)).

In another embodiment, the methods of the present disclosure comprise amplifying the isolated molecules either before or after they are spatially isolated on a solid surface. Prior amplification may comprise emulsion-based amplification, such as emulsion PCR, or rolling circle amplification. Also taught is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081B1; which are incorporated by reference.

In one embodiment, individual molecules disposed and amplified on a solid surface form clusters in a density of at least $10^5$ clusters per $cm^2$; or in a density of at least $5 \times 10^5$ per $cm^2$; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

Computational Analysis and Prediction of Effects of Genome-Wide Genetic Design Criteria In some embodiments, the present disclosure teaches methods of predicting the effects of particular genetic alterations being incorporated into a given CHO cell background. In further aspects, the disclosure provides methods for generating proposed genetic alterations that should be incorporated into a given CHO cell, in order for said cell to possess a particular phenotypic trait. In given aspects, the disclosure provides predictive models that can be utilized to design novel host cells.

In some embodiments, the present disclosure teaches methods of analyzing the performance results of each round of screening and methods for generating new proposed genome-wide sequence modifications predicted to enhance host cell performance in the following round of screening.

In some embodiments, the present disclosure teaches that the system generates proposed sequence modifications to host cells based on previous screening results. In some embodiments, the recommendations of the present system are based on the results from the immediately preceding screening. In other embodiments, the recommendations of the present system are based on the cumulative results of one or more of the preceding screenings.

In some embodiments, the recommendations of the present system are based on previously developed HTP genetic design libraries. For example, in some embodiments, the present system is designed to save results from previous screenings, and apply those results to a different project, in the same or different CHO cell background.

In other embodiments, the recommendations of the present system are based on scientific insights. For example, in some embodiments, the recommendations are based on known properties of genes (from sources such as annotated gene databases and the relevant literature), codon optimization, transcriptional slippage, various "omics" data, or other hypothesis driven sequence and host optimizations.

In some embodiments, the proposed sequence modifications to a host cell recommended by the system, or predictive model, are carried out by the utilization of one or more of the disclosed molecular tools sets, for example: Promoter swaps or Epistasis mapping.

As alluded to in the epistatic mapping section, it is possible to estimate the performance (a.k.a. score) of a hypothetical CHO cell obtained by consolidating a collection of genetic alterations from a HTP genetic design library into a particular background via some preferred predictive model. Given such a predictive model, it is possible to score and rank all hypothetical CHO cells accessible via combinatorial consolidation.

Linear Regression to Characterize Built CHO Cells

Linear regression is an attractive method for the described HTP genomic engineering platform, because of the ease of implementation and interpretation. The resulting regression coefficients can be interpreted as the average increase or decrease in relative CHO cell performance attributable to the presence of each genetic change, e.g. each promoter:gene combo from a promoter swap campaign.

The taught method therefore uses linear regression models to describe/characterize and rank built CHO cells, which have various genetic perturbations introduced into their genomes from the various taught libraries.

Predictive Design Modeling

The linear regression model described above, which utilizes data from constructed CHO cells, can be used to make performance predictions for CHO cells that have not yet been built.

The procedure can be summarized as follows: generate in silico all possible configurations of genetic changes→use the regression model to predict relative cell performance→order the candidate cell designs by performance. Thus, by utilizing the regression model to predict the performance of as-yet-unbuilt cells, the method allows for the production of higher performing cells, while simultaneously conducting fewer experiments.

Generate Configurations

When constructing a model to predict performance of as-yet-unbuilt CHO cells, the first step is to produce a sequence of design candidates. This is done by fixing the total number of genetic changes in the cell, and then defining all possible combinations of genetic changes. For example, one can set the total number of potential genetic changes/perturbations and then decide to design all possible combinations of the potential genetic changes, which will result in candidate cell designs. One can calculate the number of non-redundant groupings of size r from n possible members using: $n!/((n-r)!*r!)$.

Predict Performance of New CHO Cell Designs

Using the linear regression constructed above with the combinatorial configurations as input, one can then predict the expected relative performance of each candidate design.

Predictive accuracy should increase over time as new observations are used to iteratively retrain and refit the model. The quality of model predictions can be assessed through several methods, including a correlation coefficient indicating the strength of association between the predicted and observed values, or the root-mean-square error, which is a measure of the average model error. Using a chosen metric for model evaluation, the system may define rules for when the model should be retrained.

A couple of unstated assumptions to the above model include: (1) there are no epistatic interactions; and (2) the genetic changes/perturbations utilized to build the predictive model were all made in the same background, as the proposed combinations of genetic changes.

Filtering for Second-Order Features

The above illustrative example focused on linear regression predictions based on predicted host cell performance. In some embodiments, the present linear regression methods can also be applied to non-biomolecule factors, such as saturation biomass, resistance, or other measurable host cell features. Thus, the methods of the present disclosure also teach considering other features outside of predicted performance when prioritizing the candidates to build. Assuming there is additional relevant data, nonlinear terms are also included in the regression model.

Diversity of Changes

When constructing the aforementioned models, one cannot be certain that genetic changes will truly be additive (as assumed by linear regression and mentioned as an assumption above) due to the presence of epistatic interactions. Therefore, knowledge of genetic change dissimilarity can be used to increase the likelihood of positive additivity. If one knows, for example, that the genetic changes from the top ranked CHO cell above are on the same metabolic pathway and have similar performance characteristics, then that information could be used to select another top ranking design with a dissimilar composition of changes. As described in the section above concerning epistasis mapping, the predicted best genetic changes may be filtered to restrict selection to genetic alterations with sufficiently dissimilar response profiles. Alternatively, the linear regression may be a weighted least squares regression using the similarity matrix to weight predictions.

Diversity of Predicted Performance

Finally, one may choose to design CHO cells with middling or poor predicted performance, in order to validate and subsequently improve the predictive models.

Iterative CHO Cell Design Optimization

Figure 4:
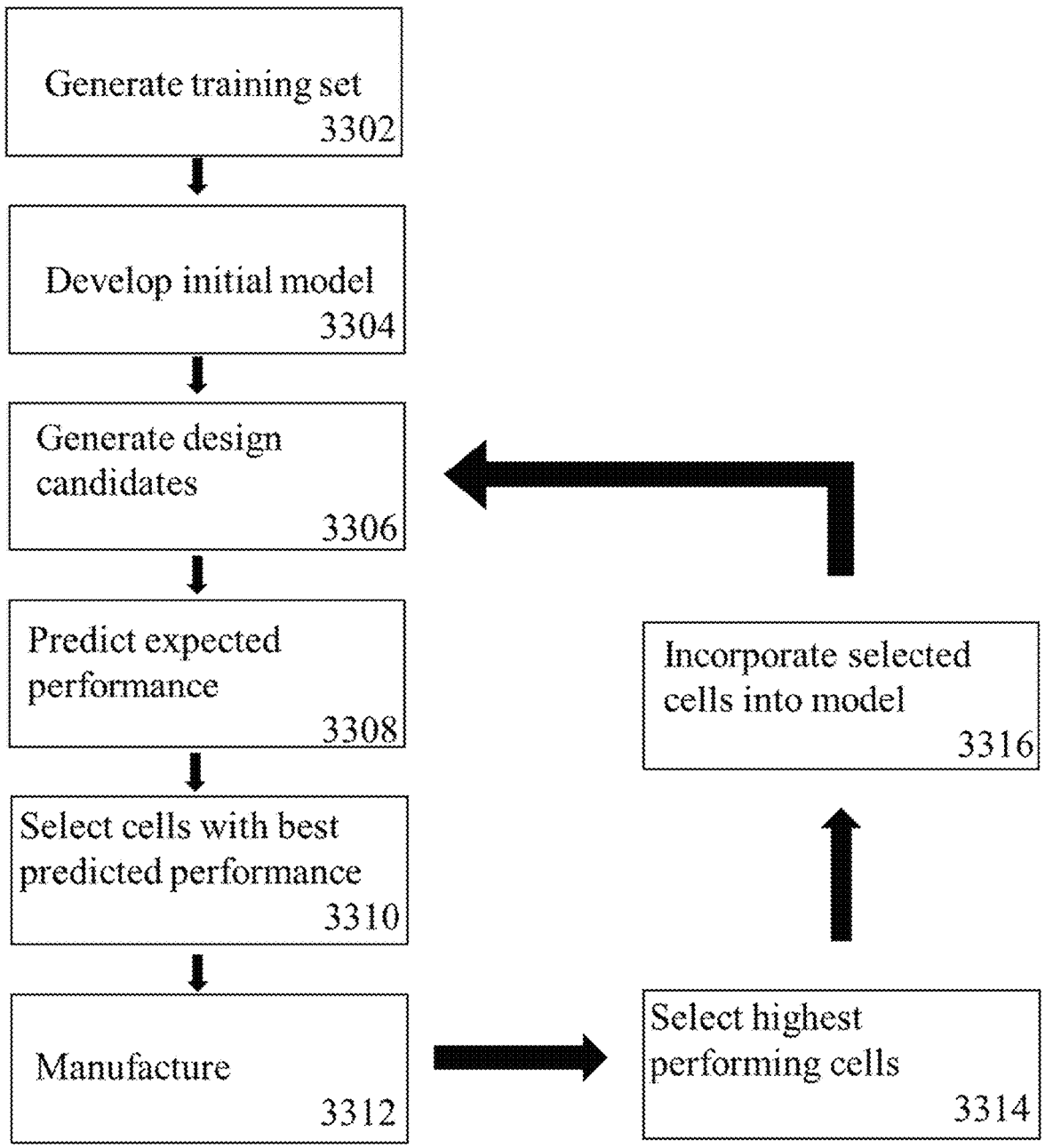
FIG. 4 depicts an embodiment of the iterative predictive design workflow of the present disclosure.

In sum, with reference to the flowchart of FIG. 4 the iterative predictive CHO cell design workflow may be described as follows:

Generate a training set of input and output variables, e.g., genetic changes as inputs and performance features as outputs (3302). Generation may be performed by the analysis equipment 214 based upon previous genetic changes and the corresponding measured performance of the CHO cells incorporating those genetic changes.

Develop an initial model (e.g., linear regression model) based upon training set (3304). This may be performed by the analysis equipment 214.

Generate design candidates (3306)

In one embodiment, the analysis equipment 214 may fix the number of genetic changes to be made to a background cell, in the form of combinations of changes. To represent these changes, the analysis equipment 214 may provide to the interpreter 204 one or more DNA specification expressions representing those combinations of changes. (These genetic changes or the host cells incorporating those changes may be referred to as "test inputs.") The interpreter 204 interprets the one or more DNA specifications, and the execution engine 207 executes the DNA specifications to populate the DNA specification with resolved outputs representing the individual candidate design cells for those changes.

Based upon the model, the analysis equipment 214 predicts expected performance of each candidate design (3308).

The analysis equipment 214 selects a limited number of candidate designs, e.g., 100, with highest predicted performance (3310).

As described elsewhere herein with respect to epistasis mapping, the analysis equipment 214 may account for second-order effects such as epistasis, by, e.g., filtering top designs for epistatic effects, or factoring epistasis into the predictive model.

Build the filtered candidate cells (at the factory 210) based on the factory order generated by the order placement engine 208 (3312).

The analysis equipment 214 measures the actual performance of the selected cells, selects a limited number of those selected cells based upon their superior actual performance (3314), and adds the design changes and their resulting performance to the predictive model (3316).

The analysis equipment 214 then iterates back to generation of new design candidate cells (3306), and continues iterating until a stop condition is satisfied. The stop condition may comprise, for example, the measured performance of at least one cell satisfying a performance metric, such as yield of a therapeutic protein of interest.

Machine Learning to Optimize CHO Cell Design

In the example above, the iterative optimization of CHO cell design employs feedback and linear regression to implement machine learning. In general, machine learning may be described as the optimization of performance criteria, e.g., parameters, techniques or other features, in the performance of an informational task (such as classification or regression) using a limited number of examples of labeled data, and then performing the same task on unknown data.

In supervised machine learning such as that of the linear regression example above, the machine (e.g., a computing device) learns, for example, by identifying patterns, categories, statistical relationships, or other attributes, exhibited by training data. The result of the learning is then used to predict whether new data will exhibit the same patterns, categories, statistical relationships, or other attributes.

Embodiments of the disclosure may employ other supervised machine learning techniques when training data is available. In the absence of training data, embodiments may employ unsupervised machine learning. Alternatively, embodiments may employ semi-supervised machine learning, using a small amount of labeled data and a large amount of unlabeled data. Embodiments may also employ feature selection to select the subset of the most relevant features to optimize performance of the machine learning model. Depending upon the type of machine learning approach selected, as alternatives or in addition to linear regression, embodiments may employ for example, logistic regression, neural networks, support vector machines (SVMs), decision trees, hidden Markov models, Bayesian networks, Gram Schmidt, reinforcement-based learning, cluster-based learning including hierarchical clustering, genetic algorithms, and any other suitable learning machines known in the art. In particular, embodiments may employ logistic regression to provide probabilities of classification (e.g., classification of genes into different functional groups) along with the classifications themselves. See, e.g., Shevade, A simple and efficient algorithm for gene selection using sparse logistic regression, Bioinformatics, Vol. 19, No. 17 2003, pp. 2246-2253, Leng, et al., Classification using functional data analysis for temporal gene expression data, Bioinformatics, Vol. 22, No. 1, Oxford University Press (2006), pp. 68-76, all of which are incorporated by reference in their entirety herein.

Embodiments may employ graphics processing unit (GPU) accelerated architectures that have found increasing popularity in performing machine learning tasks, particularly in the form known as deep neural networks (DNN). Embodiments of the disclosure may employ GPU-based machine learning, such as that described in GPU-Based Deep Learning Inference: A Performance and Power Analysis, NVidia Whitepaper, November 2015, Dahl, et al., Multi-task Neural Networks for QSAR Predictions, Dept. of Computer Science, Univ. of Toronto, June 2014 (arXiv: 1406.1231 [stat.ML]), all of which are incorporated by reference in their entirety herein. Machine learning techniques applicable to embodiments of the disclosure may also be found in, among other references, Libbrecht, et al., Machine learning applications in genetics and genomics, Nature Reviews: Genetics, Vol. 16, June 2015, Kashyap, et al., Big Data Analytics in Bioinformatics: A Machine Learning Perspective, Journal of Latex Class Files, Vol. 13, No. 9, September 2014, Prompramote, et al., Machine Learning in Bioinformatics, Chapter 5 of Bioinformatics Technologies, pp. 117-153, Springer Berlin Heidelberg 2005, all of which are incorporated by reference in their entirety herein.

Genomic Design and Engineering as a Service

Figure 2:
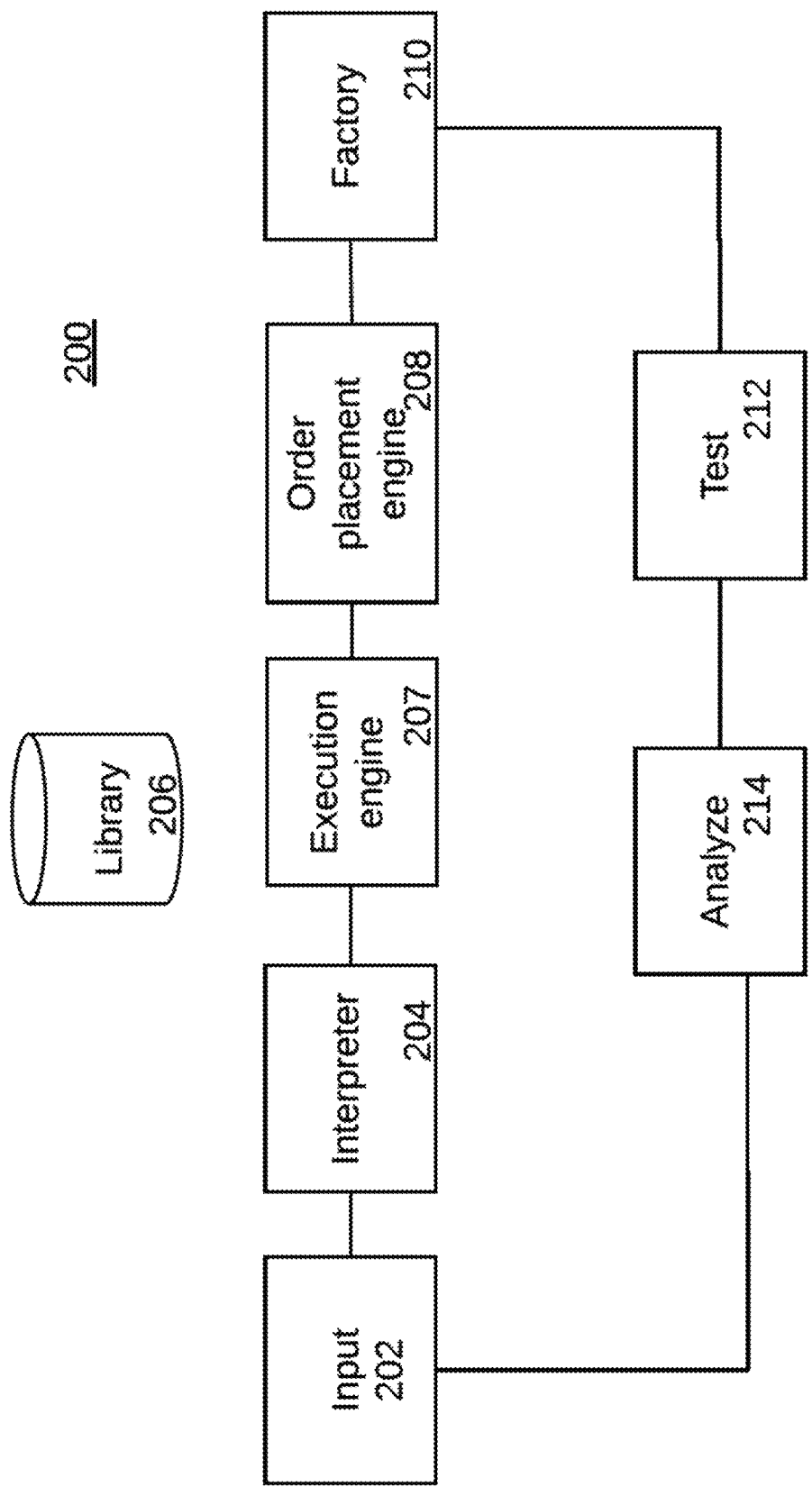
FIG. 2 diagrams an embodiment of a laboratory information management system (LIMS) of the present disclosure for CHO cell improvement.
Figure 3:
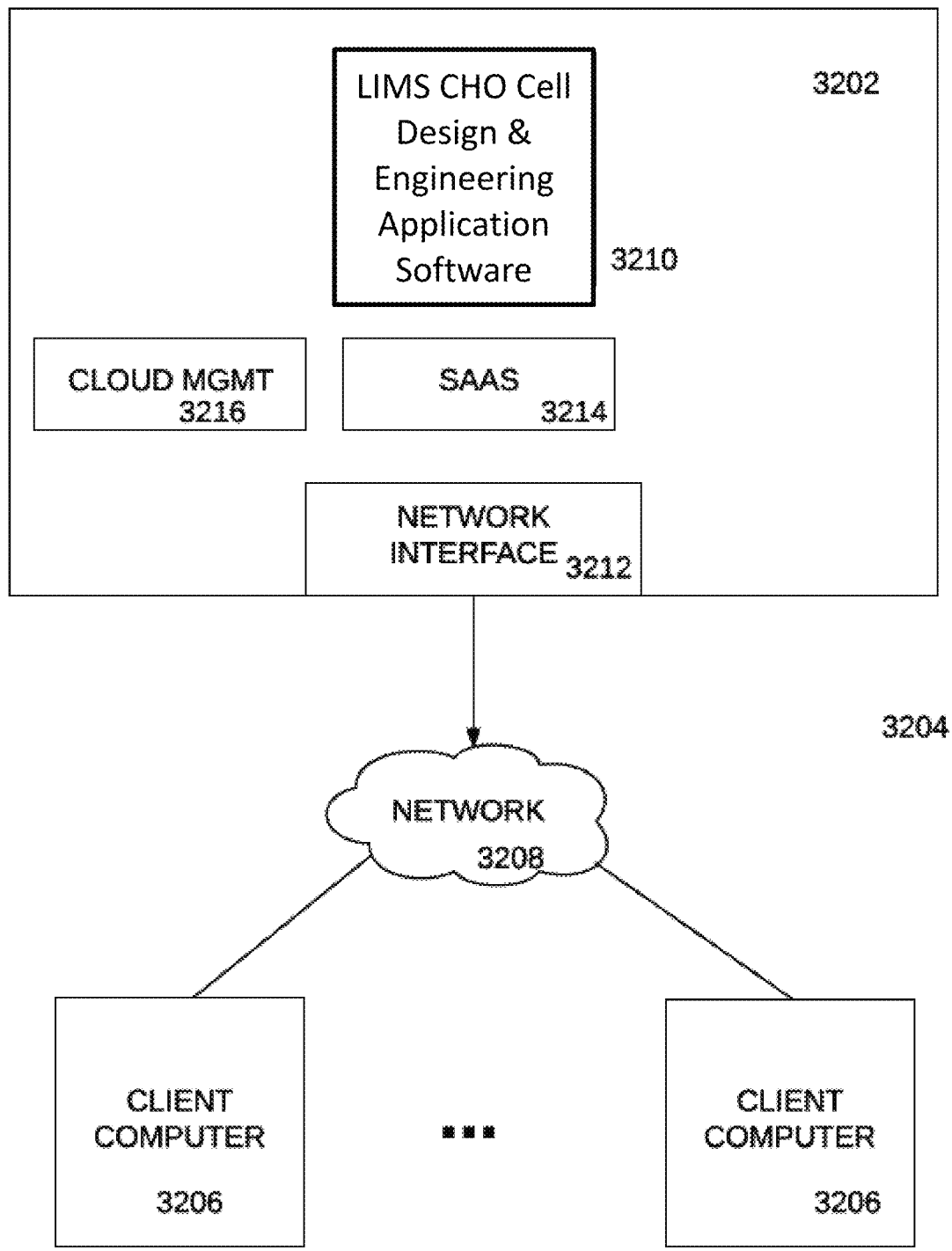
FIG. 3 diagrams a cloud computing implementation of embodiments of the LIMS system of the present disclosure.

In embodiments of the disclosure, the LIMS system software of FIG. 2 may be implemented in a cloud computing system 3202 of FIG. 3, to enable multiple users to design and build CHO cells according to embodiments of the present disclosure. FIG. 3 illustrates a cloud computing environment 3204 according to embodiments of the present disclosure. Client computers 3206, such as those illustrated in FIG. 3, access the LIMS system via a network 3208, such as the Internet. In embodiments, the LIMS system application software 3210 resides in the cloud computing system 3202. The LIMS system may employ one or more computing systems using one or more processors, of the type illustrated in FIG. 3. The cloud computing system itself includes a network interface 3212 to interface the LIMS system applications 3210 to the client computers 3206 via the network 3208. The network interface 3212 may include an application programming interface (API) to enable client applications at the client computers 3206 to access the LIMS system software 3210. In particular, through the API, client computers 3206 may access components of the LIMS system 200, including without limitation the software running the input interface 202, the interpreter 204, the execution engine 207, the order placement engine 208, the factory 210, as well as test equipment 212 and analysis equipment 214. A software as a service (SaaS) software module 3214 offers the LIMS system software 3210 as a service to the client computers 3206. A cloud management module 3216 manages access to the LIMS system 3210 by the client computers 3206. The cloud management module 3216 may enable a cloud architecture that employs multitenant applications, virtualization, or other architectures known in the art to serve multiple users.

Genomic Automation

Automation of the methods of the present disclosure enables high-throughput phenotypic screening and identification of target products from multiple test cell lines simultaneously.

The aforementioned genomic engineering predictive modeling platform is premised upon the fact that hundreds and thousands of cells are constructed in a high-throughput fashion. The robotic and computer systems described below are the structural mechanisms, by which such a high-throughput process can be carried out.

In some embodiments, the present disclosure teaches methods of improving host cell productivities. As part of this process, the present disclosure teaches methods of assembling DNA, building new cells, screening in plates, and screening in models for industrial therapeutic protein production. In some embodiments, the present disclosure teaches that one or more of the aforementioned methods of creating and testing new host cells is aided by automated robotics.

HTP Robotic Systems

In some embodiments, the automated methods of the disclosure comprise a robotic system. The systems outlined herein are generally directed to the use of 96- or 384-well microtiter plates, but as will be appreciated by those in the art, any number of different plates or configurations may be used. In addition, any or all of the steps outlined herein may be automated; thus, for example, the systems may be completely or partially automated.

In some embodiments, the automated systems of the present disclosure comprise one or more work modules. For example, in some embodiments, the automated system of the present disclosure comprises modules tailored for: promoter ladder creation, sequencing and building DNA, transfection, screening, protein testing/characterization, and CHO cell clonal selection (see FIG. 1).

As will be appreciated by those in the art, an automated system can include a wide variety of components, including, but not limited to: liquid handlers; one or more robotic arms; plate handlers for the positioning of microplates; plate sealers, plate piercers, automated lid handlers to remove and replace lids for wells on non-cross contamination plates; disposable tip assemblies for sample distribution with disposable tips; washable tip assemblies for sample distribution; 96 well loading blocks; integrated thermal cyclers; cooled reagent racks; microtiter plate pipette positions (optionally cooled); stacking towers for plates and tips; magnetic bead processing stations; filtrations systems; plate shakers; barcode readers and applicators; and computer systems.

In some embodiments, the robotic systems of the present disclosure include automated liquid and particle handling enabling high-throughput pipetting to perform all the steps in the process of gene targeting and recombination applications. This includes liquid and particle manipulations such as aspiration, dispensing, mixing, diluting, washing, accurate volumetric transfers; retrieving and discarding of pipette tips; and repetitive pipetting of identical volumes for multiple deliveries from a single sample aspiration. These manipulations are cross-contamination-free liquid, particle, cell, and organism transfers. The instruments perform automated replication of microplate samples to filters, membranes, and/or daughter plates, high-density transfers, full-plate serial dilutions, and high capacity operation.

In some embodiments, the customized automated liquid handling system of the disclosure is a TECAN machine (e.g. a customized TECAN Freedom Evo).

In some embodiments, the automated systems of the present disclosure are compatible with platforms for multi-well plates, deep-well plates, square well plates, reagent troughs, test tubes, mini tubes, microfuge tubes, cryovials, filters, micro array chips, optic fibers, beads, agarose and acrylamide gels, and other solid-phase matrices or platforms are accommodated on an upgradeable modular deck. In some embodiments, the automated systems of the present disclosure contain at least one modular deck for multi-position work surfaces for placing source and output samples, reagents, sample and reagent dilution, assay plates, sample and reagent reservoirs, pipette tips, and an active tip-washing station.

In some embodiments, the automated systems of the present disclosure include high-throughput electroporation systems. In some embodiments, the high-throughput electroporation systems are capable of transforming cells in 96 or 384-well plates. In some embodiments, the high-throughput electroporation systems include VWR® High-throughput Electroporation Systems, BTX™, Bio-Rad® Gene Pulser MXcell™ or other multi-well electroporation system.

In some embodiments, the integrated thermal cycler and/or thermal regulators are used for stabilizing the temperature of heat exchangers such as controlled blocks or platforms to provide accurate temperature control of incubating samples from 0° C. to 100° C.

In some embodiments, the automated systems of the present disclosure are compatible with interchangeable machine-heads (single or multi-channel) with single or multiple magnetic probes, affinity probes, replicators or pipetters, capable of robotically manipulating liquid, particles, cells, and multi-cellular organisms. Multi-well or multi-tube magnetic separators and filtration stations manipulate liquid, particles, cells, and organisms in single or multiple sample formats.

In some embodiments, the automated systems of the present disclosure are compatible with camera vision and/or spectrometer systems. Thus, in some embodiments, the automated systems of the present disclosure are capable of detecting and logging color and absorption changes in ongoing cellular cultures.

In some embodiments, the automated system of the present disclosure is designed to be flexible and adaptable with multiple hardware add-ons to allow the system to carry out multiple applications. The software program modules allow creation, modification, and running of methods. The system's diagnostic modules allow setup, instrument alignment, and motor operations. The customized tools, labware, and liquid and particle transfer patterns allow different applications to be programmed and performed. The database allows method and parameter storage. Robotic and computer interfaces allow communication between instruments.

Persons having skill in the art will recognize the various robotic platforms capable of carrying out the HTP engineering methods of the present disclosure.

Computer System Hardware

Figure 5:
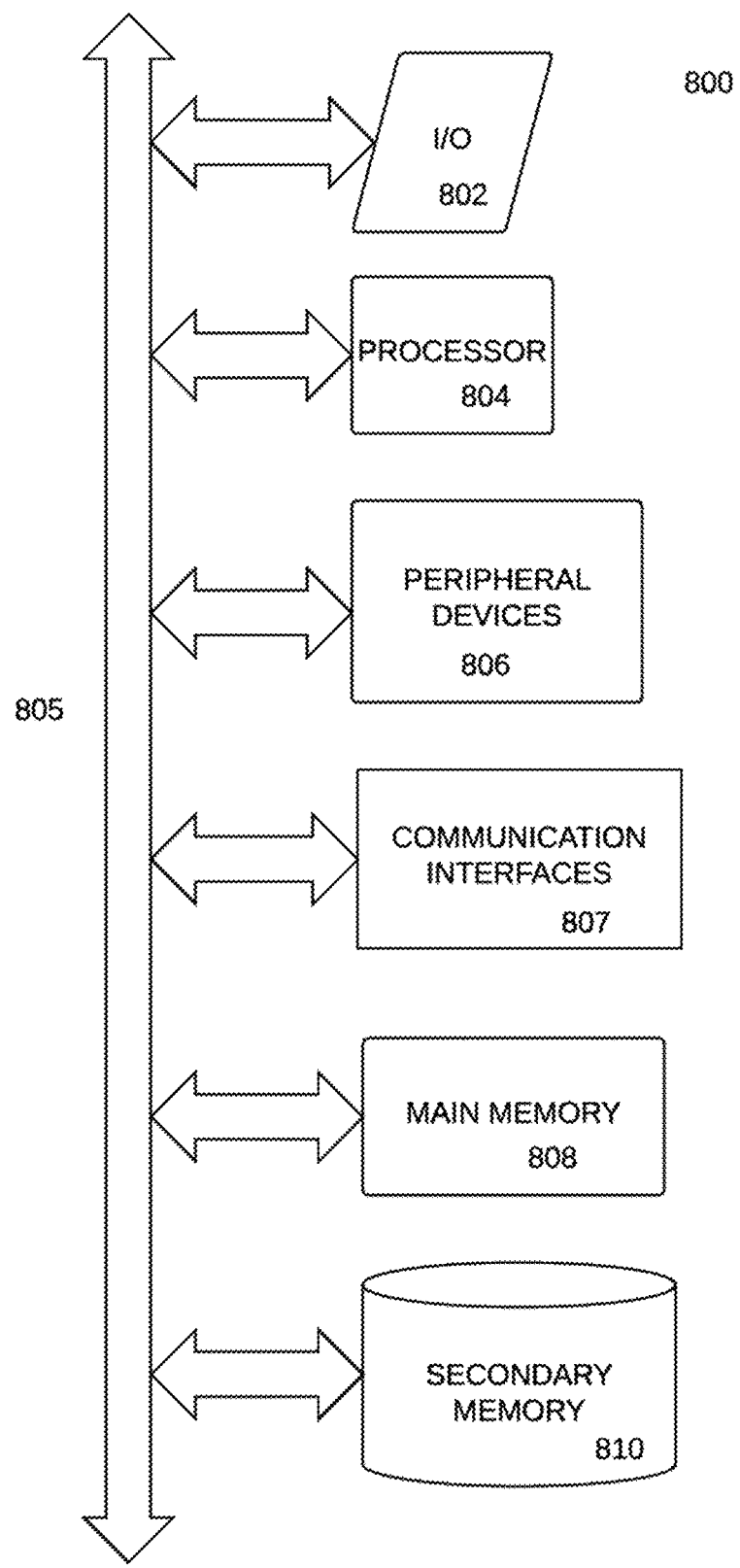
FIG. 5 diagrams an embodiment of a computer system, according to embodiments of the present disclosure.

FIG. 5 illustrates an example of a computer system 800 that may be used to execute program code stored in a non-transitory computer readable medium (e.g., memory) in accordance with embodiments of the disclosure. The computer system includes an input/output subsystem 802, which may be used to interface with human users and/or other computer systems depending upon the application. The I/O subsystem 802 may include, e.g., a keyboard, mouse, graphical user interface, touchscreen, or other interfaces for input, and, e.g., an LED or other flat screen display, or other interfaces for output, including application program interfaces (APIs). Other elements of embodiments of the disclosure, such as the components of the LIMS system, may be implemented with a computer system like that of computer system 800.

Program code may be stored in non-transitory media such as persistent storage in secondary memory 810 or main memory 808 or both. Main memory 808 may include volatile memory such as random access memory (RAM) or non-volatile memory such as read only memory (ROM), as well as different levels of cache memory for faster access to instructions and data. Secondary memory may include persistent storage such as solid state drives, hard disk drives or optical disks. One or more processors 804 reads program code from one or more non-transitory media and executes the code to enable the computer system to accomplish the methods performed by the embodiments herein. Those skilled in the art will understand that the processor(s) may ingest source code, and interpret or compile the source code into machine code that is understandable at the hardware gate level of the processor(s) 804. The processor(s) 804 may include graphics processing units (GPUs) for handling computationally intensive tasks. Particularly in machine learning, one or more CPUs 804 may offload the processing of large quantities of data to one or more GPUs 804.

The processor(s) 804 may communicate with external networks via one or more communications interfaces 807, such as a network interface card, WiFi transceiver, etc. A bus 805 communicatively couples the I/O subsystem 802, the processor(s) 804, peripheral devices 806, communications interfaces 807, memory 808, and persistent storage 810. Embodiments of the disclosure are not limited to this representative architecture. Alternative embodiments may employ different arrangements and types of components, e.g., separate buses for input-output components and memory subsystems.

Those skilled in the art will understand that some or all of the elements of embodiments of the disclosure, and their accompanying operations, may be implemented wholly or partially by one or more computer systems including one or more processors and one or more memory systems like those of computer system 800. In particular, the elements of the LIMS system 200 and any robotics and other automated systems or devices described herein may be computer-implemented. Some elements and functionality may be implemented locally and others may be implemented in a distributed fashion over a network through different servers, e.g., in client-server fashion, for example. In particular, server-side operations may be made available to multiple clients in a software as a service (SaaS) fashion, as shown in FIG. 3.

The term component in this context refers broadly to software, hardware, or firmware (or any combination thereof) component. Components are typically functional components that can generate useful data or other output using specified input(s). A component may or may not be self-contained. An application program (also called an "application") may include one or more components, or a component can include one or more application programs.

Some embodiments include some, all, or none of the components along with other modules or application components. Still yet, various embodiments may incorporate two or more of these components into a single module and/or associate a portion of the functionality of one or more of these components with a different component.

The term "memory" can be any device or mechanism used for storing information. In accordance with some embodiments of the present disclosure, memory is intended to encompass any type of, but is not limited to: volatile memory, nonvolatile memory, and dynamic memory. For example, memory can be random access memory, memory storage devices, optical memory devices, magnetic media, floppy disks, magnetic tapes, hard drives, SIMMs, SDRAM, DIMMs, RDRAM, DDR RAM, SODIMMS, erasable programmable read-only memories (EPROMs), electrically erasable programmable read-only memories (EEPROMs), compact disks, DVDs, and/or the like. In accordance with some embodiments, memory may include one or more disk drives, flash drives, databases, local cache memories, processor cache memories, relational databases, flat databases, servers, cloud based platforms, and/or the like. In addition, those of ordinary skill in the art will appreciate many additional devices and techniques for storing information can be used as memory.

Memory may be used to store instructions for running one or more applications or modules on a processor. For example, memory could be used in some embodiments to house all or some of the instructions needed to execute the functionality of one or more of the modules and/or applications disclosed in this application.

HTP CHO Cell Engineering Based Upon Genetic Design Predictions: An Example Workflow In some embodiments, the present disclosure teaches the directed engineering of new host organisms based on the recommendations of the computational analysis systems of the present disclosure.

In some embodiments, the present disclosure is compatible with all genetic design and cloning methods. That is, in some embodiments, the present disclosure teaches the use of traditional cloning techniques such as polymerase chain reaction, restriction enzyme digestions, ligation, homologous recombination, RT PCR, and others generally known in the art and are disclosed in for example: Sambrook et al. (2001) Molecular Cloning: A Laboratory Manual (3rd ed., Cold Spring Harbor Laboratory Press, Plainview, N.Y.), incorporated herein by reference.

In some embodiments, the cloned sequences can include possibilities from any of the HTP genetic design libraries taught herein, for example: promoters from a promoter swap library.

Further, the exact sequence combinations that should be included in a particular construct can be informed by the epistatic mapping function.

In other embodiments, the cloned sequences can also include sequences based on rational design (hypothesis-driven) and/or sequences based on other sources, such as scientific publications.

Build Specific DNA Oligonucleotides

In some embodiments, the present disclosure teaches inserting and/or replacing and/or altering and/or deleting a DNA segment of the host cell organism. In some aspects, the methods taught herein involve building an oligonucleotide of interest (i.e. a target DNA segment), that will be incorporated into the genome of a host organism. In some embodiments, the target DNA segments of the present disclosure can be obtained via any method known in the art, including: copying or cutting from a known template, mutation, or DNA synthesis. In some embodiments, the present disclosure is compatible with commercially available gene synthesis products for producing target DNA sequences (e.g., GeneArt™, GeneMaker™, GenScript™, Anagen™, Blue Heron™, Entelechon™, GeNOsys, Inc., or Qiagen™)

In some embodiments, the target DNA segment is designed to incorporate a promoter into a selected DNA region of the host organism.

In some embodiments, the oligonucleotides used in the inventive methods can be synthesized using any of the methods of enzymatic or chemical synthesis known in the art. The oligonucleotides may be synthesized on solid supports such as controlled pore glass (CPG), polystyrene beads, or membranes composed of thermoplastic polymers that may contain CPG. Oligonucleotides can also be synthesized on arrays, on a parallel microscale using microfluidics (Tian et al., Mol. BioSyst., 5, 714-722 (2009)), or known technologies that offer combinations of both (see Jacobsen et al., U.S. Pat. App. No. 2011/0172127).

Synthesis on arrays or through microfluidics offers an advantage over conventional solid support synthesis by reducing costs through lower reagent use. The scale required for gene synthesis is low, so the scale of oligonucleotide product synthesized from arrays or through microfluidics is acceptable. However, the synthesized oligonucleotides are of lesser quality than when using solid support synthesis (See Tian infra.; see also Staehler et al., U.S. Pat. App. No. 2010/0216648).

A great number of advances have been achieved in the traditional four-step phosphoramidite chemistry since it was first described in the 1980s (see for example, Sierzchala, et al. *J. Am. Chem. Soc.*, 125, 13427-13441 (2003) using peroxy anion deprotection; Hayakawa et al., U.S. Pat. No. 6,040,439 for alternative protecting groups; Azhayev et al, *Tetrahedron* 57, 4977-4986 (2001) for universal supports; Kozlov et al., *Nucleosides, Nucleotides, and Nucleic Acids*, 24 (5-7), 1037-1041 (2005) for improved synthesis of longer oligonucleotides through the use of large-pore CPG; and Damha et al., *NAR*, 18, 3813-3821 (1990) for improved derivatization).

Regardless of the type of synthesis, the resulting oligonucleotides may then form the smaller building blocks for longer oligonucleotides. In some embodiments, smaller oligonucleotides can be joined together using protocols known in the art, such as polymerase chain assembly (PCA), ligase chain reaction (LCR), and thermodynamically balanced inside-out synthesis (TBIO) (see Czar et al. Trends in Biotechnology, 27, 63-71 (2009)). In PCA, oligonucleotides spanning the entire length of the desired longer product are annealed and extended in multiple cycles (typically about 55 cycles) to eventually achieve full-length product. LCR uses ligase enzyme to join two oligonucleotides that are both annealed to a third oligonucleotide. TBIO synthesis starts at the center of the desired product and is progressively extended in both directions by using overlapping oligonucleotides that are homologous to the forward strand at the 5' end of the gene and against the reverse strand at the 3' end of the gene.

Another method of synthesizing a larger double stranded DNA fragment is to combine smaller oligonucleotides through top-strand PCR (TSP). In this method, a plurality of oligonucleotides spans the entire length of a desired product and contain overlapping regions to the adjacent oligonucleotide(s). Amplification can be performed with universal forward and reverse primers, and through multiple cycles of amplification a full-length double stranded DNA product is formed. This product can then undergo optional error correction and further amplification that results in the desired double stranded DNA fragment end product.

In one method of TSP, the set of smaller oligonucleotides that will be combined to form the full-length desired product are between 40-200 bases long and overlap each other by at least about 15-20 bases. For practical purposes, the overlap region should be at a minimum long enough to ensure specific annealing of oligonucleotides and have a high enough melting temperature (Tm) to anneal at the reaction temperature employed. The overlap can extend to the point where a given oligonucleotide is completely overlapped by adjacent oligonucleotides. The amount of overlap does not seem to have any effect on the quality of the final product. The first and last oligonucleotide building block in the assembly should contain binding sites for forward and reverse amplification primers. In one embodiment, the terminal end sequence of the first and last oligonucleotide contain the same sequence of complementarity to allow for the use of universal primers.

Transfection of Host Cell

In some embodiments, the present disclosure teaches methods for constructing vectors capable of inserting desired target DNA sections (e.g. containing a particular promoter, and/or GOI, such as an antibody) into the genome of host organisms, e.g., CHO cells.

In some embodiments, the present disclosure is compatible with any vector suited for transformation or transfection into the host organism.

In some embodiments, the present disclosure teaches use of shuttle vectors compatible with a host cell. Shuttle vectors for use in the methods provided herein can comprise markers for selection and/or counter-selection as described herein. The markers can be any markers known in the art and/or provided herein. The shuttle vectors can further comprise any regulatory sequence(s) and/or sequences useful in the assembly of said shuttle vectors as known in the art. The regulatory sequence can be any regulatory sequence known in the art or provided herein such as, for example, a promoter, start, stop, signal, secretion and/or termination sequence used by the genetic machinery of the host cell. In certain instances, the target DNA can be inserted into vectors, constructs or plasmids obtainable from any repository or catalogue product, such as a commercial vector (see e.g., DNA2.0 custom or GATEWAY® vectors). In certain instances, the target DNA can be inserted into vectors, constructs or plasmids obtainable from any repository or catalogue product, such as a commercial vector (see e.g., DNA2.0 custom or GATEWAY® vectors).

In some embodiments, the assembly/cloning methods of the present disclosure may employ at least one of the following assembly strategies: 1) type II conventional cloning, ii) type II 5-mediated or "Golden Gate" cloning (see, e.g., Engler, C., R. Kandzia, and S. Marillonnet. 2008 "A one pot, one step, precision cloning method with high-throughput capability". PLos One 3:e3647; Kotera, I., and T. Nagai. 2008 "A high-throughput and single-tube recombination of crude PCR products using a DNA polymerase inhibitor and type IIS restriction enzyme." J Biotechnol 137:1-7.; Weber, E., R. Gruetzner, S. Werner, C. Engler, and S. Marillonnet. 2011 Assembly of Designer TAL Effectors by Golden Gate Cloning. PloS One 6:e19722), iii) GATEWAY® recombination, iv) TOPO® cloning, exonuclease-mediated assembly (Aslanidis and de Jong 1990. "Ligation-independent cloning of PCR products (LIC-PCR)." Nucleic Acids Research, Vol. 18, No. 20 6069), v) homologous recombination, vi) non-homologous end joining, vii) Gibson assembly (Gibson et al., 2009 "Enzymatic assembly of DNA molecules up to several hundred kilobases" Nature Methods 6, 343-345) or a combination thereof. Modular type IIS based assembly strategies are disclosed in PCT Publication WO 2011/154147, the disclosure of which is incorporated herein by reference.

Although plasmids do not naturally exist in mammals, scientists can still reap the benefits of plasmid-based research using synthetic vectors and cultured mammalian cells. Of course, these mammalian vectors must be compatible with the cell type they are transfected into—a bacterial origin of replication (ORI) will not allow for plasmid replication in mammalian cells, for example, and a toxin that kills bacteria may not have any discernable effect on mammalian cells.

The means of introducing genetic material (such as plasmids) into mammalian cells is a process called transfection. Transfection is somewhat comparable to bacterial transformation (the introduction of DNA into bacterial cells); however, the techniques and reagents vary. Plasmid transfection into mammalian cells is fairly straightforward and the resultant cells can either express the plasmid DNA transiently (similar to bacteria) or incorporate the genetic material directly into the genome to form a stable transfection. Unlike bacterial transformation, scientists do not "select" for cells that have taken up the plasmid in the same way. Selection methods, described below, are typically employed when creating stable cell lines and are not used for general plasmid selection. Instead, reporter genes are often employed to easily monitor transfection efficiencies and expression levels in the cells. Ideally, the chosen reporter is unique to the cell, is expressed from the plasmid, and can be assayed conveniently. A direct test for your gene of interest may be another method to assess transfection success. GFP is often used as a reporter.

For many experiments, it is sufficient for the transfected plasmid to be expressed transiently. Since the DNA introduced in the transfection process is not integrated into the nuclear genome, in the absence of plasmid replication, the foreign DNA will be degraded or diluted over time. This, however, may not be a problem depending on the duration or other parameters of the experiment. Mammalian cells double at a much slower rate than that of bacteria (~24 h vs 20 min, respectively). Therefore, it is not always critical to make sure the plasmid replicates in the cell, as many of these experiments are concluded within 48 h of transfection.

the genome. Positive selection is a means of picking up positive traits (i.e. the plasmid contains a cassette that will make cells resistant to a toxin), whereas negative selection would be the picking up of a negative trait (i.e. the plasmid contains a cassette that will make cells sensitive to a toxin). Negative selection techniques can be used in conjunction with positive selection to ensure the gene gets targeted to a specific location within the genome.

Positive selection in mammalian cells works similarly to that in bacteria and a table of the most commonly used selection markers are listed below:

TABLE 3

Common Selection Markers in CHO Cell Transfection

| Name | Gene Conferring Resistance | Cell Types* | Mode of Action** | Working Concentration*** |
|---|---|---|---|---|
| Blasticidin | bsd | HeLa, NIH3T3, CHO, COS-1, 293HEK | Inhibits termination step of translation | 2-10 ug/mL |
| G418/Geneticin | Neo | HeLa, NIH3T3, CHO, 293HEK, Jurkat T cells | Blocks polypeptide synthesis at 80S; inhibits chain elongation | 100-800 ug/mL |
| Hygromycin B | hygB | HeLa, NIH3T3, CHO, Jurkat T cells | Blocks polypeptide synthesis at 80S; inhibits chain elongation. | 50-500 ug/mL |
| Puromycin | Pac | HeLa, 293HEK, Jurkat T cells | Inhibits protein synthesis; premature chain termination | 1-10 ug/mL |
| Zeocin | Sh bla | HeLa, NIH3T3, CHO, COS-1, 293HEK, Jurkat T cells | Complexes with DNA; causes strand scissions | 100-400 ug/mL |

*Not comprehensive.
**In eukaryotes.
***The concentration used for selection is typically more (double) than that used for maintenance of a transfected cell line.

Of course, it is possible that one may not want the plasmid depleted, but still want to use transient transfection methods. Since there are no "natural" mammalian ORIs, scientists have usurped viral-based ORIs to fill the void. These ORIs, however, require additional components expressed in trans within the cell for effective replication. Cell lines expressing the Epstein-Barr virus (EBV) nuclear antigen 1 (EBNA1) or the SV40 large-T antigen (293E or 293T cells), allow for episomal amplification of plasmids containing the viral EBV or SV40 ORIs, respectively. The presence of these viral components greatly reduces the rate of plasmid dilution but does not guarantee 100% transfection efficiency.

Stable Transfection

A stable transfection is used to create a population of cells that have fully and successfully incorporated foreign genetic material (GOI, gene of interest) into their genomes. Unlike plasmids used for expression in yeast and bacteria, plasmids used for stable transfections rarely contain an ORI since the integrated DNA will be replicated as part of the genome. Because the foreign DNA becomes a permanent addition to the host genome, the cells will continually express the genetic traits of the foreign material and will subsequently pass it on to future generations. Stably transfected cells may be considered an entirely new cell line from that of the original parental cells.

Positive Selection in Mammalian Cells

To achieve stable transfection, there should be a selective pressure to force cells to incorporate the plasmid DNA into Protein Testing and Characterization—Measuring the Effect of the PROSWAP Induced Genetic Perturbations The outcome of utilizing the HTP promoter swap genomic engineering tool to modulate expression of various target genes, will be evaluated for the effect that such procedure has upon a GOI, which in some embodiments is a therapeutic protein, such as an antibody (Ab).

The promoter swap tool allows for a HTP and systematic "probe," by which to modulate certain target genes, and then measure the effect of such modulation on the phenotypic characteristics of a GOI product, e.g. the characteristics of a produced antibody. The evaluation of the effect on the product of the GOI (i.e. therapeutic protein and/or antibody) will entail a number of Ab phenotypic characterizations, such as: titer, N-terminal cleavage, glycosylation, etc., in order to ensure the genetic perturbations did not interfere negatively with the expression of the Ab.

Exemplary Genes of Interest—Antibodies

The present disclosure teaches HTP genetic engineering of CHO cells to improve the expression of desired genes of interest (GOIs). One such gene of interest category would be genes which code for human therapeutic proteins. For example, improved expression of genes coding for antibodies and the production of antibodies via CHO cells is contemplated.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the NH2-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, F(ab')2, and or other antibody fragments that retain specific binding to antigen.

Antibodies may exist in a variety of other forms including, for example, Fv, Fab, and (Fab')2, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988); Bird et al., Science, 242, 423-426 (1988); see Hood et al., "Immunology", Benjamin, N.Y., 2nd ed. (1984), and Hunkapiller and Hood, Nature, 323, 15-16 (1986)).

An immunoglobulin light or heavy chain variable region consists of a "framework" region interrupted by three hypervariable regions, also called "complementarity determining regions" or CDRs. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a rabbit monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody.

As used herein, unless otherwise indicated or clear from the context, antibody domains, regions and fragments are accorded standard definitions as are well known in the art. See, e.g., Abbas, A. K., et al., (1991) Cellular and Molecular Immunology, W. B. Saunders Company, Philadelphia, Pa.

As used herein, the term "humanized antibody" or "humanized immunoglobulin" refers to an antibody comprising one or more CDRs from an animal antibody, the antibody having been modified in such a way so as to be less immunogenic in a human than the parental animal antibody. An animal antibody can be humanized using a number of methodologies, including chimeric antibody production, CDR grafting (also called reshaping), and antibody resurfacing.

As used herein, the term "murinized antibody" or "murinized immunoglobulin" refers to an antibody comprising one or more CDRs from an animal antibody, the antibody having been modified in such a way so as to be less immunogenic in a mouse than the parental animal antibody. An animal antibody can be murinized using a number of methodologies, including chimeric antibody production, CDR grafting (also called reshaping), and antibody resurfacing.

As used herein, the terms "determining," "measuring," and "assessing," and "assaying" are used interchangeably and include both quantitative and qualitative determinations.

As aforementioned, there are five immunoglobulin classes (isotypes) of antibody molecules found in serum: IgG, IgM, IgA, IgE, and IgD. They are distinguished by the type of heavy chain they contain. IgG molecules possess heavy chains known as γ-chains; IgMs have chains; IgAs have α-chains; IgEs have ε-chains; and IgDs have δ-chains. The variation in heavy chain polypeptides allows each immunoglobulin class to function in a different type of immune response or during a different stage of the body's defense. The amino acid sequences that confer these functional differences are located mainly within the Fc domain.

Antibody classes also differ in their valency, i.e. the number of arms available to bind antigen. This arises from the ability of certain immunoglobulins to form multimers through linkage of their Fc domains via a J chain. For example, IgM is a pentamer of five identical "Y" shaped monomers. Therefore, the complete IgM protein contains 10 heavy chains, 10 light chains and 10 antigen binding arms (giving IgM a valency of 10).

In humans, there are only two kinds of light chains—κ and λ (based on subtle amino acid differences in the VL and CL regions). The κ and λ chains are found 67% and 33% of the time, respectively. Any antibody can be formed by the association of one heavy chain type with one light chain type. In every possible combination there will be two identical heavy and light chains in the antibody unit (monomer). Hence the IgM pentamer can either comprise $(\mu_2\kappa_2)_5$ or $(\mu_2\kappa_2)_5$.

As mentioned previously, immunoglobulins are further broken down into four subclasses designated IgG1, IgG2, IgG3 and IgG4 (listed in decreasing order of abundance in the serum). They share more than 95% sequence homology in the CH regions of the γ-heavy chains. There are also two subclasses of IgA: IgA1 (90%) and IgA2 (10%). Serum IgA is a monomer but is found in secretions such as tears, mucous and saliva as a dimer. In secretions, IgA has a J chain and another protein called the secretory piece (or T piece) associated with it. In addition, several subclasses of κ and λ light chains are known to exist.

The data in Table 4 summarizes some of the aforementioned information on human antibodies.

TABLE 4

Human Antibody Properties

| Property | IgG | | | | IgA | | IgM | IgD | IgE |
|---|---|---|---|---|---|---|---|---|---|
| H Chain class (heavy chain) | Γ | | | | α | | μ | δ | ε |
| H Chain Subclasses | γ1 | γ2 | γ3 | γ4 | α1 | α2 | None | None | None |
| H Chain MW | 50 kDa | 50 kDa | 60 kDa | 50 kDa | 55 kDa | 55 kDa | 70 kDa | 62 kDa | 70 kDa |
| L Chain MW* (light chain k & λ) | 23 kDa | 23 kDa | 23 kDa | 23 kDa | 23 kDa | 23 kDa | 23 kDa | 23 kDa | 23 kDa |
| Total MW | 150 kDa | 150 kDa | 170 kDa | 150 kDa | 160 kDa (serum) 600 kDa (secretory) | 160 kDa (serum) 600 kDa (secretory) | 970 kDa | 180 kDa | 190 kDa |
| Ext. Coeff. 0.1% @280 nm | 1.4 | 1.4 | 1.4 | 1.4 | 1.32 | 1.32 | 1.18 | 1.7 | 1.53 |
| Complement fixation | weak | weak | Strong | no | No | no | strong | no | no |
| Fc receptor binding | strong | weak | Strong | weak | Yes | yes | yes | no | yes |
| Mast cell/basophil degranulation | no | no | No | no | No | no | no | no | yes |
| Placental transfer | strong | weak | Strong | strong | No | no | no | no | no |

*Light chains are present on all Immunoglobulin classes. In humans, k. chains are found 67% of the time, and λ chains are found 33% of the time.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

A brief table of contents is provided below solely for the purpose of assisting the reader. Nothing in this table of contents is meant to limit the scope of the examples or disclosure of the application.

TABLE 5

Table of Contents For Example Section

| Example | Title | Brief Description |
|---|---|---|
| 1 | A General Workflow for Implementation of a Promoter Swap Library to Explore the Genetic Landscape of Targeted Pathway Genes | Describes the general workflow that is implemented when utilizing the HTP promoter swap genomic engineering tool to explore the genomic landscape associated with a targeted pathway involved with a phenotypic parameter of interest, e.g. therapeutic protein production. |
| 2 | A Specific Implementation of a Promoter Swap Library to Explore Pathway Antibody Expression Dependence | Describes the utilization of the HTP promoter swap genomic engineering tool to explore the genomic landscape associated with eight pathways involved with the production of antibodies in CHO cells. |
| 3 | Consolidation and Multi-Factor Combinatorial Testing of a Promoter Swap Library | Describes the consolidation of beneficial genetic alterations (e.g. particular promoter:gene combos) that have been discovered utilizing the HTP promoter swap genomic engineering tool. |

Example 1: A General Workflow for Implementation of a Promoter Swap Library to Explore the Genetic Landscape of Targeted Pathway Genes This example illustrates an embodiment of the HTP genomic engineering procedure, which utilizes the HTP promoter swap genomic engineering tool.

A. Identification of a Target for Promoter Swapping

As aforementioned, promoter swapping is a multi-step process that comprises a step of: Selecting a set of "n" genes to target.

In this example, the inventors have identified a group of eight functionalities, which are thought to be important in CHO cell therapeutic protein production. From within each of these eight broad functionalities, the inventors have then chosen a single particular gene to target with the promoter swap genomic engineering tool.

Consequently, there have been eight target genes, one from each representative functionality, chosen for the experiment. (See, FIG. 6 for target genes, and Example 2).

B. Creation of Promoter Ladder

Another step in the implementation of a promoter swap process is the selection of a set of "x" promoters to act as a "ladder". Ideally these promoters have been shown to lead to highly variable expression across multiple genomic loci, but the only requirement is that they perturb gene expression in some way.

These promoter ladders, in some embodiments, are created by: identifying natural, native, or wild-type promoters associated with the target gene of interest and then mutating/altering said promoter to derive multiple synthetic promoter sequences. Each of these edited promoters is tested for effect on target gene expression.

In other embodiments, the promoters are not derived from a natural or native CHO gene promoter, but rather are heterologous promoters introduced into the CHO cell genome.

In some embodiments, the promoters are tested for expression activity across a variety of conditions, such that each promoter's activity is documented/characterized/annotated and stored in a database.

The promoters are subsequently organized into "ladders" arranged based on the strength of their expression (e.g., with highly expressing promoters near the top, and attenuated expression near the bottom, therefore leading to the term "ladder").

C. Associating Promoters from the Ladder with Target Genes

Another step in the implementation of a promoter swap process is the HTP engineering of various CHO cells that comprise a given promoter from the promoter ladder associated with a particular target gene.

If a native promoter exists in front of target gene n and its sequence is known, then replacement of the native promoter with each of the x promoters in the ladder is carried out.

When the native promoter does not exist or its sequence is unknown, then insertion of each of the x promoters in the ladder in front of gene n is carried out.

In this way, a library of CHO cells is constructed, wherein each member of the library is an instance of x promoter operably linked to n target gene, in an otherwise identical genetic context.

D. HTP Screening of the CHO Cells

A final step in the promoter swap process is the HTP screening of the CHO cells in the aforementioned library. Each of the derived cells represents an instance of x promoter linked to n target, in an otherwise identical genetic background.

By implementing a HTP screening of each cell, in a scenario where their performance against one or more metrics is characterized, the inventors are able to determine what promoter/target gene association is most beneficial for a given metric (e.g. optimization of production of a therapeutic protein).

Example 2: A Specific Implementation of a Promoter Swap Library to Explore Pathway Antibody Expression Dependence The present study utilizes the HTP promoter swap genomic engineering tool to improve antibody expression in CHO cells. The promoter swap tool is used to clearly identify the relationship between pathway and protein expression and quality.

To evaluate the relationship between the targeted genetic function and antibody expression/secretion, multiple strains are constructed that differ in a single genetic loci from each other. The genetic change involves the replacement of the endogenous promoter driving the expression of the genes of the target pathways with a heterologous promoter(s) of varying strengths, i.e., PROSWAP. Various schematic depictions of the exemplary embodiment are found in FIGS. 6-10.

The overall genomic editing approach to effect the desired change is to target the genomic loci with Cas9 and a sgRNA to cut the genome at the desired location, and insertion at that locus of a DNA cassette carrying selection markers and the promoter of interest. Other CRISPR systems, for example Cpf1, may also be used.

The construction and evaluation of the CHO strains with CRISPR assisted PROSWAP of target genes can be divided into three phases:

Phase I—Construction and Isolation of mAB Producing Clones*

The in-house strain from Horizon discovery (a derivative of CHO-K1) is transfected with a GS-vector encoding mAb (monoclonal antibody) producing genes. The host strain lacks a functional Glutamine synthase (GS) making it an auxotroph for Glutamine. Upon transfection with a linearized GS carrying vector, random insertion of the vector leads to Glutamine prototrophy and the integrants are isolated by culturing in the absence of Glutamine. The selection pressure is enhanced by supplementing the media with Methionine Sulphoximine (MSX), a chemical inhibitor for GS.

Figure 10:
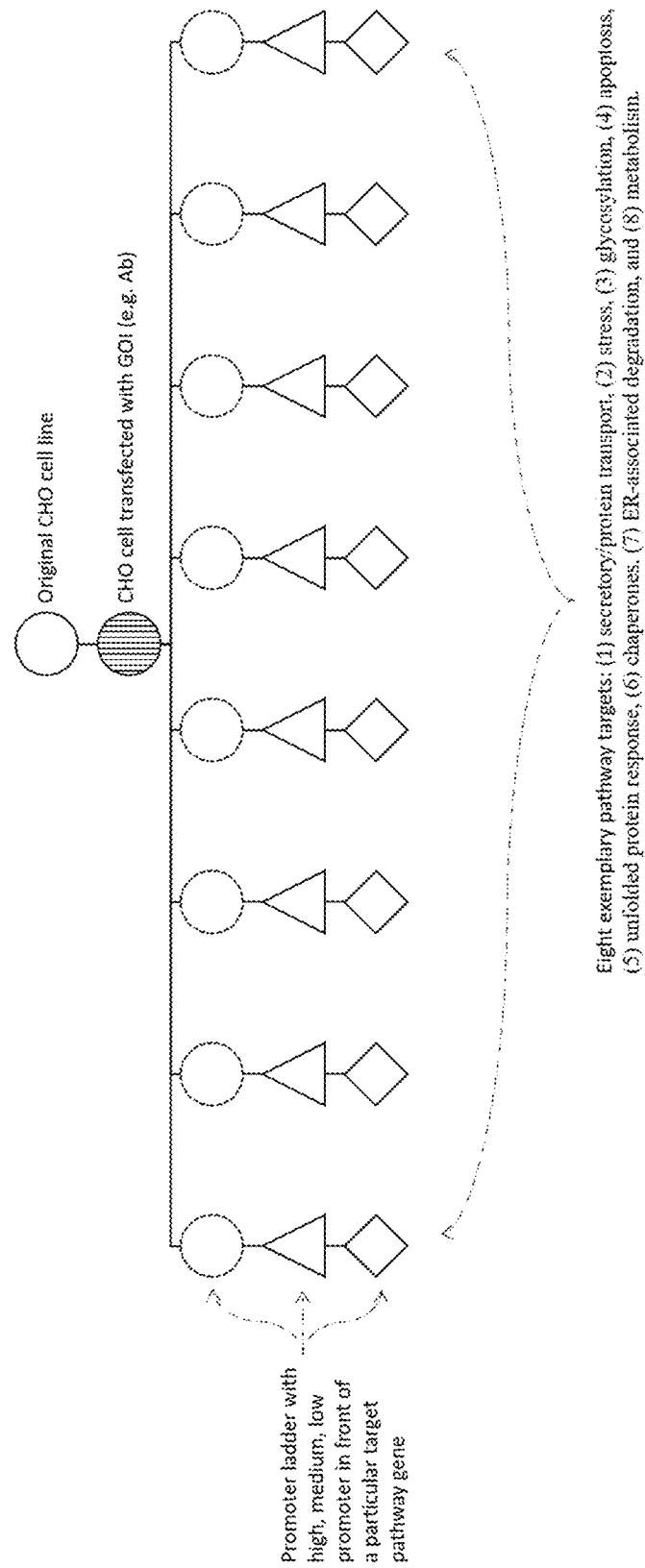
FIG. 10 illustrates an embodiment of the HTP promoter swap genomic engineering tool being utilized to probe/perturb the genomic pathways associated with therapeutic protein production. The original CHO cell line is first transfected with a gene of interest (GOI), e.g., an antibody. Once a stable antibody producing CHO cell is obtained, then target genes encoding molecules with each of the following eight representative functions are chosen: (1) secretion/protein transport, (2) stress, (3) glycosylation, (4) apoptosis, (5) unfolded protein response, (6) protein folding (e.g., chaperones), (7) ER-associated degradation, and (8) metabolism. Next, a promoter ladder with promoters exhibiting different expression profiles is operably linked to each target gene. In the illustration, the promoter ladder comprises three promoters (e.g. high, medium, and low). Consequently, for each of the target genes (eight total, one encoding a molecule of each function) a CHO cell line would be engineered to operably link a given promoter to a given target gene. Therefore, in the exemplary illustration, there would be a total of 24 unique CHO cell lines created, each having a distinct genetic construction of a particular promoter from the promoter ladder associated with the target pathway gene, but otherwise genetically identical. This allows for the effect of perturbing the particular pathway target to be observed. The effect of such promoter perturbation on the given pathway target will be examined by characterizing the expression of the gene of interest (GOI), e.g., the antibody.

The genes coding for the heavy and light chains of a model easy-to-express antibody (GOI, e.g. Herceptin, Rituximab, etc.)** are cloned into the GS vector above to obtain a mAb producing stable pools of cells. The stably selected pool are evaluated here for secreted antibody, and pool growth characteristics. In general, IgG1 and IgG4 are the easiest antibody classes to express, as they have relatively simple structures compared to other classes. However, the current disclosure is applicable to any antibody class. In FIG. 10, the original CHO cell line is represented by the open circle and the stable transfected CHO cell line expressing the GOI is depicted by the circle with interior filled lines.

Due to large clone-to-clone variability of the CHO cells, the stably transfected pool is cloned and individually evaluated for production. The phenotypic evaluation at this stage includes mAb titer, glycosylation pattern, cell growth, viability pattern during cultivation, cell densities, and specific productivity (pg mAb/cell/day).

Another concern is the stability of expression, so the clones are evaluated for stability by culturing for several generations (12-50 generations). The odds for the stability of expression can usually be increased by keeping the selection pressure (+MSX) during cultivation.

In some embodiments, the antibody heavy and light chain genes can be flanked by either FRT (or LoxP) sites. Using these recombination sites, the antibody genes can be looped out later by a specific FLP (or Cre) recombinase, creating a CHO host with no antibody genes, but carrying FRT (or LoxP) recombination sites at certain genomic loci (called "landing pads"). For future projects, the heavy and light chain genes for a different antibody can be targeted for integration to those specific landing pads, which would reduce the time and effort required during screening of the integrants.

Phase II—CRISPR-Assisted Promoter Swap of Targeted Pathway Genes

The genes encoding molecules with functions listed in Table 6, expected to influence protein expression, are targeted for the promoter swap procedure. The table also lists particular genes to be targeted for initial POC studies.

These target pathway genes are modulated with the HTP promoter swap genomic engineering tool and the effect of such gene modulation upon the aforementioned inserted GOI from Phase I is evaluated. FIG. 10 provides a schematic depiction of the example, with the promoter ladder (high, medium, low) operably linked to each of the below eight target pathway genes, which results in 24 unique CHO cell lines. These cell lines are assumed to be genetically identical, except for the unique promoter:gene target element.

The evaluation of the effect on the GOI (i.e., therapeutic protein, antibody) entails a number of Ab phenotypic characterizations, such as: titer, N-terminal cleavage, glycosylation, etc., in order to ensure the genetic perturbations did not interfere negatively with the expression of the Ab.

TABLE 6

| Target Genes | | |
|---|---|---|
| Function | Target gene | Alternative genes |
| Secretory/Protein transport | SRP14 | SRP9, SRP54 |
| Stress | XBP-1 | bcl-2, IGF1 |
| Glycosylation | COSMC | FUT8 |
| Apoptosis | BCL2 | BAK |
| Unfolded protein response | ATF6 | PERK, IRE1α |
| Protein folding (e.g., chaperones) | BiP/GRP78 (HSP70) | |
| ER-associated degradation | Dnajb9 (ERdj4/HSP40) | |
| Metabolism/Energy | LDHA | |

The CRISPR-mediated integration cassette vector consists of the following parts*

A promoter driving the expression of Marker 1 followed by a polyadenylation signal.

5' homology sequence to target integration via HDR to the target locus. The homology length can be vary typically between 100-3000 bp. In the POC studies, the homology length is targeted to be around 1000 bp.

(Optional) Markers 2 and 3 driven by their separate promoters and followed by their own polyadenylation signals, and Neomycin resistance marker to select to positive integrants. In some embodiments, these markers may be flanked by either FRT or LoxP sites, which can be used at a later stage to loopout these markers.

Promoter 4 (High/Medium/Low strength) for PROSWAP preceding the target gene to be modulated.

3' homology sequence to target integration via HDR to the target locus. The homology length can vary typically between 100-3000 bp. In the POC studies, the homology length is targeted to be around 1000 bp.

The Markers 1 and 2 are preferably fluorescent markers (GFP/RFP/mCHERRY/BFP/YFP) allowing distinction between the cells.

Off target insertions retain both markers 1 and 2, while the desired on-target insertions retain only marker 2.

Marker 3 is preferably an antibiotic selection marker (Neomycin/Puromycin/Blasticidin/Hygromycin) that only allows the growth of cells with successful integration of the heterologous cassette.

Promoter 4 is inserted upstream of the target gene to modulate its expression. The Promoter 4 could be of High, Medium, or low strength (e.g. CMV>EF1α>SV40>RSV>PGK order of relative strength, see Table 2 and FIG. 9).

In some embodiments, to completely remove the expression of the target gene, either Promoter 4, or ribosome binding site, or the translation initiation signal, is omitted from the integration cassette. Also, as aforementioned, a complete knock-out of the target gene could be utilized, or the target gene transcription could be heavily repressed with an interference technology such as CRISPRi or RNAi. The polyadenylation sequences can be chosen from SV40, hGH, BGH, and rbGlob.

The mAB producing CHO cell clone is transfected with i) Cas9 and sgRNA carrying vector to cut genomic DNA at the target locus and ii) the above integration vector carrying the positive and negative markers along with the promoter of interest. As previously stated, Cpf1 or any other appropriate CRISPR endonuclease may be used. The transfectants are seeded at a density of 1000-5000 cells/well in 96 well plates (1-10 plates per target), in media with or without Neomycin, and incubated in 37 C incubator. The MSX selection for GS (and mAB) vector are left out at this step to avoid imposing multiple selection pressure on the cells.

The CRISPR efficiencies are expected to be variable and loci-dependent. The resulting colonies (i.e. minipools) are first screened for fluorescence, and only colonies with marker 2 are screened (e.g. red fluorescent, GFP, etc.) further for integration at the target locus using PCR-amplification of the junction site and Sanger sequencing of the PCR products. The primers for the PCR can be designed to bind outside or inside of the integration cassette.

Optionally, the minipools with the correct integration are evaluated for mAb titer, glycosylation pattern, cell growth, viability pattern during cultivation, cell densities, and specific productivity (pg mAb/cell/day).

Figure 7A:
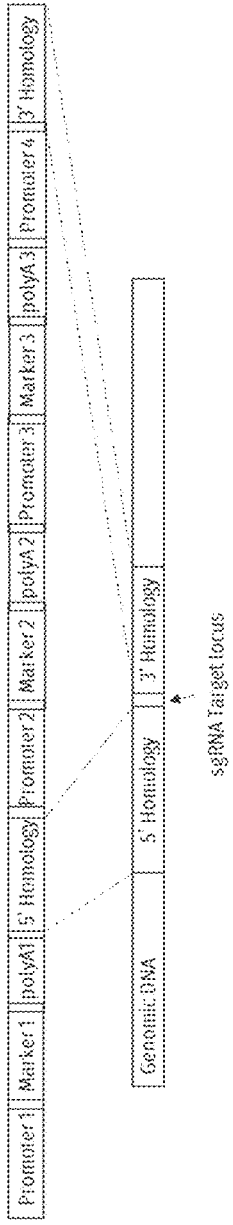
FIG. 7A, FIG. 7B and FIG. 7C illustrate various embodiments of implementing the HTP promoter swap genomic engineering tool. The DNA regions surrounding the target gene is selectively cut using a CRISPR system (or similar) gene editing approach. The promoter upstream of the target gene is replaced by Promoter 4 via homology-directed repair mechanisms. The promoter replacement cassette can be composed of various parts, which are discussed in the A-C embodiments.
Figure 7B:
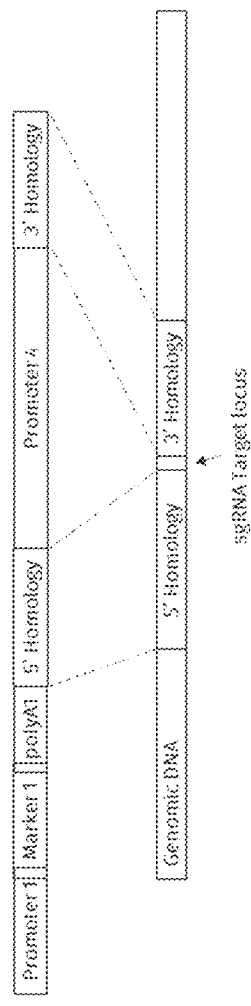
Figure 7C:
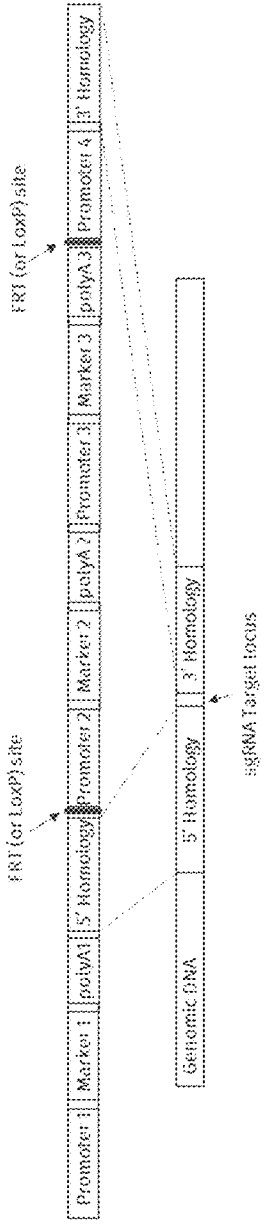
Figure 8:
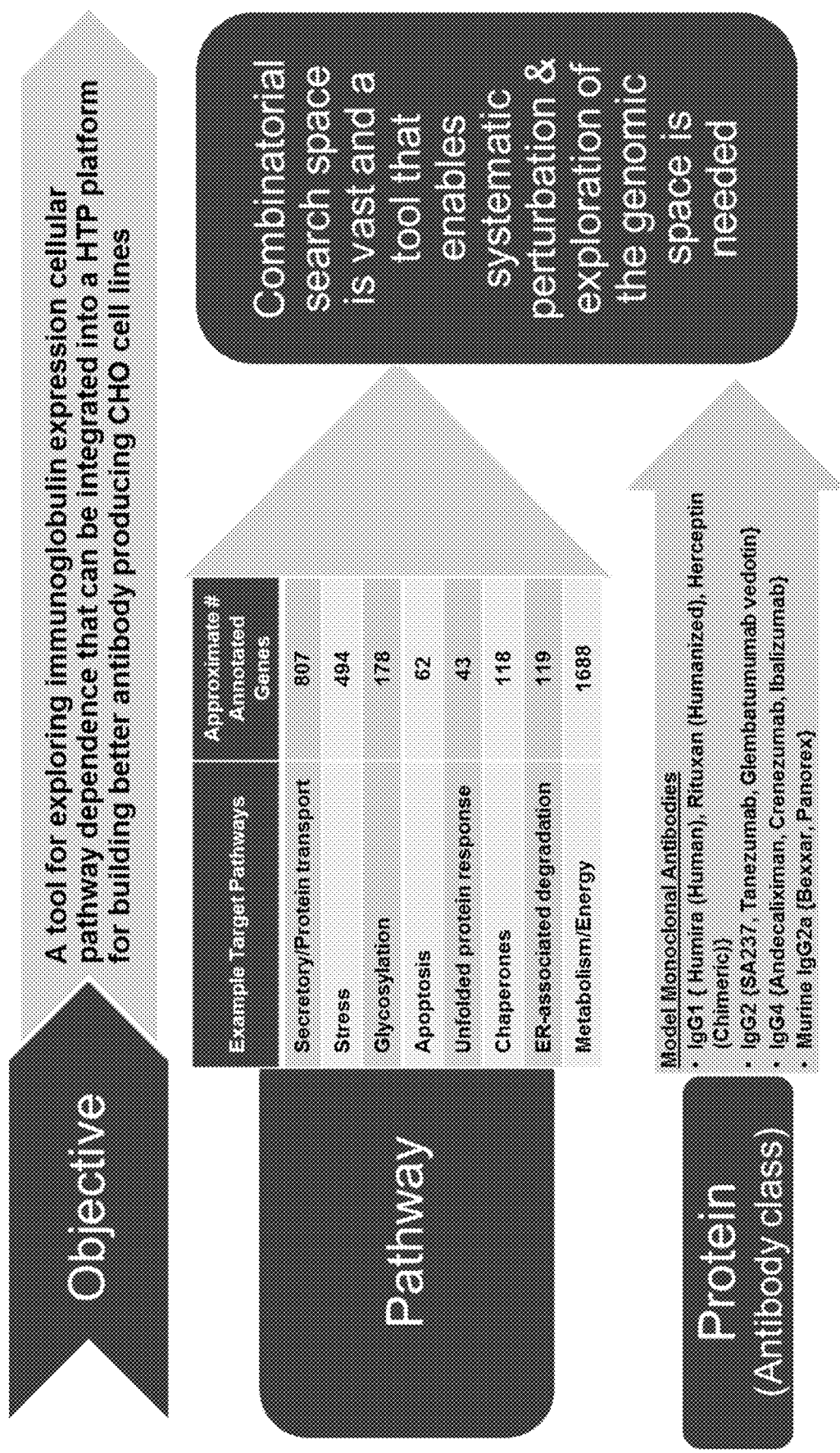
FIG. 8 provides an illustration of the objective behind the HTP promoter swap genomic engineering tool. The HTP tool allows for the systematic perturbation of cellular pathway genes, which enables one to determine the effect that such perturbation has upon a gene of interest, e.g. a therapeutic protein such as an antibody. This HTP molecular tool can be coupled with an advanced machine learning protocol and HTP cell-build factory platform, which will enable the manufacturing of better CHO cell lines for the production of antibodies.

FIG. 7A, FIG. 7B, and FIG. 7C can be referenced as an illustration of the aforementioned experimental constructs and depict various embodiments of implementing the HTP promoter swap genomic engineering tool. The DNA regions surrounding the target gene is selectively cut by sgRNA using CRISPR (or similar) gene editing approach. The promoter upstream of the target gene is replaced by Promoter 4 via homology-directed repair mechanisms. The promoter replacement cassette can be composed of various parts, for example in FIG. 7A the construct carries three markers. Marker 1 is outside the homologous region and is lost during targeted integration. It is used as a negative selection/screening marker against off-target integrations. Markers 2 and 3 are retained upon successful integration at the target locus and may be used separately for screening (fluorescent) and selection (antibiotic resistance) for rapid phenotypic analysis. In FIG. 7B, the construct carries only a negative selection/screening marker against off-target integrations. No positive markers are integrated at the target locus, allowing one to sequentially target multiple genes in a given strain. In the absence of positive markers more extensive genotyping is carried out to isolate the correctly integrated clones. And in FIG. 7C, the construct is similar to the one in the FIG. 7A embodiment with an additional feature of either FRT or LoxP recombination sites around the two positive markers 2 and 3. The presence of these recombination sites can be used to selectively loop-out the region within. This allows one to recycle these markers and allows for the sequential engineering of multiple target genes in a given strain.

Phase III—Cloning of the PROSWAP Minipools and Evaluation of Individual Clones

The minipool cultures are serially diluted and used to seed 96 well plates (1-2 per minipool) at a cell density of 0.3 cells/well to isolate singe-cell clones. The proof-of-clonality requires imaging of each well by Solentim (or similar) devices.

After growth in the 96 well plate, the colonies are expanded, banked, and evaluated for physiological properties including: mAb titer, glycosylation pattern, cell growth, viability pattern during cultivation, cell densities, and specific productivity (pg mAb/cell/day). The protein testing and characterization module (see FIG. 1) are important for ensuring that the genetic perturbations did not negatively affect the Ab's properties.

The stability of the CRISPR targeted change is also expected to be variable, and thus the top promising clones are monitored by serial culturing for ~60 generations, followed by genotyping at the target locus, as well as productivity assessment for the mAb secretion.

In embodiments where markers 2 and 3 are flanked by FRT (or LoxP) sites, a second transfection may be done with a vector carrying a FLP-recombinase (or Cre recombinase), followed by fluorescent screening for transfectants that have lost marker 2 (and marker 3). These marker-less clones can later be used for sequential PROSWAP of multiple gene targets.

Notes: *The approach is designed for the fastest strain construction and evaluation. The cells generated using this approach cannot be used as-is for a different project/antibody. The RFP (fluorescent) and Neomycin (selection) marker are included only to simplify selection during the POC experiments. These two markers can be left out in some embodiments, which would require more resources in the later genotyping to identify the correctly integrated minipools/clones as the CRISPR efficiencies are expected to vary over a wide range (1-60%). In certain embodiments, as outlined above, these markers may be flanked by FRP or LoxP recombination sites, which would require another transfection with specific recombinases (FLP or Cre recombinase) to loopout the markers at the FLP or LoxP recombination sites. **The workflow can be automated and done in parallel for multiple antibodies.

Example 3: Consolidation and Multi-Factor Combinatorial Testing of a Promoter Swap Library In this example, promoter swaps identified as having a positive effect on host performance in Example 2 are consolidated in second order combinations into new libraries.

The decision to consolidate a given promoter:gene combination is based on overall positive effect on a parameter of interest, e.g. physiological properties including mAb titer, glycosylation pattern, cell growth, viability pattern during cultivation, cell densities, and specific productivity (pg mAb/cell/day), and the likelihood that the combination would produce an additive, synergistic, or non-deleterious effect.

TABLE 7

Listing of Sequences in Sequence File

| SEQ ID NO | Description |
| --- | --- |
| 1 | CMV promoter |
| 2 | EF1α promoter |
| 3 | SV40 promoter |
| 4 | RSV promoter |
| 5 | PGK promoter |
| 6 | XP_003503464.1 SRP14 target gene encoded protein |
| 7 | NP_001230978.1 XBP-1 target gene encoded protein |
| 8 | XP_007622335.1 COSMC (C1GALT1) target gene encoded protein |
| 9 | XP_007640773.1 BCL2 target gene encoded protein |
| 10 | XP_007625847.2 ATF6 target gene encoded protein |
| 11 | NP_001233668.1 BiP/GRP78 (HSP70) target gene encoded protein |
| 12 | XP_003498044.2 Dnajb9 (ERdj4/HSP40) target gene encoded protein |
| 13 | XP_007648110.1 LDHA target gene encoded protein |
| 14 | RFP marker nucleic acid |
| 15 | RFP marker protein |
| 16 | Ds-Red2 marker nucleic acid |
| 17 | Ds-Red2 marker protein |
| 18 | eGFP marker nucleic acid |
| 19 | eGFP marker protein |
| 20 | mCHerry marker nucleic acid |
| 21 | mCHerry marker protein |
| 22 | Puromycin resistance marker nucleic acid |
| 23 | Puromycin resistance marker protein |

TABLE 7-continued

Listing of Sequences in Sequence File

| SEQ ID NO | Description |
| --- | --- |
| 24 | Neomycin resistance marker nucleic acid |
| 25 | Neomycin resistance marker protein |
| 26 | Blasticidin resistance marker nucleic acid |
| 27 | Blasticidin resistance marker protein |
| 28 | Hygromycin resistance marker nucleic acid |
| 29 | Hygromycin resistance marker protein |
| 30 | eYFP marker nucleic acid |
| 31 | eYFP marker protein |
| 32 | TagBFP marker nucleic acid |
| 33 | TagBFP marker protein |
| 34 | Cre recombinase marker nucleic acid |
| 35 | Cre marker protein |
| 36 | FLP recombinase marker nucleic acid |
| 37 | FLP recombinase marker protein |
| 38 | SV40 pA (poly A region) |
| 39 | hGH pA (poly A region) |
| 40 | BGH pA (poly A region) |
| 41 | rbGlob pA (poly A region) |
| 42 | HSV TH pA (poly A region) |
| 43 | PGK pA (poly A region) |
| 44 | SRP14 5' homology region |
| 45 | XBP-1 5' homology region |
| 46 | COSMC (C1GALT1) 5' homology region |
| 47 | BCL2 5' homology region |
| 48 | ATF6 5' homology region |
| 49 | BiP/GRP78 (HSP70) 5' homology region |
| 50 | Dnajb9 (ERdj4/HSP40) 5' homology region |
| 51 | LDHA 5' homology region |
| 52 | SRP14 3' homology region |
| 53 | XBP-1 3' homology region |
| 54 | COSMC (C1GALT1) 3' homology region |
| 55 | BCL2 3' homology region |
| 56 | ATF6 3' homology region |
| 57 | BiP/GRP78 (HSP70) 3' homology region |
| 58 | Dnajb9 (ERdj4/HSP40) 3' homology region |
| 59 | LDHA 3' homology region |
| 60 | FRT Recombination site |
| 61 | LoxP Recombination site |

NUMBERED EMBODIMENTS OF THE DISCLOSURE

Notwithstanding the appended claims, the disclosure sets forth the following numbered embodiments:

1. A HTP method for exploring immunoglobulin expression cellular pathway dependence, comprising:
   a. providing a cellular pathway target gene endogenous to a host cell and a promoter ladder comprising a plurality of promoters exhibiting different expression profiles;
   b. engineering the genome of the host cell, to create an initial promoter swap host cell library comprising a plurality of host cells, wherein the plurality of host cells comprises individual host cells comprising a unique combination of a promoter from the promoter ladder operably linked to the target gene; and
   c. screening cells of the initial promoter swap host cell library for phenotypic characteristics of an immunoglobulin of interest and/or the host cell.
2. The method of embodiment 1, wherein the host cell is a mammalian cell.
3. The method of embodiment 1, wherein the host cell is a murine cell.
4. The method of embodiment 1, wherein the host cell is a Chinese hamster ovary cell.
5. The method of embodiment 1, wherein the target gene is from a cellular pathway selected from the group consisting of: secretory, protein transport, stress, glycosylation, apoptosis, unfolded protein response, protein folding, ER-associated degradation, and metabolism.

6. The method of embodiment 1, wherein the target gene is selected from the group consisting of: SRP14, SRP9, SRP54, XBP-1, bcl-2, IGF1, COSMC, FUT8, BCL2, BAK, ATF6, PERK, IRE1α, BiP/GRP78 (HSP70), Dnajb9 (ERdj4/HSP40), and LDHA.

7. The method of embodiment 1, wherein the promoter ladder comprises at least two promoters selected from the group consisting of: CMV, EF1α, SV40, RSV, and PGK.

8. The method of embodiment 1, wherein the promoter ladder comprises at least two promoters selected from the group consisting of: SEQ ID NOs 1-5.

9. The method of embodiment 1, wherein the immunoglobulin is selected from the group consisting of: IgG, IgM, IgA, IgE, and IgD.

10. The method of embodiment 1, wherein the immunoglobulin is selected from the group consisting of: IgG1, IgG2, IgG3, and IgG4.

11. The method of embodiment 1, wherein engineering the genome of the host cell comprises utilizing a CRISPR compatible endonuclease and associated gRNA to target and cleave the host cell genome upstream of the target gene.

12. The method of embodiment 1, wherein engineering the genome of the host cell comprises utilizing a CRIPSR compatible endonuclease and associated gRNA to target and cleave the host cell genome upstream of the target gene and inserting the promoter from the promoter ladder via homologous recombination.

13. The method of embodiment 1, wherein screening cells of the initial promoter swap host cell library for phenotypic characteristics of an immunoglobulin of interest comprises ascertaining or characterizing: titer, N-terminal cleavage, and/or glycosylation patterns, of the immunoglobulin of interest.

14. The method of embodiment 1, wherein screening cells of the initial promoter swap host cell library for phenotypic characteristics of the host cell comprises ascertaining or characterizing: cell growth, cell viability pattern during cultivation, cell densities, and cell specific productivity of immunoglobulin produced per cell per day.

15. The method of embodiment 1, wherein more than one cellular pathway target gene is provided.

16. The method of embodiment 1, wherein steps a)-c) are repeated.

17. The method of embodiment 1, further comprising:
d. providing a subsequent plurality of host cells that each comprise a unique combination of genetic variation selected from the genetic variation present in at least two individual host cells screened in the preceding step, to thereby create a subsequent promoter swap host cell library.

18. The method of embodiment 1, further comprising:
d. providing a subsequent plurality of host cells that each comprise a unique combination of genetic variation selected from the genetic variation present in at least two individual host cells screened in the preceding step, to thereby create a subsequent promoter swap host cell library; and
e. screening individual host cells of the subsequent promoter swap host cell library for phenotypic characteristics of an immunoglobulin of interest and/or the host cell.

19. The method of embodiment 1, further comprising:
d. providing a subsequent plurality of host cells that each comprise a unique combination of genetic variation selected from the genetic variation present in at least two individual host cells screened in the preceding step, to thereby create a subsequent promoter swap host cell library;
e. screening individual host cells of the subsequent promoter swap host cell library for phenotypic characteristics of an immunoglobulin of interest and/or the host cell; and
f. repeating steps d)-e) one or more times.

20. A population of host cells, derived by the method of embodiment 1.

21. A HTP method for improving expression of a product of interest, comprising:
a. providing a cellular pathway target gene endogenous to a host cell and a promoter ladder comprising a plurality of promoters exhibiting different expression profiles;
b. engineering the genome of the host cell, to create an initial promoter swap host cell library comprising a plurality of host cells, wherein the plurality of host cells comprises individual host cells comprising a different promoter from the promoter ladder operably linked to the target gene; and
c. screening cells of the initial promoter swap host cell library for phenotypic characteristics of a product of interest and/or the host cell.

22. The method of embodiment 21, wherein the host cell is a mammalian cell.

23. The method of embodiment 21, wherein the host cell is a murine cell.

24. The method of embodiment 21, wherein the host cell is a Chinese hamster ovary cell.

25. The method of embodiment 21, wherein the target gene encodes a molecule with a function selected from the group consisting of: secretion, protein transport, stress response, glycosylation, apoptosis, unfolded protein response, protein folding, ER-associated degradation, and metabolism.

26. The method of embodiment 21, wherein the target gene encodes a molecule selected from the group consisting of: SRP14, SRP9, SRP54, XBP-1, bcl-2, IGF1, COSMC, FUT8, BCL2, BAK, ATF6, PERK, IRE1α, BiP/GRP78 (HSP70), Dnajb9 (ERdj4/HSP40), and LDHA.

27. The method of embodiment 21, wherein the promoter ladder comprises at least two promoters selected from the group consisting of: CMV, EF1α, SV40, RSV, and PGK.

28. The method of embodiment 21, wherein the promoter ladder comprises at least two promoters with a nucleotide sequence selected from the group consisting of: SEQ ID NOs 1-5.

29. The method of embodiment 21, wherein the product of interest is a protein.

30. The method of embodiment 21, wherein the product of interest is an immunoglobulin.

31. The method of embodiment 21, wherein the product of interest is selected from the group consisting of: IgG, IgM, IgA, IgE, and IgD.

32. The method of embodiment 21, wherein the product of interest is selected from the group consisting of: IgG1, IgG2, IgG3, and IgG4.
33. The method of embodiment 21, wherein engineering the genome of the host cell comprises utilizing a CRISPR compatible endonuclease and associated gRNA to target and cleave the host cell genome upstream of the target gene.
34. The method of embodiment 33, further comprising inserting a promoter from the promoter ladder via homologous recombination.
35. The method of embodiment 21, wherein screening cells of the initial promoter swap host cell library for phenotypic characteristics of a product of interest comprises ascertaining or characterizing: titer, N-terminal cleavage, and/or glycosylation patterns of the product of interest.
36. The method of embodiment 21, wherein screening cells of the initial promoter swap host cell library for phenotypic characteristics of the host cell comprises ascertaining or characterizing one or more of the following: cell growth, cell viability pattern during cultivation, cell densities, and cell specific productivity of a product of interest produced per cell per day.
37. The method of embodiment 21, wherein more than one cellular pathway target gene is provided.
38. The method of embodiment 21, wherein steps a)-c) are repeated.
39. The method of embodiment 21, further comprising:
    d. providing a subsequent plurality of host cells that each comprise a unique combination of genetic variation selected from the genetic variation present in at least two individual host cells screened in the preceding step, to thereby create a subsequent promoter swap host cell library.
40. The method of embodiment 21, further comprising:
    d. providing a subsequent plurality of host cells that each comprise a unique combination of genetic variation selected from the genetic variation present in at least two individual host cells screened in the preceding step, to thereby create a subsequent promoter swap host cell library; and
    e. screening individual host cells of the subsequent promoter swap host cell library for phenotypic characteristics of a product of interest and/or the host cell.
41. The method of embodiment 21, further comprising:
    d. providing a subsequent plurality of host cells that each comprise a unique combination of genetic variation selected from the genetic variation present in at least two individual host cells screened in the preceding step, to thereby create a subsequent promoter swap host cell library;
    e. screening individual host cells of the subsequent promoter swap host cell library for phenotypic characteristics of a product of interest and/or the host cell; and
    f. repeating steps d)-e) one or more times.
42. A population of host cells, derived by the method of embodiment 21.
43. A product of interest produced by a host cell from the population of host cells in embodiment 42.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. To this end, U.S. application Ser. No. 15/396,230 (U.S. Pub. No. US 2017/0159045 A1), U.S. application Ser. No. 15/140,296 (U.S. Pub. No. US 2017/0316353 A1), and PCT/US2016/065464 (WO 2017/100376 A2) are all incorporated herein by reference.

What is claimed is:

1. A high-throughput (HTP) method for immunoglobulin expression, comprising:
   (a) selecting at least one cellular pathway target gene that is endogenous to a host cell, wherein the target gene encodes a molecule selected from the group consisting of: signaling receptor protein 14 (SRP14), signaling receptor protein 9 (SRP9), signaling recognition particle 54 (SRP54), X-box binding protein 1 (XBP-1), b-cell lymphoma 2 (bcl-2), insulin-like growth factor 1 (IGF1), C1GALT1-specific chaperone (COSMC), alpha-1,6-fucosyltransferase 8 (FUT8), BCL2 antagonist/killer (BAK), activating transcription factor 6 (ATF6), eukaryotic translation initiation factor 2 alpha kinase 3 (PERK), inositol requiring enzyme 1 α (IRE1α), heat shock 70 kDa protein 5 (BiP/GRP78), DNA heat shock protein family member B9 (Dnajb9), and lactate dehydrogenase A (LDHA);
   (b) providing a promoter ladder comprising a plurality of promoters exhibiting different expression profiles;
   (c) engineering the genome of the host cell by operably linking a promoter from the promoter ladder to the target gene in the genome of the host cell;
   (d) repeating step (c) with additional host cells to create an initial promoter swap host cell library comprising a plurality of host cells, wherein the plurality of host cells comprises individual host cells comprising a different promoter from the promoter ladder operably linked to the target gene in the genome of each host cell; and
   (e) screening cells of the initial promoter swap host cell library for phenotypic characteristics of an expressed immunoglobulin of interest and/or the host cell.

2. The method of claim 1, wherein the host cell is a mammalian cell.

3. The method of claim 1, wherein the host cell is a Chinese hamster ovary cell.

4. The method of claim 1, wherein the target gene encodes a molecule with a function selected from the group consisting of: secretion, protein transport, stress response, glycosylation, apoptosis, unfolded protein response, protein folding, ER-associated degradation, and metabolism.

5. The method of claim 1, wherein the promoter ladder comprises at least two promoters selected from the group consisting of: cytomegalovirus immediate-early promoter (CMV), human elongation factor 1α promoter (EF1α), simian virus 40 early promoter (SV40), rous sarcoma virus long terminal repeat promoter (RSV), and mouse phosphoglycerate kinase 1 promoter (PGK).

6. The method of claim 1, wherein the promoter ladder comprises at least two promoters with a nucleotide sequence selected from the group consisting of: SEQ ID NOs 1-5.

7. The method of claim 1, wherein the immunoglobulin (Ig) is selected from the group consisting of: IgG, IgM, IgA, IgE, and IgD.

8. The method of claim 1, wherein the immunoglobulin is selected from the group consisting of: IgG1, IgG2, IgG3, and IgG4.

9. The method of claim 1, wherein engineering the genome of the host cell comprises utilizing a Clustered Regularly Interspaced Short Palindromic Repeats (CRISPR) system compatible endonuclease and associated guide RNA (gRNA) to target and cleave the host cell genome upstream of the target gene.

10. The method of claim 9, further comprising inserting a promoter from the promoter ladder via homologous recombination.

11. The method of claim 1, wherein screening cells of the initial promoter swap host cell library for phenotypic characteristics of an expressed immunoglobulin of interest comprises ascertaining or characterizing one or more of the following: titer, N-terminal cleavage, and/or glycosylation patterns of the immunoglobulin of interest; or cell growth, cell viability pattern during cultivation, cell densities, and cell/or specific productivity of immunoglobulin produced per cell per day.

12. The method of claim 1, wherein steps (a)-(e) are repeated.

13. The method of claim 1, further comprising:
(f) providing a subsequent plurality of host cells that each comprise unique combinations of a promoter and a target gene screened in the preceding step, to thereby create a subsequent promoter swap host cell library; and
(g) screening individual host cells of the subsequent promoter swap host cell library for phenotypic characteristics of an expressed immunoglobulin of interest and/or the host cell.

14. A HTP method for expression of a product of interest, comprising:
(a) selecting at least one cellular pathway target gene that is endogenous to a host cell, wherein the target gene encodes a molecule selected from the group consisting of: SRP14, SRP9, SRP54, XBP-1, bcl-2, IGF1, COSMC, FUT8, BAK, ATF6, PERK, IRE1α, BiP/GRP78, Dnajb9, and LDHA;
(b) providing a promoter ladder comprising a plurality of promoters exhibiting different expression profiles;
(c) engineering the genome of the host cell by operably linking a promoter from the promoter ladder to the target gene in the genome of the host cell;
(d) repeating step (c) with additional host cells to create an initial promoter swap host cell library comprising a plurality of host cells, wherein the plurality of host cells comprises individual host cells comprising a different promoter from the promoter ladder operably linked to the target gene in the genome of the host cell; and
(e) screening cells of the initial promoter swap host cell library for phenotypic characteristics of an expressed product of interest and/or the host cell.

15. The method of claim 14, wherein the host cell is a mammalian cell.

16. The method of claim 14, wherein the host cell is a murine cell.

17. The method of claim 14, wherein the host cell is a Chinese hamster ovary cell.

18. The method of claim 14, wherein the target gene encodes a molecule with a function selected from the group consisting of: secretion, protein transport, stress response, glycosylation, apoptosis, unfolded protein response, protein folding, ER-associated degradation, and metabolism.

19. The method claim 14, wherein the promoter ladder comprises at least two promoters selected from the group consisting of: CMV, EF1α, SV40, RSV, and PGK.

20. The method of claim 14, wherein the promoter ladder comprises at least two promoters with a nucleotide sequence selected from the group consisting of: SEQ ID NOs 1-5.

21. The method of claim 14, wherein the product of interest is a protein.

22. The method of claim 14, wherein engineering the genome of the host cell comprises utilizing a CRISPR compatible endonuclease and associated gRNA to target and cleave the host cell genome upstream of the target gene.

23. The method of claim 14, further comprising inserting a promoter from the promoter ladder via homologous recombination.

24. The method of claim 14, wherein screening cells of the initial promoter swap host cell library for phenotypic characteristics of an expressed product of interest comprises ascertaining or characterizing one or more of the following: titer, N-terminal cleavage, glycosylation patterns of the product of interest; or cell growth, cell viability pattern during cultivation, cell densities, and/or cell specific productivity of a product of interest produced per cell per day.

25. The method of claim 14, wherein steps (a)-(e) are repeated.

26. The method of claim 14, further comprising:
(f) providing a subsequent plurality of host cells that each comprise unique combinations of a promoter and a target gene screened in the preceding step, to thereby create a subsequent promoter swap host cell library; and
(g) screening individual host cells of the subsequent promoter swap host cell library for phenotypic characteristics of an expressed product of interest and/or the host cell.

* * * * *

SEQUENCE LISTING

```
<160> NUMBER OF SEQ ID NOS: 61

<210> SEQ ID NO 1
<211> LENGTH: 508
<212> TYPE: DNA
<213> ORGANISM: Unknown
<220> FEATURE:
<223> OTHER INFORMATION: Cytomegalovirus sp.

<400> SEQUENCE: 1
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catggtgatg cggttttggc agtacatcaa tgggcgtgga tagcggtttg actcacgggg     360
atttccaagt ctccacccca ttgacgtcaa tgggagtttg ttttggcacc aaaatcaacg     420
ggactttcca aatgtcgta acaactccgc cccattgacg caaatgggcg gtaggcgtgt      480
acggtgggag gtctatataa gcagagct                                        508
```

```
<210> SEQ ID NO 2
<211> LENGTH: 1179
<212> TYPE: DNA
<213> ORGANISM: Homo sapiens

<400> SEQUENCE: 2
ggctccggtg cccgtcagtg ggcagagcgc acatcgccca cagtccccga gaagttgggg      60
ggaggggtcg gcaattgaac cggtgcctag agaaggtggc gcggggtaaa ctgggaaagt     120
gatgtcgtgt actggctccg ccttttttccc gagggtgggg gagaaccgta tataagtgca    180
gtagtcgccg tgaacgttct ttttcgcaac gggtttgccg ccagaacaca ggtaagtgcc     240
gtgtgtggtt cccgcgggcc tggcctcttt acgggttatg gcccttgcgt gccttgaatt     300
acttccacct ggctgcagta cgtgattctt gatcccgagc ttcgggttgg aagtgggtgg     360
gagagttcga ggccttgcgc ttaaggagcc ccttcgcctc gtgcttgagt tgaggcctgg     420
cctgggcgct ggggccgccg cgtgcgaatc tggtggcacc ttcgcgcctg tctcgctgct     480
ttcgataagt ctctagccat ttaaaatttt tgatgacctg ctgcgacgct ttttttctgg     540
caagatagtc ttgtaaatgc gggccaagat ctgcacactg gtatttcggt ttttggggcc     600
gcgggcggcg acggggcccg tgcgtcccag cgcacatgtt cggcgaggcg ggcctgcga      660 gcgcggccac cgagaatcgg acggggtag tctcaagctg gccggcctgc tctggtgcct      720
ggcctcgcgc cgccgtgtat cgccccgccc tgggcggcaa ggctggcccg gtcggcacca    780
gttgcgtgag cggaaagatg gccgcttccc ggccctgctg cagggagctc aaaatggagg    840
acgcggcgct cgggagagcg ggcgggtgag tcacccacac aaaggaaaag ggccttccg     900 tcctcagccg tcgcttcatg tgactccacg gagtaccggg cgccgtccag gcacctcgat    960
tagttctcga gcttttggag tacgtcgtct ttaggttggg gggaggggtt ttatgcgatg    1020
gagtttcccc acactgagtg ggtggagact gaagttaggc cagctggca cttgatgtaa    1080 ttctccttgg aatttgccct ttttgagttt ggatcttggt tcattctcaa gcctcagaca    1140
gtggttcaaa gttttttttct tccatttcag gtgtcgtga                          1179

<210> SEQ ID NO 3
<211> LENGTH: 281
<212> TYPE: DNA
<213> ORGANISM: Simian virus 40

<400> SEQUENCE: 3
tgtgtcagtt agggtgtgga aagtccccag gctccccagc aggcagaagt atgcaaagca      60
tgcatctcaa ttagtcagca accaggtgtg gaaagtcccc aggctcccca gcaggcagaa    120
gtatgcaaag catgcatctc aattagtcag caaccatagt cccgccccta actccgccca    180
tcccgcccct aactccgccc agttccgccc attctccgcc ccatggctga ctaattttttt    240 ttatttatgc agaggccgag gccgcctctg cctctgagct a                          281

<210> SEQ ID NO 4
<211> LENGTH: 262
<212> TYPE: DNA
<213> ORGANISM: Rous sarcoma virus

<400> SEQUENCE: 4
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga    120
```

```
tcgtgcctta ttaggaaggc aacagacggg tctgacatgg attggacgaa ccactgaatt    180
ccgcattgca gagatattgt atttaagtgc ctagctcgat acaataaacg ccatttgacc    240
attcaccaca ttggtgtgca cc                                             262
```

<210> SEQ ID NO 5
<211> LENGTH: 500
<212> TYPE: DNA
<213> ORGANISM: Unknown
<220> FEATURE:
<223> OTHER INFORMATION: Mus sp.

<400> SEQUENCE: 5

```
gggtagggga ggcgcttttc ccaaggcagt ctggagcatg cgctttagca gccccgctgg     60
gcacttggcg ctacacaagt ggcctctggc ctcgcacaca ttccacatcc accggtaggc    120
gccaaccggc tccgttcttt ggtggcccct cgcgccacc ttctactcct ccctagtca    180 ggaagttccc ccccgccccg cagctcgcgt cgtgcaggac gtgacaaatg aagtagcac    240 gtctcactag tctcgtgcag atggacagca ccgctgagca atggaagcgg gtaggccttt    300
ggggcagcgg ccaatagcag ctttgctcct tcgctttctg ggctcagagg ctgggaaggg    360
gtgggtccgg gggcgggctc aggggcgggc tcaggggcgg ggcgggcgcc cgaaggtcct    420
ccggaggccc ggcattctgc acgcttcaaa agcgcacgtc tgccgcgctg ttctcctctt    480
cctcatctcc gggcctttcg                                                500
```

<210> SEQ ID NO 6
<211> LENGTH: 110
<212> TYPE: PRT
<213> ORGANISM: Cricetulus griseus

<400> SEQUENCE: 6

```
Met Val Leu Leu Glu Ser Glu Gln Phe Leu Thr Glu Leu Thr Arg Leu
1               5                   10                  15

Phe Gln Lys Cys Arg Ser Ser Gly Ser Val Tyr Ile Thr Leu Lys Lys
            20                  25                  30

Tyr Asp Gly Arg Thr Lys Pro Thr Pro Arg Lys Ser Ala Val Glu Ser
        35                  40                  45

Val Glu Pro Ala Glu Asn Lys Cys Leu Leu Arg Ala Thr Asp Gly Lys
    50                  55                  60

Arg Lys Ile Ser Thr Val Ser Ser Lys Glu Val Asn Lys Phe Gln
65                  70                  75                  80

Met Ala Tyr Ser Asn Leu Leu Arg Ala Asn Met Asp Gly Leu Lys Lys
            85                  90                  95

Arg Asp Lys Lys Asn Lys Ser Lys Lys Thr Lys Pro Ala Gln
            100                 105                 110
```

<210> SEQ ID NO 7
<211> LENGTH: 370
<212> TYPE: PRT
<213> ORGANISM: Cricetulus griseus

<400> SEQUENCE: 7

```
Met Val Val Val Ala Ala Ser Pro Ser Ala Ala Thr Ala Ala Pro Lys
1               5                   10                  15

Val Leu Leu Leu Ser Gly Gln Pro Ala Ala Asp Gly Arg Ala Leu Pro
            20                  25                  30

Leu Met Val Pro Gly Ser Arg Ala Ala Gly Ser Glu Ala Asn Gly Ala
        35                  40                  45
```

Pro Gln Ala Arg Lys Arg Gln Arg Leu Thr His Leu Ser Pro Glu Glu
    50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn Gln Lys Leu Leu Leu Glu Asn Gln Leu Leu
            100                 105                 110

Arg Glu Lys Thr His Gly Leu Val Ile Glu Asn Gln Glu Leu Arg Thr
        115                 120                 125

Arg Leu Gly Met Asp Val Leu Thr Thr Glu Glu Ala Pro Glu Thr Glu
    130                 135                 140

Ser Lys Gly Asn Gly Val Arg Pro Val Ala Gly Ser Ala Glu Ser Ala
145                 150                 155                 160

Ala Gly Ala Gly Pro Val Val Thr Ser Pro Glu His Leu Pro Met Asp
                165                 170                 175

Ser Asp Thr Val Asp Ser Ser Asp Ser Glu Ser Asp Ile Leu Leu Gly
            180                 185                 190

Ile Leu Asp Lys Leu Asp Pro Val Met Phe Phe Lys Cys Pro Ser Pro
        195                 200                 205

Glu Ser Ala Asn Leu Glu Glu Leu Pro Glu Val Tyr Pro Gly Pro Ser
    210                 215                 220

Ser Leu Pro Ala Ser Leu Ser Leu Ser Val Gly Thr Ser Ser Ala Lys
225                 230                 235                 240

Leu Glu Ala Ile Asn Glu Leu Ile Arg Phe Asp His Val Tyr Thr Lys
                245                 250                 255

Pro Leu Val Leu Glu Ile Pro Ser Glu Thr Glu Ser Gln Thr Asn Val
            260                 265                 270

Val Val Lys Ile Glu Glu Ala Pro Leu Ser Ser Ser Glu Glu Asp His
        275                 280                 285

Pro Glu Phe Ile Val Ser Val Lys Lys Glu Pro Leu Glu Glu Asp Phe
    290                 295                 300

Ile Pro Glu Pro Gly Ile Ser Asn Leu Leu Ser Ser Ser His Cys Leu
305                 310                 315                 320

Lys Pro Ser Ser Cys Leu Leu Asp Ala Tyr Ser Asp Cys Gly Tyr Glu
                325                 330                 335

Gly Ser Pro Ser Pro Phe Ser Asp Met Ser Ser Pro Leu Gly Ile Asp
            340                 345                 350

His Ser Trp Glu Asp Thr Phe Ala Asn Glu Leu Phe Pro Gln Leu Ile
        355                 360                 365

Ser Val
    370

<210> SEQ ID NO 8
<211> LENGTH: 318
<212> TYPE: PRT
<213> ORGANISM: Cricetulus griseus

<400> SEQUENCE: 8

Met Leu Ser Glu Ser Ser Ser Phe Leu Lys Gly Val Met Leu Gly Ser
1               5                   10                  15

Ile Phe Tyr Ala Leu Ile Thr Thr Leu Gly His Ile Arg Ile Gly His
            20                  25                  30

Arg Asn Arg Thr His His His Glu His His His Leu Gln Ala Pro Asn

```
                35                  40                  45
Lys Glu Asp Ile Ser Lys Ile Ser Ala Ala Glu Arg Met Glu Leu Ser
 50                  55                  60
Lys Ser Phe Arg Val Tyr Cys Ile Val Leu Val Lys Pro Lys Asp Val
 65                  70                  75                  80
Ser Leu Trp Ala Ala Val Lys Glu Thr Trp Thr Lys His Cys Asp Lys
                 85                  90                  95
Ala Glu Phe Phe Ser Ser Glu Asn Val Lys Val Phe Glu Ser Ile Asn
                100                 105                 110
Val Asp Thr Asp Asp Met Trp Leu Met Met Arg Lys Ala Tyr Lys Tyr
                115                 120                 125
Ala Phe Asp Lys Tyr Lys Glu Gln Tyr Asn Trp Phe Phe Leu Ala Arg
                130                 135                 140
Pro Ser Thr Phe Ala Val Ile Glu Asn Leu Lys Tyr Phe Leu Leu Lys
145                 150                 155                 160
Lys Asp Pro Ser Gln Pro Phe Tyr Leu Gly His Thr Val Lys Ser Gly
                165                 170                 175
Asp Leu Glu Tyr Val Ser Val Asp Gly Gly Ile Val Leu Ser Ile Glu
                180                 185                 190
Ser Met Lys Arg Leu Asn Ser Leu Leu Ser Val Pro Glu Lys Cys Pro
                195                 200                 205
Glu Gln Gly Gly Met Ile Trp Lys Ile Ser Asp Lys Gln Leu Ala
                210                 215                 220
Val Cys Leu Lys Tyr Ala Gly Val Phe Ala Glu Asn Ala Glu Asp Ala
225                 230                 235                 240
Asp Arg Lys Asp Val Phe Asn Thr Lys Ser Val Gly Leu Phe Ile Lys
                245                 250                 255
Glu Ala Met Ser Asn His Pro Asn Gln Val Val Glu Gly Cys Cys Ser
                260                 265                 270
Asn Met Ala Val Thr Phe Asn Gly Leu Thr Pro Asn Gln Met His Val
                275                 280                 285
Met Met Tyr Gly Val Tyr Arg Leu Arg Ala Phe Gly His Val Phe Asn
                290                 295                 300
Asp Ala Leu Val Phe Leu Pro Pro Asn Gly Ser Asp Asn Asp
305                 310                 315

<210> SEQ ID NO 9
<211> LENGTH: 203
<212> TYPE: PRT
<213> ORGANISM: Cricetulus griseus

<400> SEQUENCE: 9

Met Ala Gln Ala Gly Arg Thr Gly Tyr Asp Asn Arg Glu Ile Val Met
  1               5                  10                  15
Lys Tyr Ile His Tyr Lys Leu Ser Gln Arg Gly Tyr Glu Trp Asp Val
                 20                  25                  30
Gly Asp Val Asp Ala Ala Pro Leu Gly Ala Ala Pro Thr Pro Gly Ile
                 35                  40                  45
Phe Ser Phe Gln Pro Glu Ser Asn Pro Thr Pro Ala Val His Arg Asp
 50                  55                  60
Met Ala Ala Arg Thr Ser Pro Leu Arg Pro Ile Val Ala Thr Thr Gly
 65                  70                  75                  80
Pro Thr Leu Ser Pro Val Pro Pro Val Val His Leu Thr Leu Arg Arg
                 85                  90                  95
```

```
Ala Gly Asp Asp Phe Ser Arg Arg Tyr Arg Arg Asp Phe Ala Glu Met
            100                 105                 110
Ser Ser Gln Leu His Leu Thr Pro Phe Thr Ala Arg Gly Arg Phe Ala
        115                 120                 125
Thr Val Val Glu Glu Leu Phe Arg Asp Gly Val Asn Trp Gly Arg Ile
    130                 135                 140
Val Ala Phe Phe Glu Phe Gly Gly Val Met Cys Val Glu Ser Val Asn
145                 150                 155                 160
Arg Glu Met Ser Pro Leu Val Asp Asn Ile Ala Leu Trp Met Thr Glu
                165                 170                 175
Tyr Leu Asn Arg His Leu His Thr Trp Ile Gln Asp Asn Gly Gly Trp
            180                 185                 190
Leu Met Cys Ser Glu Asp Ser Ala Ser Pro Gln
        195                 200

<210> SEQ ID NO 10
<211> LENGTH: 766
<212> TYPE: PRT
<213> ORGANISM: Cricetulus griseus

<400> SEQUENCE: 10

Met Thr Leu Ser Val Thr Thr Ser Leu Ala Gly Ser Val Gly Ala Thr
1               5                   10                  15
Arg Asn Gln Pro Arg Asp Ile Gly Ser Pro Cys Cys His Ala Arg Leu
            20                  25                  30
Gly Glu Ala Gly Val Gly Asn Phe Leu Val Ala Asp Pro Gly Val Ile
        35                  40                  45
Ala Leu Gln Gln Met Thr Ala Asn Leu Trp Ala Ser Pro Phe Ala Ser
    50                  55                  60
Ala Arg Pro Pro Ser Val Ser Val Pro Gln Ile Leu Ser Ala Gly Arg
65                  70                  75                  80
Arg Arg Phe Gly Leu Leu Thr Asp Pro Ser Glu Gly Glu Ala Ser
                85                  90                  95
Val Trp Arg Lys Pro Ala Gly Ala Ala Gly Thr Met Glu Ser Pro Phe
                100                 105                 110
Ser Pro Gly Phe Pro His Gly Pro Glu Glu Asp Trp Glu Ser Thr Leu
            115                 120                 125
Phe Ala Glu Leu Gly Tyr Phe Thr Asp Asn Asp Glu Val Gln Phe Asp
    130                 135                 140
Ala Ala Asn Glu Thr Tyr Glu Asn Asn Phe Asp His Leu Asn Phe Asp
145                 150                 155                 160
Leu Asp Leu Met Pro Trp Glu Ser Asp Ile Trp Ser Ser Ser His
                165                 170                 175
Phe Cys Ser Val Lys Asp Ile Lys Ala Glu Pro Gln Pro Leu Ser Pro
            180                 185                 190
Ala Ser Ser Cys Ser Val Ser Pro Arg Ser Val Asp Ser Cys
        195                 200                 205
Ser Ser Thr Gln His Val Pro Glu Glu Leu Asp Leu Ser Ser Ser Ser
    210                 215                 220
Gln Ser Pro Leu Ser Leu Tyr Gly Glu Ser Cys Asn Ser Pro Ser Ser
225                 230                 235                 240
Val Glu Pro Leu Lys Glu Asp Lys Pro Val Ile Gly Pro Gly Asn Lys
                245                 250                 255
Thr Glu His Gly Leu Thr Pro Lys Lys Lys Asn Gln Met Ser Ser Lys
            260                 265                 270
```

```
Pro Ser Val Gln Pro Lys Pro Leu Leu Pro Ala Ala Pro Lys Thr
        275                 280                 285

Gln Thr Asn Ala Gly Val Pro Ala Lys Thr Ile Ile Ile Gln Thr Leu
    290                 295                 300

Pro Ala Leu Met Pro Leu Ala Lys Gln Gln Ser Ser Ile Ile Ser Ile
305                 310                 315                 320

Gln Pro Ala Pro Thr Lys Gly Gln Thr Val Leu Leu Ser Gln Pro Ala
                325                 330                 335

Val Val Gln Leu Gln Ala Pro Gly Val Leu Pro Ser Ala Gln Pro Val
                340                 345                 350

Leu Ala Val Ala Gly Gly Ala Thr Gln Leu Pro Asn His Val Val Asn
                355                 360                 365

Val Val Pro Ala Pro Val Val Asn Ser Pro Val Asn Gly Lys Leu Ser
            370                 375                 380

Met Thr Lys Pro Val Leu Gln Ser Thr Thr Arg Ser Val Gly Ser Asp
385                 390                 395                 400

Ile Ala Val Leu Arg Arg Gln Gln Arg Met Ile Lys Asn Arg Glu Ser
                    405                 410                 415

Ala Cys Gln Ser Arg Lys Lys Lys Lys Glu Tyr Met Leu Gly Leu Glu
                420                 425                 430

Ala Arg Leu Lys Ala Ala Leu Ser Glu Asn Glu Gln Leu Lys Lys Glu
                435                 440                 445

Asn Gly Ser Leu Lys Arg Gln Leu Asp Glu Val Val Ser Glu Asn Gln
            450                 455                 460

Arg Leu Lys Val Pro Ser Pro Lys Arg Arg Ala Val Cys Val Met Ile
465                 470                 475                 480

Val Leu Ala Phe Ile Met Leu Asn Tyr Gly Pro Met Ser Met Leu Glu
                485                 490                 495

Gln Asp Ser Arg Arg Val Lys Pro Ser Val Asn Pro Ala Asn Gln Arg
                500                 505                 510

Arg His Leu Leu Glu Phe Ser Ala Lys Glu Val Glu Asp Thr Ser Asp
        515                 520                 525

Asp Ile Asn Gln Lys Asn Ser Tyr Arg Tyr Asp His Ser Val Ser Asn
            530                 535                 540

Asp Lys Ala Leu Met Val Leu Thr Glu Glu Pro Leu Leu Tyr Ile Pro
545                 550                 555                 560

Pro Pro Pro Cys Gln Pro Leu Ile Asn Thr Thr Glu Ser Leu Arg Leu
                565                 570                 575

Asn His Glu Leu Arg Gly Trp Val His Arg His Glu Val Glu Arg Thr
            580                 585                 590

Lys Ser Arg Arg Met Ile Asn Asn Gln Gln Lys Thr Arg Ile Leu Gln
            595                 600                 605

Gly Ala Leu Glu Gln Gly Ser Asn Ser Gln Leu Met Ala Val Gln Tyr
        610                 615                 620

Thr Glu Thr Thr Ser Ile Ser Arg Asn Ser Gly Asn Glu Leu Gln Val
625                 630                 635                 640

Tyr Tyr Ala Ser Pro Gly Ser Tyr Gln Gly Phe Phe Glu Ala Ile Arg
                645                 650                 655

Arg Arg Gly Asp Thr Phe Tyr Val Val Ser Phe Arg Arg Asp His Leu
                660                 665                 670

Leu Leu Pro Ala Thr Thr His Asn Lys Thr Thr Arg Pro Lys Met Ser
            675                 680                 685
```

```
Ile Val Leu Pro Ala Ile Asn Ile Asn Asp Asn Val Ile Asn Gly Gln
    690                 695                 700
Asp Tyr Glu Val Met Met Gln Ile Asp Cys Gln Val Met Asp Thr Arg
705                 710                 715                 720
Ile Leu His Ile Lys Ser Ser Ser Val Pro Pro Tyr Leu Arg Asp His
                725                 730                 735
Gln Arg Asn Gln Thr Asn Thr Phe Phe Gly Ser Pro Pro Thr Ala Thr
                740                 745                 750
Glu Thr Thr His Val Val Ser Thr Ile Pro Glu Ser Leu Gln
                755                 760                 765

<210> SEQ ID NO 11
<211> LENGTH: 654
<212> TYPE: PRT
<213> ORGANISM: Cricetulus griseus

<400> SEQUENCE: 11

Met Lys Phe Pro Met Val Ala Ala Ala Leu Leu Leu Cys Ala Val
1               5                   10                  15
Arg Ala Glu Glu Glu Asp Lys Lys Glu Asp Val Gly Thr Val Val Gly
                20                  25                  30
Ile Asp Leu Gly Thr Thr Tyr Ser Cys Val Gly Val Phe Lys Asn Gly
                35                  40                  45
Arg Val Glu Ile Ile Ala Asn Asp Gln Gly Asn Arg Ile Thr Pro Ser
50                  55                  60
Tyr Val Ala Phe Thr Pro Glu Gly Glu Arg Leu Ile Gly Asp Ala Ala
65                  70                  75                  80
Lys Asn Gln Leu Thr Ser Asn Pro Glu Asn Thr Val Phe Asp Ala Lys
                85                  90                  95
Arg Leu Ile Gly Arg Thr Trp Asn Asp Pro Ser Val Gln Gln Asp Ile
                100                 105                 110
Lys Phe Leu Pro Phe Lys Val Val Glu Lys Lys Thr Lys Pro Tyr Ile
                115                 120                 125
Gln Val Asp Ile Gly Gly Gly Gln Thr Lys Thr Phe Ala Pro Glu Glu
                130                 135                 140
Ile Ser Ala Met Val Leu Thr Lys Met Lys Glu Thr Ala Glu Ala Tyr
145                 150                 155                 160
Leu Gly Lys Lys Val Thr His Ala Val Val Thr Val Pro Ala Tyr Phe
                165                 170                 175
Asn Asp Ala Gln Arg Gln Ala Thr Lys Asp Ala Gly Thr Ile Ala Gly
                180                 185                 190
Leu Asn Val Met Arg Ile Ile Asn Glu Pro Thr Ala Ala Ala Ile Ala
                195                 200                 205
Tyr Gly Leu Asp Lys Arg Glu Gly Glu Lys Asn Ile Leu Val Phe Asp
                210                 215                 220
Leu Gly Gly Gly Thr Phe Asp Val Ser Leu Leu Thr Ile Asp Asn Gly
225                 230                 235                 240
Val Phe Glu Val Val Ala Thr Asn Gly Asp Thr His Leu Gly Gly Glu
                245                 250                 255
Asp Phe Asp Gln Arg Val Met Glu His Phe Ile Lys Leu Tyr Lys Lys
                260                 265                 270
Lys Thr Gly Lys Asp Val Arg Lys Asp Asn Arg Ala Val Gln Lys Leu
                275                 280                 285
Arg Arg Glu Val Glu Lys Ala Lys Arg Ala Leu Ser Ser Gln His Gln
                290                 295                 300
```

```
Ala Arg Ile Glu Ile Glu Ser Phe Phe Glu Gly Asp Phe Ser Glu
305                 310                 315                 320

Thr Leu Thr Arg Ala Lys Phe Glu Glu Leu Asn Met Asp Leu Phe Arg
            325                 330                 335

Ser Thr Met Lys Pro Val Gln Lys Val Leu Glu Asp Ser Asp Leu Lys
        340                 345                 350

Lys Ser Asp Ile Asp Glu Ile Val Leu Val Gly Gly Ser Thr Arg Ile
    355                 360                 365

Pro Lys Ile Gln Gln Leu Val Lys Glu Phe Phe Asn Gly Lys Glu Pro
370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
            405                 410                 415

Leu Asp Val Cys Pro Leu Thr Leu Gly Ile Glu Thr Val Gly Gly Val
        420                 425                 430

Met Thr Lys Leu Ile Pro Arg Asn Thr Val Val Pro Thr Lys Lys Ser
    435                 440                 445

Gln Ile Phe Ser Thr Ala Ser Asp Asn Gln Pro Thr Val Thr Ile Lys
450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
            485                 490                 495

Ile Glu Val Thr Phe Glu Ile Asp Val Asn Gly Ile Leu Arg Val Thr
        500                 505                 510

Ala Glu Asp Lys Gly Thr Gly Asn Lys Asn Lys Ile Thr Ile Thr Asn
    515                 520                 525

Asp Gln Asn Arg Leu Thr Pro Glu Glu Ile Glu Arg Met Val Asn Asp
530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
            565                 570                 575

Gly Asp Lys Glu Lys Leu Gly Gly Lys Leu Ser Ser Glu Asp Lys Glu
        580                 585                 590

Thr Met Glu Lys Ala Val Glu Glu Lys Ile Glu Trp Leu Glu Ser His
    595                 600                 605

Gln Asp Ala Asp Ile Glu Asp Phe Lys Ala Lys Lys Lys Glu Leu Glu
610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ser Glu Lys Asp Glu Leu
            645                 650

<210> SEQ ID NO 12
<211> LENGTH: 261
<212> TYPE: PRT
<213> ORGANISM: Cricetulus griseus

<400> SEQUENCE: 12

Met Cys Ile Ala Phe Arg Met Leu Leu Ser Val Ile Pro Lys Val Cys
1               5                   10                  15

Trp Cys Asp Cys Phe Leu Glu Val Leu Ser Leu Ser Lys Thr Val Phe
```

```
                 20                  25                  30
Leu Ser Phe Leu Gly Leu Glu Met Ala Thr Pro Gln Ser Val Phe Val
             35                  40                  45

Phe Ala Ile Cys Ile Leu Met Ile Thr Glu Leu Ile Leu Ala Ser Lys
         50                  55                  60

Ser Tyr Tyr Asp Ile Leu Gly Val Pro Lys Ser Ala Ser Glu Arg Gln
 65                  70                  75                  80

Ile Lys Lys Ala Phe His Lys Leu Ala Met Lys Tyr His Pro Asp Lys
                 85                  90                  95

Asn Lys Ser Pro Asp Ala Glu Ala Lys Phe Arg Glu Ile Ala Glu Ala
            100                 105                 110

Tyr Glu Thr Leu Ser Asp Ala His Arg Arg Lys Glu Tyr Asp Thr Val
        115                 120                 125

Gly His Thr Ala Phe Thr Asn Gly Lys Gly Gln Arg Gly Ser Gly Ser
    130                 135                 140

Pro Phe Glu Gln Ser Phe Asn Phe Asn Phe Asp Asp Leu Phe Lys Asp
145                 150                 155                 160

Phe Asn Leu Phe Gly Gln Asn Gln Asn Thr Arg Ser Lys Lys His Phe
                165                 170                 175

Glu Asn His Phe Gln Thr His Gln Asp Gly Ser Asn Arg Gln Arg His
            180                 185                 190

His Phe Gln Glu Phe Ser Phe Gly Gly Gly Leu Phe Asp Asp Met Phe
        195                 200                 205

Glu Asp Met Glu Lys Met Phe Ser Phe Ser Gly Phe Asp Thr Thr Asn
    210                 215                 220

Arg His Thr Val Gln Thr Glu Asn Arg Phe His Gly Ser Ser Lys His
225                 230                 235                 240

Cys Arg Thr Val Thr Gln Arg Gly Asn Met Val Thr Thr Tyr Thr
                245                 250                 255

Asp Cys Ser Gly Gln
            260

<210> SEQ ID NO 13
<211> LENGTH: 332
<212> TYPE: PRT
<213> ORGANISM: Cricetulus griseus

<400> SEQUENCE: 13

Met Ala Thr Leu Lys Asp Gln Leu Ile Val Asn Leu Leu Lys Glu Glu
 1               5                  10                  15

Gln Thr Pro Gln Asn Lys Ile Thr Ile Val Gly Val Gly Ala Val Gly
                 20                  25                  30

Met Ala Cys Ala Ile Ser Ile Leu Met Lys Asp Leu Ala Asp Glu Leu
             35                  40                  45

Ala Leu Val Asp Val Met Glu Asp Lys Leu Lys Gly Glu Met Met Asp
         50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Val Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125
```

| | | | | | | | | | | | |
|---|---|---|---|---|---|---|---|---|---|---|---|
|Pro|Asp|Cys|Lys|Leu|Leu|Ile|Val|Ser|Asn|Pro|Val|Asp|Ile|Leu|Thr|
| |130| | | |135| | | |140| | | | | | |

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
        195                 200                 205

Val Ser Leu Lys Asn Leu Asn Pro Glu Leu Gly Thr Asp Thr Asp Lys
210                 215                 220

Glu Gln Trp Asn Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Asp Asp Val Phe
        275                 280                 285

Leu Ser Val Pro Cys Val Leu Gly Gln Asn Gly Ile Ser Asp Val Val
290                 295                 300

Lys Val Thr Leu Thr Ser Glu Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 14
<211> LENGTH: 678
<212> TYPE: DNA
<213> ORGANISM: Unknown
<220> FEATURE:
<223> OTHER INFORMATION: Discosoma sp.

<400> SEQUENCE: 14

```
atggcctcct ccgaggacgt catcaaggag ttcatgcgct tcaaggtgcg catggagggc      60
tccgtgaacg gccacgagtt cgagatcgag ggcgagggcg agggccgccc ctacgagggc     120
acccagaccg ccaagctgaa ggtgaccaag ggcggccccc tgcccttcgc ctgggacatc     180
ctgtcccctc agttccagta cggctccaag gcctacgtga agcaccccgc cgacatcccc     240
gactacttga agctgtcctt ccccgagggc ttcaagtggg agcgcgtgat gaacttcgag     300
gacggcggcg tggtgaccgt gacccaggac tcctccctgc aggacggcga gttcatctac     360
aaggtgaagc tgcgcggcac caacttcccc tccgacggcc ccgtaatgca gaagaagacc     420
atgggctggg aggcctccac cgagcggatg taccccgagg acggcgccct gaagggcgag     480
atcaagatga ggctgaagct gaaggacggc ggccactacg acgccgaggt caagaccacc     540
tacatggcca agaagcccgt gcagctgccc ggcgcctaca agaccgacat caagctggac     600
atcacctccc acaacgagga ctacaccatc gtggaacagt acgagcgcgc cgagggccgc     660
cactccaccg gcgcctaa                                                   678
```

<210> SEQ ID NO 15
<211> LENGTH: 225
<212> TYPE: PRT
<213> ORGANISM: Unknown
<220> FEATURE:

<223> OTHER INFORMATION: Discosoma sp.

<400> SEQUENCE: 15

```
Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225
```

<210> SEQ ID NO 16
<211> LENGTH: 678
<212> TYPE: DNA
<213> ORGANISM: Unknown
<220> FEATURE:
<223> OTHER INFORMATION: Discosoma sp.

<400> SEQUENCE: 16

```
atggcctcct ccgagaacgt catcaccgag ttcatgcgct tcaaggtgcg catggagggc      60
accgtgaacg gccacgagtt cgagatcgag ggcgagggcg agggccgccc ctacgagggc     120
cacaacaccg tgaagctgaa ggtgaccaag ggcggccccc tgcccttcgc ctgggacatc     180
ctgtcccccc agttccagta cggctccaag gtgtacgtga agcacccgc cgacatcccc     240
gactacaaga gctgtccttt ccccgagggc ttcaagtggg agcgcgtgat gaacttcgag     300
gacggcggcg tggcgaccgt gacccaggac tcctccctgc aggacggctg cttcatctac     360
aaggtgaagt tcatcggcgt gaacttcccc tccgacggcc ccgtgatgca gaagaagacc     420
atgggctggg aggcctccac cgagcgcctg taccccgcg acggcgtgct gaagggcgag     480
acccacaagg ccctgaagct gaaggacggc ggccactacc tggtggagtt caagtccatc     540
tacatggcca agaagcccgt gcagctgccc ggctactact acgtggacgc caagctggac     600
```

```
atcacctccc acaacgagga ctacaccatc gtggagcagt acgagcgcac cgagggccgc    660
caccacctgt tcctgtag                                                  678
```

<210> SEQ ID NO 17
<211> LENGTH: 225
<212> TYPE: PRT
<213> ORGANISM: Unknown
<220> FEATURE:
<223> OTHER INFORMATION: Discosoma sp.

<400> SEQUENCE: 17

```
Met Ala Ser Ser Glu Asn Val Ile Thr Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Thr His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ala Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```

<210> SEQ ID NO 18
<211> LENGTH: 720
<212> TYPE: DNA
<213> ORGANISM: Aequorea victoria

<400> SEQUENCE: 18

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
```

```
gtgaaccgca tcgagctgaa gggcatcgac ttcaaggagg acggcaacat cctgggcac        420 aagctggagt acaactacaa cagccacaac gtctatatca tggccgacaa gcagaagaac        480
ggcatcaagg tgaacttcaa gatccgccac aacatcgagg acggcagcgt gcagctcgcc        540
gaccactacc agcagaacac ccccatcggc gacggccccg tgctgctgcc cgacaaccac        600
tacctgagca cccagtccgc cctgagcaaa gaccccaacg agaagcgcga tcacatggtc        660
ctgctggagt tcgtgaccgc cgccgggatc actctcggca tggacgagct gtacaagtaa        720

<210> SEQ ID NO 19
<211> LENGTH: 239
<212> TYPE: PRT
<213> ORGANISM: Aequorea victoria

<400> SEQUENCE: 19

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 20
<211> LENGTH: 711
<212> TYPE: DNA
<213> ORGANISM: Unknown
<220> FEATURE:
<223> OTHER INFORMATION: Discosoma sp.

<400> SEQUENCE: 20
atggtgagca agggcgagga ggataacatg gccatcatca aggagttcat gcgcttcaag        60
gtgcacatgg agggctccgt gaacggccac gagttcgaga tcgagggcga gggcgagggc       120
```

| | | |
|---|---|---|
| cgcccctacg agggcaccca gaccgccaag ctgaaggtga ccaagggtgg ccccctgccc | 180 |
| ttcgcctggg acatcctgtc ccctcagttc atgtacggct ccaaggccta cgtgaagcac | 240 |
| cccgccgaca tccccgacta cttgaagctg tccttcccccg agggcttcaa gtgggagcgc | 300 |
| gtgatgaact cgaggacgg cggcgtggtg accgtgaccc aggactcctc cctccaggac | 360 |
| ggcgagttca tctacaaggt gaagctgcgc ggcaccaact tcccctccga cggccccgta | 420 |
| atgcagaaga agaccatggg ctgggaggcc tcctccgagc ggatgtaccc cgaggacggc | 480 |
| gccctgaagg gcgagatcaa gcagaggctg aagctgaagg acggcggcca ctacgacgct | 540 |
| gaggtcaaga ccacctacaa ggccaagaag cccgtgcagc tgcccggcgc ctacaacgtc | 600 |
| aacatcaagt tggacatcac ctcccacaac gaggactaca ccatcgtgga acagtacgaa | 660 |
| cgcgccgagg ccgccactc caccggcggc atggacgagc tgtacaagta g | 711 |

```
<210> SEQ ID NO 21
<211> LENGTH: 236
<212> TYPE: PRT
<213> ORGANISM: Unknown
<220> FEATURE:
<223> OTHER INFORMATION: Discosoma sp.

<400> SEQUENCE: 21
```

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

```
<210> SEQ ID NO 22
<211> LENGTH: 600
<212> TYPE: DNA
```

<213> ORGANISM: Streptomyces alboniger

<400> SEQUENCE: 22

| | | |
|---|---|---|
| atgaccgagt acaagcccac ggtgcgcctc gccacccgcg acgacgtccc cagggccgta | 60 |
| cgcacccctcg ccgccgcgtt cgccgactac cccgccacgc cacaccgt cgatccggac | 120 |
| cgccacatcg agcgggtcac cgagctgcaa gaactcttcc tcacgcgcgt cgggctcgac | 180 |
| atcggcaagg tgtgggtcgc ggacgacggc gccgcgtgg cggtctggac cacgccggag | 240 |
| agcgtcgaag cgggggcggt gttcgccgag atcggcccgc gcatggccga gttgagcggt | 300 |
| tcccggctgg ccgcgcagca acagatggaa ggcctcctgg cgccgcaccg gcccaaggag | 360 |
| cccgcgtggt tcctggccac cgtcggcgtc tcgcccgacc accagggcaa gggtctgggc | 420 |
| agcgccgtcg tgctccccgg agtggaggcg gccgagcgcg ccggggtgcc cgccttcctg | 480 |
| gagacctccg cgccccgcaa cctccccttc tacgagcggc tcggcttcac cgtcaccgcc | 540 |
| gacgtcgagg tgcccgaagg accgcgcacc tggtgcatga cccgcaagcc cggtgcctga | 600 |

<210> SEQ ID NO 23
<211> LENGTH: 199
<212> TYPE: PRT
<213> ORGANISM: Streptomyces alboniger

<400> SEQUENCE: 23

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195

<210> SEQ ID NO 24
<211> LENGTH: 795
<212> TYPE: DNA
<213> ORGANISM: Escherichia coli

<400> SEQUENCE: 24

```
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcagggc gcccggttct ttttgtcaag accgacctgt ccggtgccct gaatgaactg   180
caggacgagg cagcgcggct atcgtggctg ccacgacgg gcgttccttg cgcagctgtg   240
ctcgacgttg tcactgaagc gggaagggac tggctgctat gggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg gctcgcgcc agccgaactg ttcgccaggc tcaaggcgcg catgcccgac   540
ggcgaggatc tcgtcgtgac ccatggcgat gcctgcttgc cgaatatcat ggtgaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
gacgagttct tctga                                                    795
```

<210> SEQ ID NO 25
<211> LENGTH: 267
<212> TYPE: PRT
<213> ORGANISM: Escherichia coli

<400> SEQUENCE: 25

```
Met Gly Ser Ala Ile Glu Gln Asp Gly Leu His Ala Gly Ser Pro Ala
1               5                   10                  15

Ala Trp Val Glu Arg Leu Phe Gly Tyr Asp Trp Ala Gln Gln Thr Ile
            20                  25                  30

Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
    50                  55                  60

Asp Glu Ala Ala Arg Leu Ser Trp Leu Ala Thr Thr Gly Val Pro Cys
65                  70                  75                  80

Ala Ala Val Leu Asp Val Val Thr Glu Ala Gly Arg Asp Trp Leu Leu
                85                  90                  95

Leu Gly Glu Val Pro Gly Gln Asp Leu Leu Ser Ser His Leu Ala Pro
            100                 105                 110

Ala Glu Lys Val Ser Ile Met Ala Asp Ala Met Arg Arg Leu His Thr
        115                 120                 125

Leu Asp Pro Ala Thr Cys Pro Phe Asp His Gln Ala Lys His Arg Ile
    130                 135                 140

Glu Arg Ala Arg Thr Arg Met Glu Ala Gly Leu Val Asp Gln Asp Asp
145                 150                 155                 160

Leu Asp Glu Glu His Gln Gly Leu Ala Pro Ala Glu Leu Phe Ala Arg
                165                 170                 175

Leu Lys Ala Arg Met Pro Asp Gly Asp Asp Leu Val Val Thr His Gly
            180                 185                 190

Asp Ala Cys Leu Pro Asn Ile Met Val Glu Asn Gly Arg Phe Ser Gly
        195                 200                 205

Phe Ile Asp Cys Gly Arg Leu Gly Val Ala Asp Arg Tyr Gln Asp Ile
    210                 215                 220

Ala Leu Ala Thr Arg Asp Ile Ala Glu Glu Leu Gly Gly Glu Trp Ala
```

```
                225                 230                 235                 240
Asp Arg Phe Leu Val Leu Tyr Gly Ile Ala Ala Pro Asp Ser Gln Arg
                    245                 250                 255
Ile Ala Phe Tyr Arg Leu Leu Asp Glu Phe Phe
                260                 265

<210> SEQ ID NO 26
<211> LENGTH: 399
<212> TYPE: DNA
<213> ORGANISM: Aspergillus terreus

<400> SEQUENCE: 26
atggccaagc ctttgtctca agaagaatcc accctcattg aaagagcaac ggctacaatc      60
aacagcatcc ccatctctga agactacagc gtcgccagcg cagctctctc tagcgacggc     120
cgcatcttca ctggtgtcaa tgtatatcat tttactgggg gaccttgtgc agaactcgtg     180
gtgctgggca ctgctgctgc tgcggcagct ggcaacctga cttgtatcgt cgcgatcgga     240
aatgagaaca ggggcatctt gagccctgc ggacggtgcc gacaggtgct ctcgatctg      300 catcctggga tcaaagccat agtgaaggac agtgatggac agccgacggc agttgggatt     360
cgtgaattgc tgccctctgg ttatgtgtgg gagggctaa                           399

<210> SEQ ID NO 27
<211> LENGTH: 132
<212> TYPE: PRT
<213> ORGANISM: Aspergillus terreus

<400> SEQUENCE: 27

Met Ala Lys Pro Leu Ser Gln Glu Glu Ser Thr Leu Ile Glu Arg Ala
1               5                   10                  15

Thr Ala Thr Ile Asn Ser Ile Pro Ile Ser Glu Asp Tyr Ser Val Ala
                20                  25                  30

Ser Ala Ala Leu Ser Ser Asp Gly Arg Ile Phe Thr Gly Val Asn Val
            35                  40                  45

Tyr His Phe Thr Gly Gly Pro Cys Ala Glu Leu Val Val Leu Gly Thr
        50                  55                  60

Ala Ala Ala Ala Ala Ala Gly Asn Leu Thr Cys Ile Val Ala Ile Gly
65                  70                  75                  80

Asn Glu Asn Arg Gly Ile Leu Ser Pro Cys Gly Arg Cys Arg Gln Val
                85                  90                  95

Leu Leu Asp Leu His Pro Gly Ile Lys Ala Ile Val Lys Asp Ser Asp
            100                 105                 110

Gly Gln Pro Thr Ala Val Gly Ile Arg Glu Leu Leu Pro Ser Gly Tyr
        115                 120                 125

Val Trp Glu Gly
    130

<210> SEQ ID NO 28
<211> LENGTH: 1026
<212> TYPE: DNA
<213> ORGANISM: Escherichia coli

<400> SEQUENCE: 28
atgaaaaagc tgaactcac cgcgacgtct gtcgagaagt ttctgatcga aagttcgac      60 agcgtctccg aacctgatgca gctctcggag ggcgaagaat ctcgtgctttt cagcttcgat    120 gtaggagggc gtggatatgt cctgcgggta aatagctgcg ccgatggttt ctacaaagat    180
```

```
cgttatgttt atcggcactt tgcatcggcc gcgctcccga ttccggaagt gcttgacatt    240
ggggaattca gcgagagcct gacctattgc atctcccgcc gtgcacaggg tgtcacgttg    300
caagacctgc ctgaaaccga actgcccgct gttctgcagc cggtcgcgga ggccatggat    360
gcgatcgctg cggccgatct tagccagacg agcgggttcg gcccattcgg accgcaagga    420
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg agcgaggcg    660 atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                              1026
```

<210> SEQ ID NO 29  
<211> LENGTH: 341  
<212> TYPE: PRT  
<213> ORGANISM: Escherichia coli
<400> SEQUENCE: 29

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220
```

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
            245                 250                 255

Ala Gly Ser Pro Arg Leu Arg Ala Tyr Met Leu Arg Ile Gly Leu Asp
        260                 265                 270

Gln Leu Tyr Gln Ser Leu Val Asp Gly Asn Phe Asp Asp Ala Ala Trp
    275                 280                 285

Ala Gln Gly Arg Cys Asp Ala Ile Val Arg Ser Gly Ala Gly Thr Val
290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
            325                 330                 335

Pro Arg Ala Lys Glu
            340

<210> SEQ ID NO 30
<211> LENGTH: 720
<212> TYPE: DNA
<213> ORGANISM: Aequorea victoria

<400> SEQUENCE: 30
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcggcta cggcctgaag tgcttcgccc gctacccega ccacatgaag   240 cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagct accagtccgc cctgagcaaa gaccccaacg agaagcgcga tcacatggtc   660
ctgctggagt tcgtgaccgc cgccgggatc actctcggca tggacgagct gtacaagtaa   720

<210> SEQ ID NO 31
<211> LENGTH: 239
<212> TYPE: PRT
<213> ORGANISM: Aequorea victoria

<400> SEQUENCE: 31

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 32
<211> LENGTH: 698
<212> TYPE: DNA
<213> ORGANISM: Unknown
<220> FEATURE:
<223> OTHER INFORMATION: Discosoma sp.

<400> SEQUENCE: 32
atgagcgagc tgattaagga gaacatgcac atgaagctgt acatggaggg caccgtggac      60
aaccatcact tcaagtgcac atccgagggc gaaggcaagc cctacgaggg cacccagacc     120
atgagaatca aggtggtcga gggcggccct ctccccttcg ccttcgacat cctggctact     180
agcttcctct acggcagcaa gaccttcatc aaccacaccc agggcatccc cgacttcttc     240
aagcagtcct tccctgaggg cttcacatgg gagagagtca ccacatacga agacgggggc     300
gtgctgaccg ctacccagga caccagcctc caggacggct gcctcatcta caacgtcaag     360
atcagagggg tgaacttcac atccaacggc cctgtgatgc agaagaaaac actcggctgg     420
gaggccttca ccgagacgct gtaccccgct gacggcggcc tggaaggcag aaacgacatg     480
gccctgaagc tcgtgggcgg gagccatctg atcgcaaaca tcaagaccac atatagatcc     540
aagaaacccg ctaagaacct caagatgcct ggcgtctact atgtggacta cagactggaa     600
agaatcaagg aggccaacaa cgagacctac gtcgagcagc acgaggtggc agtggccaga     660
tactgcgacc tccctagcaa actggggcac aagcttaa                             698

<210> SEQ ID NO 33
<211> LENGTH: 233
<212> TYPE: PRT
<213> ORGANISM: Unknown
<220> FEATURE:
<223> OTHER INFORMATION: Discosoma sp.

<400> SEQUENCE: 33

Met Ser Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly

```
                20                  25                  30
Lys Pro Tyr Glu Gly Thr Gln Thr Met Arg Ile Lys Val Val Glu Gly
                35                  40                  45

Gly Pro Leu Pro Phe Ala Phe Asp Ile Leu Ala Thr Ser Phe Leu Tyr
        50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn
225                 230
```

<210> SEQ ID NO 34
<211> LENGTH: 1032
<212> TYPE: DNA
<213> ORGANISM: Bacteriophage P1

<400> SEQUENCE: 34

```
atgtccaatt tactgaccgt acaccaaaat ttgcctgcat taccggtcga tgcaacgagt     60
gatgaggttc gcaagaacct gatggacatg ttcagggatc gccaggcgtt ttctgagcat    120
acctggaaaa tgcttctgtc cgtttgccgg tcgtgggcgg catggtgcaa gttgaataac    180
cggaaatggt ttcccgcaga acctgaagat gttcgcgatt atcttctata tcttcaggcg    240
cgcggtctgg cagtaaaaac tatccagcaa catttgggcc agctaaacat gcttcatcgt    300
cggtccgggc tgccacgacc aagtgacagc aatgctgttt cactggttat gcggcggatc    360 cgaaagaaa acgttgatgc cggtgaacgt gcaaaacagg ctctagcgtt cgaacgcact    420
gatttcgacc aggttcgttc actcatggaa atagcgatc gctgccagga tacgtaat     480 ctggcatttc tggggattgc ttataacacc ctgttacgta tagccgaaat tgccaggatc    540
agggttaaag atatctcacg tactgacggt gggagaatgt taatccatat ggcagaacg    600 aaaacgctgg ttagcaccgc aggtgtgaga aaggcactta gcctgggggt aactaaactg    660
gtcgagcgat ggatttccgt ctctggtgta gctgatgatc gaataacta cctgttttgc    720 cgggtcagaa aaaatggtgt tgccgcgcca tctgccacca gccagctatc aactcgcgcc    780
ctggaaggga ttttgaagc aactcatcga ttgatttacg cgctaagga tgactctggt     840 cagagatacc tggcctggtc tggacacagt gcccgtgtcg gagccgcgcg agatatggcc    900
```

```
cgcgctggag tttcaatacc ggagatcatg caagctggtg gctggaccaa tgtaaatatt    960
gtcatgaact atatccgtaa cctggatagt gaaacagggg caatggtgcg cctgctggaa   1020
gatggcgatt ag                                                       1032
```

<210> SEQ ID NO 35
<211> LENGTH: 343
<212> TYPE: PRT
<213> ORGANISM: Bacteriophage P1

<400> SEQUENCE: 35

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 36
<211> LENGTH: 1269
<212> TYPE: DNA
<213> ORGANISM: Saccharomyces cerevisiae

<400> SEQUENCE: 36

| | | |
|---|---|---|
| atgagccaat tgatatatt atgtaaaaca ccacctaagg tcctggttcg tcagtttgtg | 60 |
| gaaaggtttg aaagaccttc aggggaaaaa atagcatcat gtgctgctga actaacctat | 120 |
| ttatgttgga tgattactca taacggaaca gcaatcaaga gagccacatt catgagctat | 180 |
| aatactatca taagcaattc gctgagtttc gatattgtca acaaatcact ccagtttaaa | 240 |
| tacaagacgc aaaaagcaac aattctggaa gcctcattaa agaaattaat tcctgcttgg | 300 |
| gaatttacaa ttattcctta caatggacaa aaacatcaat ctgatatcac tgatattgta | 360 |
| agtagtttgc aattacagtt cgaatcatcg gaagaagcag ataagggaaa tagccacagt | 420 |
| aaaaaaatgc ttaaagcact tctaagtgag ggtgaaagca tctgggagat cactgagaaa | 480 |
| atactaaatt cgtttgagta tacctcgaga tttacaaaaa caaaaacttt ataccaattc | 540 |
| ctcttcctag ctactttcat caattgtgga agattcagcg atattaagaa cgttgatccg | 600 |
| aaatcattta aattagtcca aaataagtat ctgggagtaa taatccagtg tttagtgaca | 660 |
| gagacaaaga caagcgttag taggcacata tacttcttta gcgcaagggg taggatcgat | 720 |
| ccacttgtat atttggatga attttgagg aactctgaac cagtcctaaa acgagtaaat | 780 |
| aggaccggca attcttcaag caacaaacag gaataccaat tattaaaaga taacttagtc | 840 |
| agatcgtaca acaaggcttt gaagaaaaat gcgccttatc caatctttgc tataaagaat | 900 |
| ggcccaaaat ctcacattgg aagacatttg atgacctcat ttctgtcaat gaagggccta | 960 |
| acggagttga ctaatgttgt gggaaattgg agcgataagc gtgcttctgc cgtggccagg | 1020 |
| acaacgtata ctcatcagat aacagcaata cctgatcact acttcgcact agtttctcgg | 1080 |
| tactatgcat atgatccaat atcaaaggaa atgatagcat tgaaggatga actaatcca | 1140 |
| attgaggagt ggcagcatat agaacagcta aagggtagtg ctgaaggaag catacgatac | 1200 |
| cccgcatgga atgggataat atcacaggag gtactagact acctttcatc ctacataaat | 1260 |
| agacgcata | 1269 |

<210> SEQ ID NO 37
<211> LENGTH: 423
<212> TYPE: PRT
<213> ORGANISM: Saccharomyces cerevisiae

<400> SEQUENCE: 37

Met Ser Gln Phe Asp Ile Leu Cys Lys Thr Pro Pro Lys Val Leu
1               5                   10                  15

Arg Gln Phe Val Glu Arg Phe Glu Arg Pro Ser Gly Glu Lys Ile Ala
            20                  25                  30

Ser Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

```
Ile Pro Ala Trp Glu Phe Thr Ile Ile Pro Tyr Asn Gly Gln Lys His
                100                 105                 110

Gln Ser Asp Ile Thr Asp Ile Val Ser Ser Leu Gln Leu Gln Phe Glu
            115                 120                 125

Ser Ser Glu Glu Ala Asp Lys Gly Asn Ser His Ser Lys Lys Met Leu
        130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Pro Ile Phe Ala Ile Lys Asn Gly Pro Lys Ser
290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
            340                 345                 350

His Tyr Phe Ala Leu Val Ser Arg Tyr Tyr Ala Tyr Asp Pro Ile Ser
        355                 360                 365

Lys Glu Met Ile Ala Leu Lys Asp Glu Thr Asn Pro Ile Glu Glu Trp
370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
            420

<210> SEQ ID NO 38
<211> LENGTH: 122
<212> TYPE: DNA
<213> ORGANISM: Simian virus 40

<400> SEQUENCE: 38
aacttgttta ttgcagctta taatggttac aaataaagca atagcatcac aaatttcaca     60
aataaagcat ttttttcact gcattctagt tgtggtttgt ccaaactcat caatgtatct   120
ta                                                                  122

<210> SEQ ID NO 39
```

```
<211> LENGTH: 494
<212> TYPE: DNA
<213> ORGANISM: Homo sapiens

<400> SEQUENCE: 39
cctggccttg gaagttgcca ctccagtgcc caccagcctt gtcctaataa aattaagttg      60
catcattttg tctgactagg tgtccttcta taatattatg gggtggaggg gggtggtatg     120
gagcaagggg caagttggga agacaacctg tagggcctgc ggggtctatt gggaaccaag     180
ctggagtgca gtggcacaat cttggctcac tgcaatctcc gcctcctggg ttcaagcgat     240 tccctgcct cagcctcccg agttgttggg attccaggca tgcatgacca ggctcagcta      300 attttgttt ttttggtaga cgggtttt caccatattg gccaggctgg tctccaactc        360
ctaatctcag gtgatctacc caccttggcc tcccaaattg ctgggattac aggcgtgaac     420
cactgctccc ttccctgtcc ttctgatttt aaaataacta taccagcagg aggacgtcca     480
gacacagcat aggc                                                       494

<210> SEQ ID NO 40
<211> LENGTH: 225
<212> TYPE: DNA
<213> ORGANISM: Bos taurus

<400> SEQUENCE: 40
ctgtgccttc tagttgccag ccatctgttg tttgccccct ccccgtgcct tccttgaccc      60
tggaaggtgc cactcccact gtcctttcct aataaaatga ggaaattgca tcgcattgtc     120
tgagtaggtg tcattctatt ctgggggtg gggtggggca ggacagcaag ggggaggatt     180
gggaagacaa tagcaggcat gctggggatg cggtgggctc tatgg                     225

<210> SEQ ID NO 41
<211> LENGTH: 56
<212> TYPE: DNA
<213> ORGANISM: Homo sapiens

<400> SEQUENCE: 41
aataaaggaa atttatttc attgcaatag tgtgttggaa ttttttgtgt ctctca           56

<210> SEQ ID NO 42
<211> LENGTH: 56
<212> TYPE: DNA
<213> ORGANISM: Herpes simplex virus

<400> SEQUENCE: 42
aataaaggaa atttatttc attgcaatag tgtgttggaa ttttttgtgt ctctca           56

<210> SEQ ID NO 43
<211> LENGTH: 462
<212> TYPE: DNA
<213> ORGANISM: Unknown
<220> FEATURE:
<223> OTHER INFORMATION: Mus sp.
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t

<400> SEQUENCE: 43
ctgtaagtct gcagaaattg atgatctatt aaacaataaa gatgtccact aaaatggaag      60
```

| | |
|---|---|
| tttttcctgt catactttgt taagaagggt gagaacagag tacctacatt ttgaatggaa | 120 |
| ggattggagc tacggggggtg ggggtggggt gggattagat aaatgcctgc tctttactga | 180 |
| aggctcttta ctattgcttt atgataatgt ttcatagttg gatatcataa tttaaacaag | 240 |
| caaaaccaaa ttaagggcca gctcattcct cccactcatg atctatagat ctatagatct | 300 |
| ctcgtgggat cattgttttt ctcttgattc ccactttgtg gttctaagta ctgtggtttc | 360 |
| caaatgtgtc agtttcatag cctgaagaac gagatcagca gcctctgttc cacatacact | 420 |
| tcattctcag tattgntttg ccnngttcta attccatcag aa | 462 |

<210> SEQ ID NO 44
<211> LENGTH: 996
<212> TYPE: DNA
<213> ORGANISM: Cricetulus griseus
<220> FEATURE:
<221> NAME/KEY: misc_feature
<222> LOCATION: (501)..(557)
<223> OTHER INFORMATION: n is a, c, g, or t

<400> SEQUENCE: 44

| | |
|---|---|
| agctttagaa ggattaagag gtatggcttt gttggaggaa gtgtgtcatg gtggtgggct | 60 |
| tagaggtttc aaaagcttaa gctaggccca gagtctgtct gtcaggatgt agaactctta | 120 |
| gctatttctc cagcaccatg tctgcctgtg tctagccatg gtccaagcca tgatgctaat | 180 |
| ggcctaacct ctcaaactgt aagcaggctt ccagttaaac cttttttta taagagttgc | 240 |
| cttggtcatg gtgtctcttc tcagccatag aacaatgact aagacaaata gctaaagctt | 300 |
| agttagcact tctatgtacc agacagtatt ctatatttca atataaattc atctgctctt | 360 |
| cacagtcata ttgtgaaaag ggtactatca tcctcacttt aaaaaaagca aactgaggca | 420 |
| atggactctt ggataactta catgtttctc ttccttcctt ccttccttcc ttccttcctt | 480 |
| ccttccttcc ttccttcctt nnnnnnnnnn nnnnnnnnnn nnnnnnnnnn nnnnnnnnnn | 540 |
| nnnnnnnnnn nnnnnncgg gtttctctgt gtagctttgg agcctatcct ggcactcgct | 600 |
| ctggagacca ggctggcctc gcactcacac agatccgcct gcctctgcct cccgagtgct | 660 |
| gggattaaag gcgtgcgcca ccaacgcccg gcaacttaca tatttctatc aagtcttttt | 720 |
| tttttttttt ttttttttgct ctcattccct tccatagcct agggtgagca cagcaggcct | 780 |
| gacagtccaa gggcccaaag ggcctaagga ccgtggtgag ctggagtctt gccttttctg | 840 |
| ctttgttttc tttaagtca gtctggctgt gaacttagtc tcctaaacag ctgaggtaca | 900 |
| ggtgcaacgc actcctcatc ctgggccggc tgaagggtgt gtctgcggtg gtggggtcc | 960 |
| gagggcacat tggcggaaga agtgcaactg gaagcg | 996 |

<210> SEQ ID NO 45
<211> LENGTH: 978
<212> TYPE: DNA
<213> ORGANISM: Cricetulus griseus
<220> FEATURE:
<221> NAME/KEY: misc_feature
<222> LOCATION: (495)..(611)
<223> OTHER INFORMATION: n is a, c, g, or t

<400> SEQUENCE: 45

| | |
|---|---|
| gaaagaaata ctgtcaaggc tggagacaca gttcagtgat atctctaatt tcatagataa | 60 |
| agtgggctga aggaatagtt gagtgtgaaa cactaggttc tgggttcagg ctctagcact | 120 |
| gcaaaacaaa gataaccatg atgatataag cttataccag ggagtttaga tatacaaaca | 180 |

```
aaatgaaact acatgtattc ccactatgca gacattattt atcaactcct tactacagtg      240
ttctggtttt tcttcttcgt ttaaatagct ctctctagcc taggcctccc tatgtagctc      300
aggctgtcct caaactggaa acaaagagct gagactacgg gtgagcatca ccatgcccga      360
ctacatttag ttactgaaat tatttgattt cctaaagact tattttgcaa aatttctcca      420
ggtgtgtgtg tgtgtgtgtg tgtttgtgtg tgtgtgtgtg tgtgtgtgtg tgtgtgtggg      480
gggtgtgcgg ggggnnnnnn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnnn nnnnnnnnnn      600
nnnnnnnnnn ngtgtccgct aactccaagc cggatatgcc accggttcga ttttccgctg      660
ctctgggggc cgacgtggtc ccggacatta caatgtggtc aggctggggt aaagatctgt      720
gagactcagt ctggaagtct ggctagcgag aaaagccggg cattcccagc gtcagggagt      780
gggaacgcgt ttgtggaaga cccgggcctc cagcaacccc tctctgctgt ccactcgccc      840
tcaggcccag ctcgccaggc ggaggacagc tgtgcagcca cgctggacac ccacccctcc      900
cgcgctgggc ccgccctcta gcccgtagga ccaataggca ctgagaataa ccgtgcgtca      960
cgcggagcgg gcctatcg                                                    978

<210> SEQ ID NO 46
<211> LENGTH: 983
<212> TYPE: DNA
<213> ORGANISM: Cricetulus griseus

<400> SEQUENCE: 46
aaggagcaca gtggaacttt gtggagtcac agaggaaatt gggaaacgtt cagcctttac       60
taacaaaaat ggaaacctta ttttccacat gttttattta cattggcatt tctttcagtt      120
tctaattgaa attaaaaatg caggagtttt ctcccagtg tacctcccca aggaagaaaa       180
ttccttttga ggagataaaa atacttgtta atgtccccca aatataccta ccttaacttc      240
tttctccaaa caacttttcca ttgtgggctt ttattcatc agtagttcgt gtactgtatt      300
gtaagacact tagtcgaaga atgatattaa caacatgtgg tattaaccac aagaaatgtg      360
atttagactg tttaaaatac cttaggacat tagccaccag ttaaataaag cacctttagt      420
cccaacattt cactcaggaa gcagaggcag agaggaactc tgagttcaag cccatcctga      480
tctccagagc aagttccagg acagccaggg atacacagag aagccctgac tcggaaagga      540
aaagaaagaa ggaaaagaga agtttcaatg gaaattgagt atctgttcaa cttaaagtct      600
tttgtaatgg ccagaggtac ttcaaatcat agtgcaagtt tgtcacacaa attttttagag     660 aatgatggaa aaacaatctc tataactttg gtttctaggc taatgctttg atttcctctt      720
ggttaaataa atgatgatgt acaaacattg ctcccccccc ccactgcaaa ttgtactcca      780
tggaggagtt tctataatgt tgcagtttct acctaatggt gaccaaatgc cagtgaaagg      840
attgtaagag tacttgtcac atatactact cacctcattt caagaatgtg gacctgcttt      900
taaacattaa gagcaaatcg taattatata agaaataagc aaatgaaact attagactgt      960
ttgaaaagtc ttttctttta cag                                              983

<210> SEQ ID NO 47
<211> LENGTH: 1193
<212> TYPE: DNA
<213> ORGANISM: Cricetulus griseus

<400> SEQUENCE: 47
ttaggaaaaa gaaggggggg ctaaaccctc ccccaccacc ttcttctccc gcagcgcacc       60
```

```
acacacagcg cgcgggctgc tcgctcggca cccggcggcc ccggcgcgtc cctgcctgca    120
tttatcaagc tgctccccccc caccccattt ttttcggaaa acgcattggc cttttggagt    180
ttaatcagaa gaggattttt gtccctgtcc cccccctctt tcatcgtccc cctcgcgtgt    240
ctctgccgtg gagggcttaa gcaatccagt ggagacggat ccatgcctgc gctcgagcgt    300
gtgtgtgcga gtgtaaattg ccgagaagcg ggggaaatca caggacttct tcaaatgctg    360
gactgaaaat tgtaattcat ctgccgccgc cgctgccttt ccgcccctc tgtcgtgctc    420 ttgagatctc cggttgggat tcctacggat tgacattttc agtgaagcca aaccgtgggg    480
acgggacgca atctggaaac cctcctgatt ttactctacc tagctctccc ccacctcctc    540
ctcattgcaa gtttcaaaga agcttatacc aggagacttc tgaagatcga tggtgtcgtt    600
gccttatata tttgtttggg ttttaccaaa aagcaaaaca aaaaaaagag ggggaaactt    660
gacagaagat catgctgtcc tttaaaaata agtaagtttt ttgcacagga atttggttta    720
gtttaacttt caacggacgc atttgatttt tttctttaaa tacattcgag caaatttaat    780
ttccaaacag tttaatgcag tctctttagt gtgtaacttg tagcggatat gcccttcctc    840
ccctgagtat ataaagaaca cacctgtttt taacttgcca agtcgtccct cccctcacct    900
ttcagcattg cggagtaagt agactgatat taacaaagct taataaataa tgtgcctcgt    960
gaaataaaga accgaaagga atttgaataa aaatttcctg catctaatgc aaggggggaa    1020
acaccagaat caagtgttcc gcgtaactga agacaccccc tcatccagga atgcaaaagc    1080
acatccaata aaagagctgg attataacta tttttttttc ttttgggggt gtggggcggg    1140
agtcaggacg agaagtgctg ttgatatacc tgcagctttt ttttcgggga agg    1193

<210> SEQ ID NO 48
<211> LENGTH: 1000
<212> TYPE: DNA
<213> ORGANISM: Cricetulus griseus

<400> SEQUENCE: 48
ctacctgact ttcacctctc tctctgtaca tctgacttct tctgtgtctt gctggtgtca    60
atgcatctct tcttcctggc gacctctctt tccccggaag tcccacttat tccctcctgc    120
ctagctattg gccattcagc cctttgttaa accaatcaga agttacctta ggcagagaca    180
catctttaca gtatacgaag attatcccac aatagaggcc agcctggtct acagagcaag    240
ttccaggaca gccagggcta tacagagaaa ccctgtctca aaaaaccaaa aacaatcata    300
aaagacattg acatggaaat aatttttaaa taacttgaac aacaatcctc tttaagcatg    360
cctagttagt ttgggagggg tttactaatg attcttgaga aagacccctg tatatgactg    420 aacccctttgg aagcttgcat ataatatttc ttaaacaaga agaaattctt tccttctct    480 ctttcatgaa atgttctcac ccctttctcc ttcattatct cctcgaagca tttcaaaacc    540
tggtcaatcc atgagagtgc cccttttgtga gtgaaaaatg gttgaatagc cataatctca    600
tatggctcaa cttaacatct agccatccta caccatatag cagacagtag cccatttcat    660
ttgcatttgc attttttcagt ataatgtgta atgcacactg agaacatgtg tgcattattg    720
taggtgatat ggtgaataaa tcactgcttt tggctacata cattccagct ggaaggggca    780
ataccttttt gaaagctaat tgtactggag gaatggctgg gaaccctaac tatgtaaagt    840
ccagccagtc tggaggtgga ggcaggagga atcagttaaa ggtctttttg aacttttgtag    900 ggagttggag caggggccag cctggctaca ggaacctcaa acaaatcaac agaaaaacaa    960
```

```
aacaaagtgc atgcatactg cttttggggcc attggacaac                            1000
```

<210> SEQ ID NO 49
<211> LENGTH: 872
<212> TYPE: DNA
<213> ORGANISM: Cricetulus griseus

<400> SEQUENCE: 49

```
gggaacatta tggggcgaca agctagagaa aaaaaatgat atattccagg gtggaaagtg        60
ctcgcttgac tattcataga acagaatagc cacagcatag cgggggggctc agtactaggt     120
tgcaaatggc caggccaatt ctgggactta accccaagaa aagaaaaatt ggcaaggcca      180
ggatagacaa atgcagctgg cctaggggtg aagggaaaac agttggctga aagagccac       240
gattcgcaga gaggcagaac acagactagg acccagctcg agcgtgcag gccgggtggg      300
taacatagag cccgggcgct cggctacccg agaacgtgag ggaggcttgg aagggcagag     360
atgcgttccc aggcgaccac agcatctatg ctgaggctga gcagctcggg acccgagggg     420
acttaggagg agaaaaggcc gcatactgct tcggggtaag ggacagaccg gggaaggacc     480
caagtcccac cgcccagagg gaactgacac gcagaccccg cagcagtccc cggggggccgg   540
gtgacgggag gacctggacg gttaccggcg gaaacggtct cgggttgaga ggtcacctga    600
gggacaggca gctgctgaac caataggacc ggcgcacagg gcggatgctg cctctcattg   660
gcggccgttg agagtaacca gtagccaatg agtcagcccg gggggcgtag cggtgacgta   720
agttgcggag gaggccgctt cgaatcggca gcggccagct tggtggcatg gaccaatcag   780
cgtcctccaa cgagaagcgc cttcaccaat cggaggcctc cacgacgggg ctgggggag    840
ggtatataag ccaagtcggc ggcggcgcgc tc                                  872
```

<210> SEQ ID NO 50
<211> LENGTH: 1121
<212> TYPE: DNA
<213> ORGANISM: Cricetulus griseus

<400> SEQUENCE: 50

```
agctcactgt gcagaccatg ctggccttga actccaaagt aatccgcctg tccctgcctc      60
cctagtgcgg ggattaaagg catgtgccac tgtgcctgct ttgtgtcttt agaccaagag    120
gttgcacttt ctggttggtt acgcgtgact atgactaagt ctcaggaaaa aagtaaccta    180
cctgctaatt aagctcagaa taggccacag gagaggacga ctggcagttt ccacaaagca   240
cagtactttt tcgtcagcct atgtcatcat aggttattaa ggacttctgt ggttcagcat   300
tcaaaaaagc aaaccaggag agtattatca gtaattccaa gtaaaactta atgctttaaa   360
gagaaacggc ttacttcctg agtaacttgg aaaacctcct tatccacagt acaaacgatt    420
tccttcctct gggccttgtt ttttcttttt ctttttttt tttgtttttt ttgttttttt     480
gttttgtttt gttttccaag acagggtttc tctgtgtagc tttggagccc atcctggcac    540
tcgctctgga gacgaggctg gcctcgaact cgcagagatc cgcctgcttc tgcctccca    600
gtgctggtat taaaggcgtg cacaaccaat tcccggctga tttggggctt taagcagaag    660
ttatttctga agtgtttcat acatatatga aaactgatta ttttaaccct tttaagagca   720
tatagaatta accaacttga gaaacatctt tccttcccca cctttgcctt gatactaaga   780
ttctagccaa acacagagaa aacagggatt tcaatatttt ttgtcatata ctgaagctag   840
atgtggttat gacagcattg agaaagctga ggtgggaata tcaggacatc taagccagct   900
agtacttctt aggatgatgc tgccttcaaa aatgttttgg agaggtaata ataccttaa    960
```

| | |
|---|---|
| catcacaagc aaacaaaagt tgctttacat aaatagaaag ggtctttcct tcctaagaaa | 1020 |
| gtattaattt agctttcttt tcaacagatg aacaaaaggc ttgctagtag attcttaata | 1080 |
| ttagaaatac tgtcagtaca atatcatgag tatgtgatac t | 1121 |

<210> SEQ ID NO 51
<211> LENGTH: 946
<212> TYPE: DNA
<213> ORGANISM: Cricetulus griseus

<400> SEQUENCE: 51

| | |
|---|---|
| ccggattccg gcttgttgga cctggctgcc tgcccggaga tccacttgct cttttggaac | 60 |
| aatttcagaa atagacgtag tgcttgctgg gggaaatata tccctcgtgg ttaggaaact | 120 |
| ctaggcctta gcccctctgt aacggtatac ccatttcgga acggaagaaa tttcccctta | 180 |
| ccggcctcat cctgggtgat gaggctccgc cctagctggt gggtggttac aagtccctgc | 240 |
| ttcctggtat agctgtttga aatttgaatc tggtgccaag ccaaggtggc tgccagcccc | 300 |
| ttctcaccgt gcttgcatgt gctttgggct ctagtaaggt ccgaagtctg ccccgaaatg | 360 |
| cctacttgga agtctcatcc atggccagca gccactagac ttatattact accctgctct | 420 |
| gaaattgcgc cagcgcatcg gcttgcccgg catggcctgt cagtcataga gatccccggc | 480 |
| tggtcataaa acttgtggtg gggggggaa gcctgcgcat gcgcgggccc cagcacgtta | 540 |
| ctttgcctta gggtcgcacc ttgtggccgt tatcgggccc tctgctcttg atttttggta | 600 |
| cttactggag caacctggca ccctacttac tgtaggattc tgggtattaa gagcggaaga | 660 |
| gcagttctct gatggtgtcc aaggagaggc catctccttt cagagttaat caaaatgagt | 720 |
| gagtcctcgg aaggctacac ttacacggag acctcggtat tacttttacg tttcaaggtg | 780 |
| aggaccagag cagaccctgg tattaatgct ttccatgcta tggctactct catttcccac | 840 |
| ttccgccctt ttagtcaatg gaaagtagac caaaggatac aaagattata aacttggtga | 900 |
| ttatactttg gagtgacctc aatgacagga aatgcttcca ccttag | 946 |

<210> SEQ ID NO 52
<211> LENGTH: 1074
<212> TYPE: DNA
<213> ORGANISM: Cricetulus griseus

<400> SEQUENCE: 52

| | |
|---|---|
| gaagccccgc ccatcgcagg cgagacttcc ggctgtaacc gcttgcagcg gcttctgctg | 60 |
| acggagtcgg aacggcgga gctcaggatg gtgttgctcg agagcgagca ggtaccggct | 120 |
| gcccggaggg ccggggactc gagcgaatgg ggtcagctcg ggtcgcattt ccctctttgc | 180 |
| gggcgggcca gggccgtgac gcggcggggc gaggactgga ggctgcctaa ccgggcgtgt | 240 |
| tgtgttgcag ttcctgacgg agctgaccag gctcttccag aagtgccggt cgtcgggcag | 300 |
| cgtgtacatc accctgaaga agtgtaagca gcccccggga cgacggctgg aggggccgc | 360 |
| tcactccggc ctcccggcac cggccacctc cggggctcag ggtcggggca gtggcgagtc | 420 |
| aggcagccca gccctgctc cgtcagtgag gtcgcacatg ccttggggtc gcagtgtcaa | 480 |
| gtcgttgctc ccacgattga accccctg agtgacgatg agtgtggcga gtttatggga | 540 |
| ggcgagagca gtggtggtgg attgggtca ccctggaact cttctctgcc gttttcactt | 600 |
| tggagccggc agcaacgcct gtggcggtgg gtgttcccca ggttgtaact ttttttttt | 660 |
| ttttttaac gcagatgatg gtcgcaccaa acccactcca cggaagagtg cggtggagag | 720 |

| | |
|---|---|
| cgttgagccc gcagaaaaca agtgtctgtt gagagctacg gatgggaaaa ggaagatcag | 780 |
| caccgtggtg agctggagtc ctgtcttttc tgctttgcct tcttttaagt ctgtctgccg | 840 |
| tgaacttaat cctgtctcaa ataactgagg tacaggtgac ggtctatccc acggccggct | 900 |
| ggtaagctga atttttaaaaa ctgtcacagc agacgcctcg gcctgtgccg gggtcacagt | 960 |
| gtatgttgtc agccgagaca gatacagtga tgatttctgt ggggctaaga gattgaatcc | 1020 |
| gggccagggt cttcattgtg tctgtcatca ccctgttact aagccacacc gcca | 1074 |

<210> SEQ ID NO 53
<211> LENGTH: 1010
<212> TYPE: DNA
<213> ORGANISM: Cricetulus griseus

<400> SEQUENCE: 53

| | |
|---|---|
| atggtggtgg tggcagcgtc gccgagcgcg gccacggcgg ccccgaaagt actgcttcta | 60 |
| tcgggccagc ccgccgcgga cggccgggcg ctgccactca tggttccagg ctcgcgggca | 120 |
| gcagggtccg aggcgaacgg ggcgccacag gctcgcaagc ggcagcgcct cacgcacctg | 180 |
| agcccggagg agaaggcgct gcggaggtgg gctcggcggg cggggcggca aggccgggca | 240 |
| tgggacccctt tctcgtgtgg cggtcggagg ggctctgtgg ggtggcgtag atgagcctct | 300 |
| agtacctatt tctggaggga ggcacggagc tgaggtgaca gccccctccga aggtctgctt | 360 |
| agtctgtgtc ggggagtcta acacttgtca gacgggacct gacgctcagc cctctgtgaa | 420 |
| tgcttgctct tcttggagga cccatggcag gtccgctct ggctgttgtt gcagccgctt | 480 |
| gggaacttaa cactgggatc cgagtccacca tcctccggca gcccgagttg agcttgggga | 540 |
| gggacggttg gtagcgcccc cgccgccttc acggagcctg ttggacagaa tcggaactag | 600 |
| aaagccgcgg gggaggaggg aagatgctta tgacgcaacg ggaatgtgtg tcagcccggt | 660 |
| ggtaaaataa gactcgagtg gacagcaaca tgggagagaa tcgagcaagt cttcaaggcc | 720 |
| cacgggcaga aaagctgtgg ttttttgtctt tttgagagga ggagcctcag aatgtgttta | 780 |
| ccactgttta gtcttattct gtaaagtcag cgaaagcacc agctggccac atttacaaat | 840 |
| gaagatacag gaaagctgaa gatgactcgg ttcgttatgt gccctgtctt ccttcaggaa | 900 |
| actgaaaaac agagtagcag cgcagactgc ccgagatcga agaaagccc ggatgagcga | 960 |
| gctggaacag caagtggtgg atttggaaga agaggtaaag ggatttaagg | 1010 |

<210> SEQ ID NO 54
<211> LENGTH: 1087
<212> TYPE: DNA
<213> ORGANISM: Cricetulus griseus

<400> SEQUENCE: 54

| | |
|---|---|
| gaaaaatgct ttcagaaagc agttcatttt tgaaaggtgt gatgcttgga agcatcttct | 60 |
| atgccttgat cactacgcta ggccacatta ggattgggca cagaaacagg acacaccacc | 120 |
| atgagcatca ccacctgcaa gctcctaaca aagaagatat ctcgaaaatc tcagcggctg | 180 |
| agcgcatgga gctcagtaag agcttccggg tatactgtat agttcttgta aacccaaag | 240 |
| atgtgagtct ttgggctgca gtgaaggaga cttggaccaa acactgtgac aaagcagagt | 300 |
| tcttcagttc tgaaaatgtt aaagtgtttg agtcaattaa cgtggacact gatgacatgt | 360 |
| ggttgatgat gaggaaagct tataaatatg cctttgataa atacaaagag cagtacaact | 420 |
| ggttcttcct tgcacgcccc agtacttttg ctgtgattga aaatctaaaa tattttttgt | 480 |
| taaaaaagga tccatcgcag ccttttctatc taggacacac tgtaaaatct ggagaccttg | 540 |

| aatatgtgag tgtggatgga gggattgtct taagcatag agtcaatgaaa agactcaaca | 600 |
| gccttctcag tgttccggaa aagtgtcctg aacaaggtgg gatgatttgg aagatatctg | 660 |
| aagataagca gctagcagtc tgcctgaaat atgctggagt atttgcggaa aatgcggaag | 720 |
| acgctgatag aaaagatgta tttaatacca aatctgttgg gcttttcatt aaagaggcca | 780 |
| tgtctaacca cccgaaccag gtagtagaag gatgctgttc caatatggct gtcactttta | 840 |
| atggactaac tcctaatcag atgcatgtga tgatgtatgg ggtgtaccgg cttagggcct | 900 |
| ttggacatgt tttcaacgat gcgttggttt tcttacctcc aaacggttct gataatgact | 960 |
| gacaaaaagc aagagcatgc atttggtaac cacattaaga catgttatgc tttctaatcg | 1020 |
| ataatgcatc taacacagta gtgtgtttct tttccttatc tggtcacatt gaagtctact | 1080 |
| tgtacat | 1087 |

<210> SEQ ID NO 55
<211> LENGTH: 1047
<212> TYPE: DNA
<213> ORGANISM: Cricetulus griseus

<400> SEQUENCE: 55

| atggctcaag ctgggagaac agggtatgat aaccgagaga tcgtgatgaa gtacatccat | 60 |
| tataagctgt cacagagggg ctacgagtgg gatgtgggag atgtggacgc cgcgcccctg | 120 |
| ggcgccgccc ccaccctgg catcttctcc ttccagcctg agagcaaccc aacgcccgct | 180 |
| gtgcaccggg acatggctgc caggacatcg ccactaaggc ccatagtcgc caccactggg | 240 |
| cctaccctta gccccgtgcc acctgtggtc cacctgaccc tccgccgggc tggggatgac | 300 |
| ttctcccgtc gctaccgtcg cgacttcgcg gagatgtcca gtcagctgca cctgacgccc | 360 |
| tcaccgcga ggggacgctt tgctacgtg gtggaggaac tcttcaggga tggggtgaac | 420 |
| tgggggagga ttgtggcctt ctttgagttc ggtggggtca tgtgtgtgga gagcgtcaac | 480 |
| agggagatgt caccccctggt ggacaacatc gccctgtgga tgaccgagta cctgaaccgg | 540 |
| catctgcaca cctggatcca ggataacgga ggctgggtag gtgcatgtct gactgaatga | 600 |
| gtctgggctt tgctctcaaa gccaagatgc agagaggctg gggacttagt ggatcctggg | 660 |
| tcaaaatgag ccatgagcca atgaatgaaa atccagtttg tagctttgct ccccgtccca | 720 |
| gtacctttct ctggtcagat cacaccctgc caatactgtg ctagctcctg cctgcaggct | 780 |
| gtaaaagagc aaaggtccag tatttttgat ccagtaggat ctgaagataa atggtatccc | 840 |
| tccagtgagt cccagagtta cttgaagtct gagtagcttg ttgcagatgt tctggttcct | 900 |
| gggtaggaac cagacctcca gctttctctg catcttaggc tactctgttg gactaataac | 960 |
| tgacaaggtc caactagaca aataggctcc accagaggac gcaggcatac cttttctgac | 1020 |
| tcacttggga acattttccc aaagaaa | 1047 |

<210> SEQ ID NO 56
<211> LENGTH: 980
<212> TYPE: DNA
<213> ORGANISM: Cricetulus griseus

<400> SEQUENCE: 56

| atgaccctga gtgtgactac ttcccttgct gggtcagttg gtgctaccag gaaccagcca | 60 |
| agagacattg gttctccgtg ttgtcatgct aggctcgggg aggctggtgt gggcaacttc | 120 |
| ctggtggctg atcctggagt aattgcccta cagcagatga cagccaacct ctgggcctct | 180 |

```
ccagtgatta attttttttt tttttacaat ttcatttgtg tatacaatgc tttctgatca      240
cacatctcat tcttacacct ttcccaatct catacccctc caatcaccct cttactttca      300 tgtcttttg tttctcttgt gacccaatga acttaactag tactatctct gtgagcactg       360
atgtggtcac atccaaatta taatcaagac tgacatcaaa atctttcatt tctgtatctc      420
agtttggttt cacttttcag ggtaatatac attttaaaga tgtcacaccg aagtgctgat      480
ctaactaaaa tctaatagta ctgatgagac acaatataac aaggtgtaat tcacccatc       540 agtttgtttt ttttttttaa ccagtgttca tctgtaggtt accactagag aacaaactaa      600
agcctactaa catctccagg ttacatatcc atgaccaata aatggtttta ttctcttaat      660
gatcatactt tcatagtgaa agtgaacttg gaggccaggt atgaatttag aagtgtgaag      720
tattcttgca aaaatgaagt gcactcccaa cccccagtct agcctctgtg taaatacgc       780 aggtttagga acaagttaaa cataactgtt aagataaagt cagcagactc acaaagtagg      840
cagttctcca ggacaagact gttttcttca gcatacggtg tccatcagag tgtggaagag      900
tgttgcagaa tacttgtttc cactgtgtga gcatgtgtcc ttgtgattgg ttaattaaag      960
agctgaatgg ccaatagcta                                                  980

<210> SEQ ID NO 57
<211> LENGTH: 1227
<212> TYPE: DNA
<213> ORGANISM: Cricetulus griseus

<400> SEQUENCE: 57
acactggcca agacaacagt gaccggagga cctgcctttg cggctccgag aggtaagcgc       60
cgcggcctgc tcttgccaga cctcctttga gcctgtctcg tggctcctcc tgacccgggg     120
ggcttctgtc gccctcagat cggaacgccg ccgcgctccg ggactacagc ctgttgctgg     180
acttcgagac tgcagacgga ccgaccgctg agcactggcc cacagcgccg gcaagatgaa     240
gttccctatg gtggcggcgg cgctgctgct gctctgcgcg gtgcgggccg aggaggagga     300
caagaaggag gatgtgggca cggtggtcgg catcgacctg ggaccacct attcctggtg      360 agtggggag agagagtggg gcgtggcctc ctgggccggc gtgagagagt gaggtgctga     420
ttccttttct gtggggtgtt tccgtcagcg ttggtgtgtt caagaacggc cgcgtggaga     480
tcatagccaa cgatcagggc aaccgcatca cgccgtcgta tgtggccttc actcctgaag     540
gcgagcgtct gattggcgat gcggccaaga accagctcac ctccaatccc gagaacacgg     600
tcttcgacgc caagcgcctc atcggacgca cttggaatga cccttcagtg cagcaggaca     660
tcaagttctt gcctttcaag gtccaatccg tttttttttt ttttttttta acccacgctt     720
aaggggctgt tagggtggtg ggaaatttag aggttgaaac gaggcggaaa acattcaaa      780 cggctaaaag gatgcagtcg gggtttacgt aacggtttta gatgtagtct cttttagtat     840
tatgagaaga gacacagtgt tacaatgtct aaaagttgga aggtagacta aaaactgtcg     900
atcggcccac aatacagctg tgcttagtct tagtcaagat ctccctaagg gaccaaaatg     960
aattcaagtt atggaagaga agaaacggat tatttttcct ttaaactttg tggtgccatt    1020
gtttcaactt cggaaaaatt acctttaaat tattctttat cataggtggt tgaaaagaaa    1080
actaaaccat acattcaagt tgatattgga ggtgggcaaa ccaaaacatt tgccccagaa    1140
gaaatttctg ccatggttct cactaaaatg aaagaaactg ctgaagcata tttgggaaag    1200
aaggtaaata catgtgtggc atggtgt                                        1227
```

<210> SEQ ID NO 58
<211> LENGTH: 1039
<212> TYPE: DNA
<213> ORGANISM: Cricetulus griseus

<400> SEQUENCE: 58

| | | | | | | |
|---|---|---|---|---|---|---|
| atgtgcatag | cttttcgaat | gctgctgtct | gttataccaa | aggtttgttg | gtgtgattgt | 60 |
| tttctagaag | tcttatcctt | gagtaaaact | gttttccttt | ctttttagg | attagaaatg | 120 |
| gctactcccc | aatcagtttt | tgtctttgca | atttgcattt | taatgataac | agaattaatc | 180 |
| ctagcctcaa | agagctacta | tgatatctta | ggtgtgccaa | atctgcctc | agagcgacaa | 240 |
| atcaagaagg | cctttcacaa | attagcgatg | aagtaccacc | ccgacaaaaa | taagagccct | 300 |
| gatgctgaag | caaaattcag | agagattgca | gaaggtaagt | aaatgattct | gcagtctcat | 360 |
| gggtatttat | agtaagtaac | tgaaaatttt | gtgtgctctt | aaagatgtta | tggaaattgg | 420 |
| agagtttatg | tagattttg | caatttatct | tgttagaata | gatacctggc | ttctgggtaa | 480 |
| gtaattgatt | atagtaggta | atttttgttg | ttgttgttta | caattctaaa | atgcccgttt | 540 |
| cccttattta | tttatgagat | tactatgtat | aaaatgaggt | attagaaagt | actgtgtata | 600 |
| aaatgaggga | ttagaaagcc | aaaattctta | tcaagtaatt | taaatgtatt | tttactaagt | 660 |
| actgacttac | tgtacacaaa | ataggttaaa | agtgtctatt | gcatctacat | ttcaaaacaa | 720 |
| tgtgtcttta | aaaaattgtg | aagtatgtta | ctagttctaa | aactaattgt | acatccctgc | 780 |
| atattactta | agtagttaat | gggcctaact | aggagttgga | attaaaaatt | tactttatct | 840 |
| agtaaagtga | aaaacgtggt | tttgtattag | ttgaacacat | ttgttaattt | aattctttaa | 900 |
| tacaaataat | agttttgcac | aaataatatg | aagatgaaca | aattagttt | tcccacatgt | 960 |
| ttatttgtga | taatggcagc | atttaacaaa | tatattaatt | gaagaaataa | ttattagaaa | 1020 |
| gacattattg | ttctaacta | | | | | 1039 |

<210> SEQ ID NO 59
<211> LENGTH: 1124
<212> TYPE: DNA
<213> ORGANISM: Cricetulus griseus

<400> SEQUENCE: 59

| | | | | | | |
|---|---|---|---|---|---|---|
| gtcccaaaaa | gttcaaagtc | caagatggca | acactcaagg | accagctgat | tgtgaatcta | 60 |
| cttaaggaag | aacagacccc | ccagaacaag | attacgattg | ttggggttgg | tgctgttggc | 120 |
| atggcttgtg | ccatcagtat | cctcatgaag | gtaagtgggg | atccttcagg | tcacaagccc | 180 |
| aagcattggg | aggccctaca | ttgtcacatt | gtatataaaa | ctatcaagtt | tcaggcactc | 240 |
| attcaagaga | gccttctatg | aaacattttg | caacatggtg | atgcacaaag | gattatccaa | 300 |
| agtaacatta | taaaggtta | gcagactgag | gcctttttaa | aatgctctac | agtatgttag | 360 |
| catgccctac | cagcaagaaa | gaatgcaggg | agttgaagga | acctagggtc | tcccatatgg | 420 |
| taggtaacca | ttggagctgt | atgcccagct | cttaagtaat | ttttaattga | aatgtatatg | 480 |
| tacctgtggt | aaaaattaat | atcctaccga | atgggatatc | ttgaatttct | atccaatccc | 540 |
| taatgttccc | tgacttataa | tagttttcct | ttgagaaaaa | agtgtgtgtg | tgtgtatgag | 600 |
| cacactgggt | aactgagggt | aattggcttc | tctcctacct | tgtgggttct | gggggtcaaa | 660 |
| ctcagctcac | caggcttgtg | caggaattgc | tttcccctcg | agccatctca | atcagagcta | 720 |
| aaatttaatt | ggtcagataa | ccacataatt | gcattgaaaa | acacttgctg | agacagggta | 780 |
| aattttttt | taagatttta | tttatttatt | atgtatacaa | cattctgctt | ccatatatat | 840 |

```
ctacacacca gaagagggca ccagatctca taacgggtgg ttgtgaggca ctatgtggtt    900
tctgggaatt gaactcatga cctctggaag agcagtcagt gctcttaacc tcagagccat    960
ttctccagcc ctcagggtaa atgttaatat atatattttt atatatgggg ctaagacagg   1020
gtttctcttt gtaacccagg ctgttctgga actcattctg tagaccagac tggcctcaaa   1080
ctcatctgcc tgcctttgcc tcccaaatat taaaaataaa gttt                   1124

<210> SEQ ID NO 60
<211> LENGTH: 34
<212> TYPE: DNA
<213> ORGANISM: Saccharomyces cerevisiae

<400> SEQUENCE: 60
gaagttccta ttctctagaa agtataggaa cttc                                 34

<210> SEQ ID NO 61
<211> LENGTH: 34
<212> TYPE: DNA
<213> ORGANISM: Bacteriophage P1
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t

<400> SEQUENCE: 61
ataacttcgt atannntann ntatacgaag ttat                                 34
```